(12) United States Patent
Radosavljevic et al.

(10) Patent No.: US 12,419,831 B2
(45) Date of Patent: *Sep. 23, 2025

(54) HYDROCORTISONE ORAL LIQUID FORMULATIONS

(71) Applicant: Eton Pharmaceuticals, Inc., Deer Park, IL (US)

(72) Inventors: Danka Radosavljevic, Palatine, IL (US); Sean Brynjelsen, Barrington, IL (US); Romona Bhattacharya, Franklin Park, NJ (US); Kalyan Kathala, Monroe, NJ (US)

(73) Assignee: Eton Pharmaceuticals, Inc., Deer Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/932,033

(22) Filed: Oct. 30, 2024

(65) Prior Publication Data

US 2025/0049704 A1    Feb. 13, 2025

Related U.S. Application Data

(63) Continuation of application No. 18/443,889, filed on Feb. 16, 2024, now Pat. No. 12,133,914, which is a continuation of application No. PCT/US2023/079494, filed on Nov. 13, 2023, which is a continuation-in-part of application No. 18/113,458, filed on Feb. 23, 2023, now Pat. No. 11,904,046.

(60) Provisional application No. 63/425,172, filed on Nov. 14, 2022.

(51) Int. Cl.
| | |
|---|---|
| *A61K 9/00* | (2006.01) |
| *A61K 9/08* | (2006.01) |
| *A61K 31/573* | (2006.01) |
| *A61K 47/10* | (2017.01) |
| *A61K 47/14* | (2017.01) |
| *A61K 47/18* | (2017.01) |
| *A61K 47/26* | (2006.01) |
| *A61K 47/46* | (2006.01) |

(52) U.S. Cl.
CPC ............. *A61K 9/0053* (2013.01); *A61K 9/08* (2013.01); *A61K 31/573* (2013.01); *A61K 47/10* (2013.01); *A61K 47/14* (2013.01); *A61K 47/183* (2013.01); *A61K 47/26* (2013.01); *A61K 47/46* (2013.01)

(58) Field of Classification Search
CPC ...... A61K 31/573; A61K 47/10; A61K 47/14; A61K 47/183; A61K 47/26; A61K 47/46; A61K 9/0053; A61K 9/0095; A61K 9/08
See application file for complete search history.

(56) References Cited

U.S. PATENT DOCUMENTS

| | | | |
|---|---|---|---|
| 3,696,195 A | 10/1972 | Crivellaro et al. | |
| 5,173,298 A * | 12/1992 | Meadows | A61K 9/1635 424/78.03 |
| 6,458,376 B1 | 10/2002 | Meadows | |
| 9,623,000 B2 | 4/2017 | Kindler et al. | |
| 9,675,559 B2 | 6/2017 | Huatan et al. | |
| 9,717,740 B1 | 8/2017 | Huatan et al. | |
| 11,291,672 B2 | 4/2022 | Kottayil et al. | |
| 11,904,046 B1 | 2/2024 | Radosavljevic et al. | |
| 12,133,914 B2 * | 11/2024 | Radosavljevic | |
| 2004/0022789 A1 | 2/2004 | Brewer et al. | |
| 2009/0123550 A1 * | 5/2009 | Phillips | A61K 31/341 514/171 |
| 2014/0303131 A1 * | 10/2014 | Perrett | A61P 1/00 514/180 |
| 2015/0313524 A1 | 11/2015 | Matsumoto et al. | |
| 2019/0105404 A1 | 4/2019 | Pipkin et al. | |
| 2022/0096496 A1 | 3/2022 | Chen et al. | |
| 2023/0099165 A1 | 3/2023 | Chen et al. | |
| 2024/0165020 A1 | 5/2024 | Zhao et al. | |
| 2024/0180820 A1 | 6/2024 | Radosavljevic et al. | |

FOREIGN PATENT DOCUMENTS

| | | |
|---|---|---|
| EP | 1527772 A1 | 5/2005 |
| EP | 2780003 A1 | 9/2014 |
| EP | 3189855 B1 | 3/2018 |
| EP | 2814469 B1 | 4/2020 |
| WO | WO-2008070387 A1 | 6/2008 |
| WO | WO-2009064457 A3 | 8/2009 |
| WO | WO-2018078285 A1 | 5/2018 |
| WO | WO-2022221470 A1 | 10/2022 |
| WO | WO-2023083825 A1 | 5/2023 |

OTHER PUBLICATIONS

Chong, et al. Stability of Hydrocortisone in Extemporaneously Compounded Suspensions. Journal of Informed Pharmacotherapy 13:100-110 (2003).

Elder, D. et al.., "Antimicrobial Preservatives Part One: Choosing a Preservative System", American Pharmaceutical Review, Jan. 1, 2012, retrieved from internet https://www.americanpharmaceuticalreview.com/Featured-Articles/38886-Antimicrobial-Preservatives-Part-One-Choosing-a-Preservative-System/, retrieved online Mar. 31, 2023, pp. 1-7.

Fawcett, et al. Stability of Hydrocortisone Oral Suspensions Prepared from Tablets and Powder. Annals of Pharmacotherapy. Oct. 29, 1995: 987-990.

Lebreux, F., "Preservative Deep Dive: Parabens and their Alternatives", Prospector, Jul. 7, 2017, retrieved from internet https://knowledge.ulprospector.com/6776/pcc-preservative-deep-dive-parabens-alternatives/, retrieved online Mar. 31, 2023, pp. 1-6.

(Continued)

*Primary Examiner* — Sarah Pihonak
(74) *Attorney, Agent, or Firm* — WILSON SONSINI GOODRICH & ROSATI

(57) ABSTRACT

Provided herein are oral liquid formulations of hydrocortisone. Also provided herein are methods of making and using hydrocortisone oral liquid compositions for the treatment of certain diseases including endocrine disorders, rheumatic disorders, collagen diseases, dermatologic diseases, and others.

25 Claims, No Drawings

(56) References Cited

OTHER PUBLICATIONS

MacArthur, et al. Steroid Control of Acute Middle Ear Inflammation in a Mouse Model. Archives of Otolaryngology—Head & Neck Surgery 135(5):453-457 (2009).
No Author, "CORTEF (brand of hydrocortisone tablets, USP)", The Upjohn Company, retrieved from internet: https://www.accessdata.fda.gov/drugsatfda_docs/label/pre96/008697s021lbl.pdf, Nov. 1993, pp. 1-2.
No Author, "CORTEF (hydrocortisone tablets, USP)", Pfizer, Pharmacia & Upjohn Co, retrieved from internet: https://www.accessdata.fda.gov/drugsatfda_docs/label/2016/008697s032_33lbl.pdf, Jul. 2016, pp. 1-9.
No Author, "CORTEF (hydrocortisone tablets, USP)", Pfizer, Pharmacia & Upjohn Co, retrieved from internet: https://www.accessdata.fda.gov/drugsatfda_docs/label/2019/008697s036lbl.pdf, Nov. 2019, pp. 1-9.
No Author, "Cortisol: What it is, Function, Symptoms & Levels", Cleveland Clinic, Dec. 10, 2021, retrieved from internet on Mar. 31, 2023: https://my.clevelandclinic.org/health/articles/22187-cortisol, pp. 1-14.
No Author, "Hydrocortisone (systemic): Drug Information", UpToDate, retrieved from internet on Mar. 31, 2023: https://www.uptodate.com/contents/hydrocortisone-systemic-drug-information, pp. 1-42.
No Author, "Flavoring agents in pharmaceutical formulations", PharmaEducation, retrieved from internet https://pharmaeducation.net/flavoring-agents-in-pharmaceutical-formulations/#A_Natural_flavoring_agent, retrieved on Mar. 31, 2023, pp. 1-10.
No Author, "Hydrocortisone 5mg/5ml Oral Solution", Jul. 11, 2022, retrieved from internet https://www.medicines.org.uk/emc/product/13899/smpc/print, retrieved on Oct. 6, 2022, pp. 1-6.
No Author, "Hydrocortisone Oral Suspension 2mg/2mL", Nationwide Children's Hospital, Mar. 22, 2010, 1 page.
No Author, "SOLU-CORTEF (hydrocortisone sodium succinate for injection, USP)", Pfizer Injectables, Pharmacia & Upjohn Co, retrieved from internet: https://www.accessdata.fda.gov/drugsatfda_docs/label/2016/009866s98_105lbl.pdf, Jul. 2016, pp. 1-15.
PCT/US2023/079494 International Search Report and Written Opinion dated Apr. 10, 2024.
Shaikh, Sabir M. et al. A Review on: Preservatives used in Pharmaceuticals and Impacts on Health. PharmaTutor 4(5):25-34 (2016).
U.S. Appl. No. 18/443,889 Notice of Allowance dated Sep. 16, 2024.
U.S. Appl. No. 18/443,889 Office Action dated Jun. 13, 2024.

* cited by examiner

HYDROCORTISONE ORAL LIQUID FORMULATIONS

CROSS REFERENCE TO RELATED APPLICATIONS

This application is a continuation of U.S. patent application Ser. No. 18/443,889, filed Feb. 16, 2024, which is a continuation of International Application No. PCT/US2023/079494, filed on Nov. 13, 2023, which claims the benefit of U.S. patent application Ser. No. 18/113,458, filed on Feb. 23, 2023, now U.S. Pat. No. 11,904,046, and U.S. Provisional Patent Application No. 63/425,172, filed on Nov. 14, 2022, each of which is incorporated herein by reference in its entirety.

BACKGROUND

Hydrocortisone is a glucocorticoid, which is an essential adrenocortical steroid that is both naturally occurring and synthetic. Hydrocortisone has salt-retaining properties and plays an important role in regulating the body's response to stress, blood pressure, blood glucose, metabolism, and suppressing inflammation. Synthetic hydrocortisone is used as replacement therapy in treating adrenocortical deficiency and is also indicated many other disorders. Hydrocortisone is currently prescribed in the form of oral tablets, (e.g., Cortef®). There remains a need for a liquid formulation of hydrocortisone.

SUMMARY

Disclosed herein is a liquid pharmaceutical composition comprising: hydrocortisone or a pharmaceutically acceptable salt thereof; and a nonaqueous liquid carrier; wherein the liquid pharmaceutical composition is an oral solution, and wherein the liquid pharmaceutical composition contains less than 5% weight by weight (% wt) of water. In some embodiments, the hydrocortisone or a pharmaceutically acceptable salt thereof is present in the liquid pharmaceutical composition in an amount of about 1 mg/mL. In some embodiments, the hydrocortisone or a pharmaceutically acceptable salt thereof is present in the liquid pharmaceutical composition in an amount of about 0.01% to about 10% weight by volume (w/v). In some embodiments, the liquid pharmaceutical composition contains less than 3% wt of water. In some embodiments, the liquid pharmaceutical composition is nonaqueous. In some embodiments, the liquid pharmaceutical composition contains no more than 2% wt of total impurity after stored at room temperature for 3 months, and wherein the total impurity is determined according to high-performance liquid chromatography (HPLC). In some embodiments, the liquid pharmaceutical composition retains at least 95% wt of the initial hydrocortisone amount after stored at room temperature for 3 months, and wherein the hydrocortisone amount is determined according to HPLC. In some embodiments, the liquid pharmaceutical composition remains stable after stored at ambient conditions for at least 3 months. In some embodiments, the nonaqueous liquid carrier is present in the liquid pharmaceutical composition in an amount of from about 70% wt to about 99.9% wt. In some embodiments, the nonaqueous liquid carrier comprises propylene glycol, glycerin, polyethylene glycol (PEG), alcohol, or a combination thereof. In some embodiments, the nonaqueous liquid carrier comprises PEG. In some embodiments, the PEG has a number average molecular weight of about 350 to about 450 g/mol. In some embodiments, PEG is present in the liquid pharmaceutical composition in an amount of about 30% to about 70% w/v. In some embodiments, the nonaqueous liquid carrier comprises propylene glycol. In some embodiments, propylene glycol is present in the liquid pharmaceutical composition in an amount of about 0.5% to about 10% w/v. In some embodiments, the nonaqueous liquid carrier comprises glycerin. In some embodiments, glycerin is present in the liquid pharmaceutical composition in an amount of about 40% to about 80% w/v. In some embodiments, the liquid pharmaceutical composition comprises a preservative, and wherein the preservative comprises an antimicrobial agent, a chelating agent, or an antioxidant, or any combinations thereof. In some embodiments, the antimicrobial agent comprises methyl paraben, ethyl paraben, propyl paraben, benzoic acid or a pharmaceutically acceptable salt thereof, sorbic acid or a pharmaceutically acceptable salt thereof, phenoxyethanol, benzyl alcohol, propionic acid, or a combination thereof. In some embodiments, the chelating agent comprises disodium ethylenediaminetetraacetic acid, polyphosphates, citric acid, calcium disodium edetate, ethylenediaminetetraacetic acid (EDTA), or a combination thereof. In some embodiments, the antioxidant comprises vitamin A, monothioglycerol, ascorbic acid, sodium bisulfite, sodium sulfite, α-Tocopherol acetate (vitamin E), butylated hydroxyanisole (BHA), butylated hydroxytoluene (BHT), or a combination thereof. In some embodiments, the liquid pharmaceutical composition comprises a flavoring agent, and the flavoring agent comprises vanillin, grape flavor, caramel flavor, maltol, raspberry flavor, fruity flavor, berry flavor, 4-hydroxy-3-methoxybenzaldehyde, methyl anthranilate, 3,5-dimethyl-1,2-cyclopentadione, 4-(4-hydroxyphenyl)butan-2-one, ethyl maltol, ethyl propionate, or a combination thereof. In some embodiments, the liquid pharmaceutical composition comprises a sweetener, wherein the sweetener is glucose, fructose, sucrose, xylitol, tagatose, sucralose, maltitol, isomaltulose, hydrogenated isomaltulose, lactitol, sorbitol, erythritol, trehalose, maltodextrin, polydextrose, or a combination thereof. In some embodiments, the hydrocortisone or a pharmaceutically acceptable salt thereof is present in an amount of about 0.01% to about 2% w/v; the nonaqueous liquid carrier comprises propylene glycol, glycerin, PEG, or a combination thereof; the liquid pharmaceutical composition further comprises: a preservative comprising an antioxidant, an antimicrobial agent, or a combination thereof; optionally, a sweetener; and optionally, a flavoring agent. In some embodiments, the hydrocortisone or a pharmaceutically acceptable salt thereof is present in the liquid pharmaceutical composition in an amount of about 0.05% to about 0.5% w/v; the nonaqueous liquid carrier comprises propylene glycol, glycerin, and polyethylene glycol 400 (PEG 400), wherein propylene glycol is present in the liquid pharmaceutical composition in an amount of about 2% to about 10% w/v, wherein PEG 400 is present in in the liquid pharmaceutical composition an amount of about 20% to about 70% w/v, and wherein the glycerin is present in the liquid pharmaceutical composition in an amount of about 40% to about 80% w/v; wherein the liquid pharmaceutical composition further comprises: a preservative comprising an antioxidant and an antimicrobial agent, wherein the antioxidant comprises BHA, BHT, or a combination thereof, and wherein the antimicrobial agent comprises methyl paraben, ethyl paraben, propyl paraben or a combination thereof; a sweetener, and wherein the sweetener comprises glucose, fructose, sucrose, xylitol, tagatose, sucralose, maltitol, or a combination thereof; and a flavoring agent, and wherein the flavoring agent comprises berry flavor, maltol, ethyl maltol, or a combination thereof. In some embodiments, the liquid pharmaceutical composition comprises hydrocortisone or a pharmaceutically acceptable salt thereof in an amount of about 0.1% w/v; PEG 400 in an amount of about 50% w/v; BHA in an amount of about 0.01% w/v; a mixture of parabens in an amount of about 0.2% w/v; sucralose in an amount of about 1% w/v; berry flavor in an amount of about 0.2% w/v; propylene glycol in an amount of about 5% w/v; ethyl maltol in an amount of about 0.2% w/v; and glycerin in the liquid pharmaceutical composition in an amount of about 62.2% w/v.

Disclosed herein is a method of treating a disease or condition, comprising administering the liquid pharmaceutical composition described herein to a subject in need thereof. In some embodiments, the disease or condition comprises inflammation. In some embodiments, the disease or condition comprises adrenal insufficiency. In some embodiments, the subject is not older than 17 years in age. In some embodiments, the disease or condition is selected from endocrine disorders, rheumatic disorders, collagen diseases, dermatologic diseases, allergic states, ophthalmic diseases, respiratory diseases, hematologic disorders, neoplastic diseases, edematous states, gastrointestinal diseases, acute exacerbation in multiple sclerosis, tuberculous meningitis with subarachnoid block or impending block when used concurrently with appropriate anti-tuberculous chemotherapy, trichinosis with neurologic or myocardial involvement, and hypercalcemia.

Disclosed herein is a kit comprising a package enclosing the liquid pharmaceutical composition described herein.

Disclosed herein is a liquid pharmaceutical composition comprising hydrocortisone or a pharmaceutically acceptable salt thereof; and a nonaqueous liquid carrier; wherein the liquid pharmaceutical composition is an oral solution, and wherein the liquid pharmaceutical composition contains less than 5% weight by weight (% wt) of water. In some embodiments, the hydrocortisone or a pharmaceutically acceptable salt thereof is present in the liquid pharmaceutical composition in an amount of 0.8 mg/mL to 1.2 mg/mL. In some embodiments, the hydrocortisone or a pharmaceutically acceptable salt thereof is present in the liquid pharmaceutical composition in an amount of about 1 mg/mL. In some embodiments, the hydrocortisone or a pharmaceutically acceptable salt thereof is present in the liquid pharmaceutical composition in an amount of about 0.01% to about 10% w/v. In some embodiments, the liquid pharmaceutical composition contains less than 3% wt of water. In some embodiments, the liquid pharmaceutical composition contains less than 1% wt of water. In some embodiments, the liquid pharmaceutical composition is nonaqueous. In some embodiments, the liquid pharmaceutical composition contains no more than 2% wt of total impurity after stored at about 2° C. to about 8° C. for 3, 6, 9, 12, 18, 24, 30, or 36 months. In some embodiments, the liquid pharmaceutical composition contains no more than 2% wt of total impurity after stored at refrigerated conditions for 3, 6, 9, 12, 18, 24, 30, or 36 months. In some embodiments, the liquid pharmaceutical composition contains no more than 2% wt of total impurity after stored at about 15° C. to about 25° C. for 3 months. In some embodiments, the liquid pharmaceutical composition contains no more than 2% wt of total impurity after stored at about 15° C. to about 25° C. for 6, 9, 12, 18, or 24 months. In some embodiments, the liquid pharmaceutical composition contains no more than 2% wt of total impurity after stored at about 15° C. to about 25° C., with temperature excursions permitted up to 30° C., for 3 months. In some embodiments, the liquid pharmaceutical composition contains no more than 2% wt of total impurity after stored at about 15° C. to about 25° C., with temperature excursions permitted up to 30° C., for 6, 9, 12, 18, or 24 months. In some embodiments, the liquid pharmaceutical composition contains no more than 2% wt of total impurity after stored at about 15° C. to about 30° C. for 3 months. In some embodiments, the liquid pharmaceutical composition contains no more than 2% wt of total impurity after stored at about 15° C. to about 30° C. for 6, 9, 12, 18, or 24 months. In some embodiments, the liquid pharmaceutical composition contains no more than 2% wt of total impurity after stored at room temperature for 3 months. In some embodiments, the liquid pharmaceutical composition contains no more than 2% wt of total impurity after stored at room temperature for 6, 9, 12, 18, or 24 months. In some embodiments, the liquid pharmaceutical composition contains no more than 2% wt of total impurity after stored at ambient conditions for 3 months. In some embodiments, the liquid pharmaceutical composition contains no more than 2% wt of total impurity after stored at ambient conditions for 6, 9, 12, 18, or 24 months. In some embodiments, the liquid pharmaceutical composition contains no more than 2% wt of total impurity after stored at about 40° C.±2° C. for 1 months. In some embodiments, the liquid pharmaceutical composition contains no more than 2% wt of total impurity after stored at about 40° C.±2° C. for 2, 3, or 6 months. In some embodiments, the liquid pharmaceutical composition contains no more than 2% wt of total impurity after stored at accelerated conditions for 1 months. In some embodiments, the liquid pharmaceutical composition contains no more than 2% wt of total impurity after stored at accelerated conditions for 2, 3, or 6 months.

In some embodiments, the liquid pharmaceutical composition contains no more than 1% wt of total impurity after stored at about 2° C. to about 8° C. for 3, 6, 9, 12, 18, 24, 30, or 36 months. In some embodiments, the liquid pharmaceutical composition contains no more than 1% wt of total impurity after stored at refrigerated conditions for 3, 6, 9, 12, 18, 24, 30, or 36 months. In some embodiments, the liquid pharmaceutical composition contains no more than 1% wt of total impurity after stored at about 15° C. to about 25° C. for 3, 6, 9, 12, 18, or 24 months. In some embodiments, the liquid pharmaceutical composition contains no more than 1% wt of total impurity after stored at about 15° C. to about 25° C., with temperature excursions permitted up to 30° C., for 3, 6, 9, 12, 18, or 24 months. In some embodiments, the liquid pharmaceutical composition contains no more than 1% wt of total impurity after stored at about 15° C. to about 30° C. for 3, 6, 9, 12, 18, or 24 months. In some embodiments, the liquid pharmaceutical composition contains no more than 1% wt of total impurity after stored at room temperature for 3, 6, 9, 12, 18, or 24 months. In some embodiments, the liquid pharmaceutical composition contains no more than 1% wt of total impurity after stored at ambient conditions for 3, 6, 9, 12, 18, or 24 months. In some embodiments, the liquid pharmaceutical composition contains no more than 1% wt of total impurity after stored at about 40° C.±2° C. for 1, 2, 3, or 6 months. In some embodiments, the liquid pharmaceutical composition contains no more than 1% wt of total impurity after stored at accelerated conditions for 1, 2, 3, or 6 months. In some embodiments, the total impurity is determined according to High-performance liquid chromatography (HPLC) method (e.g., described in Example B). In some embodiments, the liquid pharmaceutical composition retains at least 95% wt of the initial hydrocortisone amount after stored at about 2° C. to about 8° C. for 3, 6, 9, 12, 18, 24, 30, or 36 months. In some embodiments, the liquid pharmaceutical composition retains at least 95% wt of the initial hydrocortisone amount after stored at refrigerated conditions for 3, 6, 9, 12, 18, 24, 30, or 36 months. In some embodiments, the liquid pharmaceutical composition retains at least 95% wt of the initial hydrocortisone amount after stored at about 15° C. to about 25° C. for 3 months. In some embodiments, the liquid pharmaceutical composition retains at least 95% wt of the initial hydrocortisone amount after stored at about 15° C. to about 25° C. for 6, 9, 12, 18, or 24 months. In some embodiments, the liquid pharmaceutical composition retains at least 95% wt of the initial hydrocortisone amount after stored at about 15° C. to about 25° C., with temperature excursions permitted up to 30° C., for 3 months. In some embodiments, the liquid pharmaceutical composition retains at least 95% wt of the initial hydrocortisone amount after stored at about 15° C. to about 25° C., with temperature excursions permitted up to 30° C., for 6, 9, 12, 18, or 24 months. In some embodiments, the liquid pharmaceutical composition retains at least 95% wt of the initial hydrocortisone amount after stored at about 15° C. to about 30° C. for 3 months. In some embodiments, the liquid pharmaceutical composition retains at least 95% wt of the initial hydrocortisone amount after stored at about 15° C. to about 30° C. for 6, 9, 12, 18, or 24 months. In some embodiments, the liquid pharmaceutical composition retains at least 95% wt of the initial hydrocortisone amount after stored at room temperature for 3 months. In some embodiments, the liquid pharmaceutical composition retains at least 95% wt of the initial hydrocortisone amount after stored at room temperature for 6, 9, 12, 18, or 24 months. In some embodiments, the liquid pharmaceutical composition retains at least 95% wt of the initial hydrocortisone amount after stored at ambient conditions for 3 months. In some embodiments, the liquid pharmaceutical composition retains at least 95% wt of the initial hydrocortisone amount after stored at ambient conditions for 6, 9, 12, 18, or 24 months. In some embodiments, the liquid pharmaceutical composition retains at least 95% wt of the initial hydrocortisone amount after stored at about 40° C.±2° C. for 1 month. In some embodiments, the liquid pharmaceutical composition retains at least 95% wt of the initial hydrocortisone amount after stored at about 40° C.±2° C. for 2, 3, or 6 months. In some embodiments, the liquid pharmaceutical composition retains at least 95% wt of the initial hydrocortisone amount after stored at accelerated conditions for 1 month. In some embodiments, the liquid pharmaceutical composition retains at least 95% wt of the initial hydrocortisone amount after stored at accelerated conditions for 2, 3, or 6 months. In some embodiments, the liquid pharmaceutical composition retains at least 98% wt of the initial hydrocortisone amount after stored at about 2° C. to about 8° C. for 3, 6, 9, 12, 18, 24, 30, or 36 months. In some embodiments, the liquid pharmaceutical composition retains at least 98% wt of the initial hydrocortisone amount after stored at refrigerated conditions for 3, 6, 9, 12, 18, 24, 30, or 36 months. In some embodiments, the liquid pharmaceutical composition retains at least 98% wt of the initial hydrocortisone amount after stored at about 15° C. to about 25° C., for 3, 6, 9, 12, 18, or 24 months. In some embodiments, the liquid pharmaceutical composition retains at least 98% wt of the initial hydrocortisone amount after stored at about 15° C. to about 25° C., with temperature excursions permitted up to 30° C., for 3, 6, 9, 12, 18, or 24 months. In some embodiments, the liquid pharmaceutical composition retains at least 98% wt of the initial hydrocortisone amount after stored at about 15° C. to about 30° C., for 3, 6, 9, 12, 18, or 24 months. In some embodiments, the liquid pharmaceutical composition retains at least 98% wt of the initial hydrocortisone amount after stored at room temperature for 3, 6, 9, 12, 18, or 24 months. In some embodiments, the liquid pharmaceutical composition retains at least 98% wt of the initial hydrocortisone amount after stored at ambient conditions for 3, 6, 9, 12, 18, or 24 months. In some embodiments, the liquid pharmaceutical composition retains at least 98% wt of the initial hydrocortisone amount after stored at about 40° C.±2° C. for 1, 2, 3, or 6 months. In some embodiments, the liquid pharmaceutical composition retains at least 98% wt of the initial hydrocortisone amount after stored at accelerated conditions for 1, 2, 3, or 6 months. In some embodiments, the hydrocortisone amount is determined according to HPLC method (e.g., described in Example B). In some embodiments, the liquid pharmaceutical composition remains stable after stored at about 2° C. to about 8° C. for at least 3, 6, 9, 12, 18, or 24 months. In some embodiments, the liquid pharmaceutical composition remains stable after stored at refrigerated conditions for at least 3, 6, 9, 12, 18, or 24 months. In some embodiments, the liquid pharmaceutical composition remains stable after stored at about 15° C. to about 25° C. for at least 3, 6, 9, 12, 18, or 24 months. In some embodiments, the liquid pharmaceutical composition remains stable after stored at about 15° C. to about 25° C., with temperature excursions permitted up to 30° C., for at least 3, 6, 9, 12, 18, or 24 months. In some embodiments, the liquid pharmaceutical composition remains stable after stored at about 15° C. to about 30° C. for at least 3, 6, 9, 12, 18, or 24 months. In some embodiments, the liquid pharmaceutical composition remains stable after stored at room temperature for at least 3, 6, 9, 12, 18, or 24 months. In some embodiments, the liquid pharmaceutical composition remains stable after stored at ambient conditions for at least 3, 6, 9, 12, 18, or 24 months. In some embodiments, the liquid pharmaceutical composition remains stable after stored at about 40° C.±2° C. for at least 1, 2, 3, or 6 months. In some embodiments, the liquid pharmaceutical composition remains stable after stored at accelerated conditions for at least 1, 2, 3, or 6 months. In some embodiments, the nonaqueous liquid carrier comprises propylene glycol, glycerin, polyethylene glycol (PEG), alcohol, or a combination thereof. In some embodiments, the nonaqueous liquid carrier comprises propylene glycol, glycerin, and PEG. In some embodiments, the PEG is PEG400. In some embodiments, the PEG has a number average molecular weight of about 350 to about 450 g/mol. In some embodiments, the PEG is present in the liquid pharmaceutical composition in an amount of about 30% to about 70% w/v. In some embodiments, the PEG is present in the liquid pharmaceutical composition in an amount of about 40% to about 60% w/v. In some embodiments, the PEG is present in the liquid pharmaceutical composition in an amount of about 45% to about 55% w/v. In some embodiments, the propylene glycol is present in the liquid pharmaceutical composition in an amount of about 0.5% to about 10% w/v. In some embodiments, the propylene glycol is present in the liquid pharmaceutical composition in an amount of about 4% to about 6% w/v. In some embodiments, the glycerin is present in the liquid pharmaceutical composition in an amount of about 40% to about 80% w/v. In some embodiments, the glycerin is present in the liquid pharmaceutical composition in an amount of about 50% to about 70% w/v. In some embodiments, the liquid pharmaceutical composition comprises a preservative. In some embodiments, the preservative comprises an antimicrobial agent, a chelating agent, an antioxidant, or a combination thereof. In some embodiments, the antimicrobial agent comprises a paraben or a mixture of parabens, benzoic acid or a pharmaceutically acceptable salt thereof, sorbic acid or a pharmaceutically acceptable salt thereof, phenoxyethanol, benzyl alcohol, propionic acid, or a combination thereof. In some embodiments, the mixture of parabens comprises methyl paraben, ethyl paraben, propyl paraben, or a combination thereof. In some embodiments, the chelating agent comprises disodium ethylenediaminetetraacetic acid, polyphosphates, citric acid, calcium disodium edetate, ethylenediaminetetraacetic acid (EDTA), or a combination thereof. In some embodiments, the antioxidant comprises vitamin A, monothioglycerol, ascorbic acid, sodium bisulfite, sodium sulfite, α-Tocopherol acetate (vitamin E), butylated hydroxyanisole (BHA), butylated hydroxytoluene (BHT), or a combination thereof. In some embodiments, the liquid pharmaceutical composition comprises a flavoring agent. In some embodiments, the flavoring agent comprises a natural flavoring agent, an artificial flavoring agent, or a combination thereof. In some embodiments, the flavoring agent comprises vanillin, grape flavor, caramel flavor, maltol, raspberry flavor, fruity flavor, or berry flavor. In some embodiments, the flavoring agent comprises 4-hydroxy-3-methoxybenzaldehyde, methyl anthranilate, 3,5-dimethyl-1,2-cyclopentadione, maltol, 4-(4-hydroxyphenyl)butan-2-one, ethyl maltol, or ethyl propionate. In some embodiments, the pharmaceutical composition comprises a sweetener. In some embodiments, the sweetener is a sugar (e.g., glucose, fructose, sucrose, lactose, maltose) or sugar alcohol (e.g., xylitol, mannitol, lactitol, maltitol, or sorbitol). In some embodiments, the sweetener is glucose, fructose, sucrose, xylitol, tagatose, sucralose, maltitol, isomaltulose, hydrogenated isomaltulose, lactitol, sorbitol, erythritol, trehalose, maltodextrin, or polydextrose. In some embodiments, the pharmaceutical composition comprises a) hydrocortisone or a pharmaceutically acceptable salt thereof in an amount of about 0.01% to about 2% weight by volume (w/v); b) a nonaqueous liquid carrier comprising propylene glycol, glycerin, PEG, or a combination thereof; c) a preservative comprising an antioxidant, an antimicrobial agent, or a combination thereof; d) optionally, a sweetener; and e) optionally, a flavoring agent. In some embodiments, the pharmaceutical composition comprises a) hydrocortisone or a pharmaceutically acceptable salt thereof in an amount of about 0.05% to about 0.5% weight by volume (w/v); b) a nonaqueous liquid carrier comprising propylene glycol, glycerin, and polyethylene glycol 400 (PEG 400), wherein the propylene glycol is present in an amount of about 2% to about 10% w/v, wherein the PEG 400 is present in an amount of about 20% to about 70% w/v, wherein the glycerin is present in an amount of about 40% to about 80% w/v; c) a preservative comprising an antioxidant and an antimicrobial agent, wherein the antioxidant comprises BHA, BHT, or a combination thereof, wherein the antimicrobial agent comprises parabens; d) optionally, a sweetener (e.g., sucralose); and e) optionally, a flavoring agent (e.g., a flavoring agent comprising berry flavor, maltol, ethyl maltol, or a combination thereof). In some embodiments, the liquid pharmaceutical composition comprises a) hydrocortisone or a pharmaceutically acceptable salt thereof in an amount of about 0.05% to about 0.5% weight by volume (w/v); b) a nonaqueous liquid carrier comprising propylene glycol, glycerin, and polyethylene glycol 400 (PEG 400), wherein the propylene glycol is present in an amount of about 3% to about 7% w/v, wherein the PEG 400 is present in an amount of about 30% to about 60% w/v, wherein the glycerin is present in an amount of about 60% to about 70% w/v; c) an antioxidant comprising BHA, BHT, or a combination thereof, wherein the antioxidant is present in an amount of about 0.005% to about 0.05% w/v; d) an antimicrobial agent comprising methyl paraben, propyl paraben, or a combination thereof, wherein the antimicrobial agent is present in an amount of about 0.05% w/v to about 0.5% w/v; e) optionally, a sweetener in an amount of about 0.05% to about 5% w/v; and f) optionally, a flavoring agent in an amount of about 0.05% to about 1% w/v. In some embodiments, the pharmaceutical composition comprises a) hydrocortisone or a pharmaceutically acceptable salt thereof in an amount of about 0.1% weight by volume (w/v); b) a nonaqueous liquid carrier comprising propylene glycol, glycerin, and polyethylene glycol 400 (PEG 400), wherein the propylene glycol is present in an amount of about 5% w/v, wherein the PEG 400 is present in an amount of about 50% w/v, wherein the glycerin is present in an amount of about 62.2% w/v; c) an antioxidant comprising BHA in an amount of about 0.01% w/v; d) an antimicrobial agent comprising methyl paraben and propyl paraben, wherein the methyl paraben is present in an amount of about 0.18% w/v, and wherein propyl paraben is present in an amount of about 0.02% w/v; and e) sucralose in an amount of about 1% w/v, berry flavor in an amount of about 0.2% w/v, and ethyl maltol in an amount of about 0.1% to about 0.2% w/v.

Disclosed herein is a method of treating a disease or condition, comprising administering the liquid pharmaceutical composition described herein to a subject in need thereof. In some embodiments, the liquid pharmaceutical composition is administered to the subject orally or through a nasogastric, jejunostomy, or gastrostomy tube. In some embodiments, the disease or condition is selected from endocrine disorders, rheumatic disorders, collagen diseases, dermatologic diseases, allergic states, ophthalmic diseases, respiratory diseases, hematologic disorders, neoplastic diseases, edematous states, gastrointestinal diseases, tuberculous meningitis with subarachnoid block or impending block when used concurrently with appropriate anti-tuberculous chemotherapy, and trichinosis with neurologic or myocardial involvement. In some embodiments, the endocrine disorders comprise primary or secondary adrenocortical insufficiency, congenital adrenal hyperplasia, non-suppurative thyroiditis, or hypercalcemia associated with cancer. In some embodiments, the rheumatic disorders comprise psoriatic arthritis, rheumatoid arthritis, including juvenile rheumatoid arthritis, ankylosing spondylitis, acute and subacute bursitis, acute nonspecific tenosynovitis, acute gouty arthritis, post-traumatic osteoarthritis, synovitis of osteoarthritis, or epicondylitis. In some embodiments, the liquid pharmaceutical composition is used to treat rheumatic disorders as an adjunctive therapy for short-term administration to tide the subject over an acute episode or exacerbation. In some embodiments, the collagen diseases comprise systemic lupus erythematosus, systemic dermatomyositis (polymyositis), or acute rheumatic carditis. In some embodiments, the liquid pharmaceutical composition is used to treat collagen diseases during an exacerbation or as a maintenance therapy. In some embodiments, the dermatologic diseases comprise pemphigus, bullous dermatitis herpetiformis, severe erythema multiforme (Stevens-Johnson syndrome), exfoliative dermatitis, mycosis fungoides, severe psoriasis, or severe seborrheic dermatitis. In some embodiments, the allergic states comprise seasonal or perennial allergic rhinitis, serum sickness, bronchial asthma, contact dermatitis, atopic dermatitis, or drug hypersensitivity reactions. In some embodiments, the liquid pharmaceutical composition is used to treat allergic states for control of severe or incapacitating allergic conditions intractable to adequate trials of conventional treatment. In some embodiments, the ophthalmic diseases comprise allergic conjunctivitis, keratitis, allergic corneal marginal ulcers, herpes zoster ophthalmicus, iritis and iridocyclitis, chorioretinitis, anterior segment inflammation, diffuse posterior uveitis and choroiditis, optic neuritis, or sympathetic ophthalmia. In some embodiments, the respiratory diseases comprise symptomatic sarcoidosis, Loeffler's syndrome, berylliosis, fulminating or disseminated pulmonary tuberculosis when used concurrently with appropriate anti-tuberculous chemotherapy, or aspiration pneumonitis. In some embodiments, the hematologic disorders comprise idiopathic thrombocytopenic purpura in adults, secondary thrombocytopenia in adults, acquired (autoimmune) hemolytic anemia, erythroblastopenia (RBC anemia), or congenital (erythroid) hypoplastic anemia. In some embodiments, the neoplastic diseases comprise leukemias and lymphomas in adults, or acute leukemia of childhood. In some embodiments, the liquid pharmaceutical composition is used to treat neoplastic diseases for palliative management. In some embodiments, the edematous states comprise proteinuria in nephrotic syndrome. In some embodiments, the liquid pharmaceutical composition is used to induce a diuresis or remission of proteinuria in the nephrotic syndrome, without uremia, of the idiopathic type or that due to lupus erythematosus. In some embodiments, the gastrointestinal diseases comprise ulcerative colitis or regional enteritis. In some embodiments, the liquid pharmaceutical composition is used to tide the subject over a critical period of the gastrointestinal diseases. In some embodiments, the disease or condition is adrenal insufficiency. In some embodiments, the disease or condition is pediatric adrenal insufficiency. In some embodiments, the disease or condition is adrenal insufficiency in subjects who are not older than 17 years in age. In some embodiments, the liquid pharmaceutical composition is administered in a therapeutically effective amount. In some embodiments, the subject is human. In some embodiments, the subject is an adult. In some embodiments, the subject is not older than 17 years in age. In some embodiments, the subject is an elderly.

Disclosed herein is a method of making the liquid pharmaceutical composition described herein, wherein the method comprises mixing hydrocortisone or a pharmaceutically acceptable salt thereof with a nonaqueous liquid carrier, thereby forming a solution of hydrocortisone in the nonaqueous liquid carrier. In some embodiments, the method comprises adding a preservative, optionally a sweeter, and optionally a flavoring agent into the solution of hydrocortisone. In some embodiments, the preservative, optionally the sweeter, and optionally the flavoring agent is added to the nonaqueous liquid carrier before mixing hydrocortisone or a pharmaceutically acceptable salt thereof with the nonaqueous liquid carrier. In some embodiments, the method comprises optionally filtering the solution of hydrocortisone over a filter into a container. In some embodiments, the filter is a 5 m disposable filter.

Disclosed herein is a kit comprising a package enclosing the liquid pharmaceutical composition described herein. In some embodiments, the kit comprises instructions for use of the liquid pharmaceutical composition. In some embodiments, the package is a bottle. In some embodiments, the bottle has a light protection mechanism.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Hydrocortisone has a molecular weight of 362.46, and its chemical name is pregn-4-ene-3,20-dione,11,17,21-trihydroxy-, (11β)-. Hydrocortisone USP is crystalline powder that is white to practically white, odorless, and with a melting point of about 215° C. It is very slightly soluble in water and sparingly soluble in acetone and in alcohol. Its molecular weight is 362.46 and the structural formula is as follows:

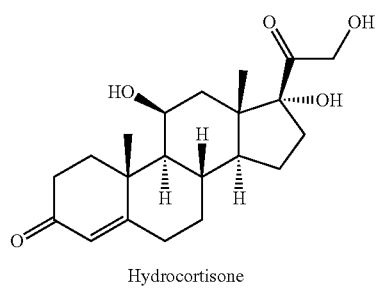

Hydrocortisone

In addition to the endocrine disorders such as adrenocortical insufficiency, hydrocortisone tablets have been used for rheumatic disorders, collagen diseases, dermatologic diseases, allergic states, ophthalmic diseases, respiratory diseases, hematologic disorders, neoplastic diseases, edematous states, gastrointestinal diseases and other indications.

Many patients are unable to swallow a solid dosage form, which requires these medications to be administered in an oral liquid form. The populations unable to swallow solid dosage forms are in need of liquid formulations include pediatric patients, older patients with dysphagia, ICU patients and patients on enteral nutrition. In addition, the patient populations would benefit from a liquid formulation with a longer shelf-life that can be left at room temperature without a need to store the medication in refrigerated condition.

In one aspect, provided herein are hydrocortisone oral liquid formulations. These hydrocortisone formulations described herein are useful for the treatment of endocrine disorders, rheumatic disorders, collagen diseases, dermatologic diseases, allergic states, ophthalmic diseases, respiratory diseases, hematologic disorders, neoplastic diseases, edematous states, gastrointestinal diseases, tuberculous meningitis with subarachnoid block or impending block when used concurrently with appropriate anti-tuberculous chemotherapy, trichinosis with neurologic or myocardial involvement, etc. The formulations can be advantageous over conventional solid dosage administration of hydrocortisone in many aspects, including ease of administration, accuracy of dosing, accessibility to additional patient populations such as to children and the elderly, and an increased patient compliance to medication.

It is generally known that certain segments of the population have difficulty ingesting and swallowing solid oral dosage forms such as tablets and capsules. As many as a quarter of the total population has this difficulty. Often, this leads to non-compliance with the recommended medical therapy with the solid dosage forms, thereby resulting in rending the therapy ineffective. Further, solid dosage forms are not recommended for children or elderly due to increased risk in choking.

Furthermore, the dose of hydrocortisone to be given to children is calculated according to the child's weight. When the calculated dose is something other than the amount present in one or more intact solid dosage forms, the solid dosage form must be divided to provide the correct dose. This leads to inaccurate dosing when solid dosages forms, such as tablets, are compounded to prepare other formulations for children.

For hydrocortisone, the current method of making a liquid formulation is for a compounding pharmacist to crush the hydrocortisone tablets into powder via mortar and pestle and reconstitute the powder in some liquid form, such as an oral suspension. However, forming a hydrocortisone oral liquid in this fashion has significant drawbacks including large variability in the actual dosage, incomplete solubilizing of the hydrocortisone tablet in the liquid, rapid instability, inconsistent formulation methods per compounding pharmacy, and a number of other potential issues. The crushed tablet liquid formulation may also be potentially unsafe due to contamination with residual drugs and other substances from the mortar and pestle or other crushing agents. In addition, such crushed tablet liquid formulations generally have a short in-use stability that is limited to 60 days or at most 90 days after opening even when the formulations are stored under refrigerated condition.

The present embodiments provide a safe and effective oral administration of hydrocortisone for the treatment of adrenocortical deficiency and other disorders. In particular, the embodiments provide stable hydrocortisone oral liquid formulations. The present embodiments also provide hydrocortisone oral liquid formulations as ready-to-use liquid preparations. As used herein, the term "ready-to-use" is intended to mean that the composition is administered to the patient without dilution, and/or without the addition of any further components to the composition.

In some embodiments, the hydrocortisone used in the formulations described herein is a hydrocortisone free base. In some embodiments, the hydrocortisone used in the formulations described herein is a hydrocortisone salt. In some instances, the hydrocortisone salt is hydrocortisone acetate. In some instances, the hydrocortisone salt is hydrocortisone sodium succinate. In some instances, the hydrocortisone salt is hydrocortisone sodium phosphate. In other instances, the hydrocortisone salt is in the form of hydrocortisone acetate or hydrocortisone sodium succinate.

Hydrocortisone Oral Liquid Formulations

Oral liquids include, but are not limited to, solutions (both aqueous and nonaqueous), suspensions, emulsions, syrups, slurries, juices, elixirs, dispersions, and the like. It is envisioned that solution/suspensions are also included where certain components described herein are in a solution.

In one aspect, the hydrocortisone liquid formulations described herein comprise hydrocortisone or a pharmaceutically acceptable salt thereof and a liquid carrier. In some embodiments, the liquid carrier is a nonaqueous liquid carrier. In some embodiments, the liquid carrier is an aqueous liquid carrier. In some embodiments, the liquid pharmaceutical composition is an oral solution. In some embodiments, the liquid pharmaceutical composition contains less than 5% wt of water.

In some embodiments, the liquid pharmaceutical composition contains water. In some embodiments, the liquid pharmaceutical composition contains less than 20% wt, less than 15% wt, less than 10% wt, less than 9% wt, less than 8% wt, less than 7% wt, less than 6% wt, less than 5% wt, less than 4% wt, less than 3% wt, less than 2% wt, or less than 1% wt of water. In some embodiments, the liquid pharmaceutical composition contains less than 5% wt of water. In some embodiments, the liquid pharmaceutical composition contains less than 4% wt of water. In some embodiments, the liquid pharmaceutical composition contains less than 3% wt of water. In some embodiments, the liquid pharmaceutical composition contains less than 2% wt of water. In some embodiments, the liquid pharmaceutical composition contains less than 1% wt of water. In some embodiments, the liquid pharmaceutical composition contains less than 0.5% wt of water. In some embodiments, the liquid pharmaceutical composition contains less than 0.1% wt of water. In some embodiments, the liquid pharmaceutical composition contains less than 0.01% wt of water. In some embodiments, the liquid pharmaceutical composition contains no water. In some embodiments, the liquid pharmaceutical composition is nonaqueous.

In some embodiments, liquid formulations described herein comprise hydrocortisone or a pharmaceutically acceptable salt thereof. In some embodiments, hydrocortisone or a pharmaceutically acceptable salt thereof, is present in the oral liquid formulation in an amount of about 0.8 to about 1.2 mg/ml. In other embodiments, hydrocortisone or a pharmaceutically acceptable salt thereof, is present in about 0.8 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/ml, about 0.91 mg/ml, about 0.92 mg/ml, about 0.93 mg/ml, about 0.94 mg/ml, about 0.95 mg/ml, about 0.96 mg/ml, about 0.97 mg/ml, about 0.98 mg/ml, about 0.99 mg/ml, about 1 mg/ml, about 1.01 mg/ml, about 1.02, mg/ml, about 1.03 mg/ml, about 1.04 mg/ml, about 1.05 mg/ml, about 1.06 mg/ml, about 1.07 mg/ml, about 1.08 mg/ml, about 1.09 mg/ml, about 1.1 mg/ml, about 1.11 mg/ml, about 1.12, mg/ml, about 1.13 mg/ml, about 1.14 mg/ml, about 1.15 mg/ml, about 1.16 mg/ml, about 1.17 mg/ml, about 1.18 mg/ml, about 1.19 mg/ml, or about 1.2 mg/ml in the liquid oral formulation. In some embodiments, hydrocortisone is present in about 1 mg/ml in the oral liquid formulation. In some embodiments, hydrocortisone or a pharmaceutically acceptable salt thereof, is present in the oral liquid formulation in an amount of about 0.1 to about 10 mg/ml. In some embodiments, hydrocortisone or a pharmaceutically acceptable salt thereof, is present in the oral liquid formulation in an amount of about 0.5 to about 5 mg/ml. In some embodiments, hydrocortisone or a pharmaceutically acceptable salt thereof, is present in the oral liquid formulation in an amount of about 5 to about 10 mg/ml. In some embodiments, hydrocortisone or a pharmaceutically acceptable salt thereof, is present in the oral liquid formulation in an amount of about 1 to about 5 mg/ml. In some embodiments, hydrocortisone or a pharmaceutically acceptable salt thereof, is present in the oral liquid formulation in an amount of about 1 to about 3 mg/ml. In some embodiments, hydrocortisone or a pharmaceutically acceptable salt thereof, is present in the oral liquid formulation in an amount of about 2 to about 5 mg/ml. In some embodiments, hydrocortisone is present in about 2 mg/ml in the oral liquid formulation. In some embodiments, hydrocortisone is present in about 5 mg/ml in the oral liquid formulation.

In some embodiments, hydrocortisone or a pharmaceutically acceptable salt thereof, is present in the liquid pharmaceutical composition in an amount of about 0.01% w/v to about 30% w/v. In some embodiments, hydrocortisone or a pharmaceutically acceptable salt thereof, is present in the liquid pharmaceutical composition in an amount of about 0.01% w/v to about 10% w/v. In some embodiments, hydrocortisone or a pharmaceutically acceptable salt thereof, is present in the liquid pharmaceutical composition in an amount of about 0.05% w/v to about 5% w/v. In some embodiments, hydrocortisone or a pharmaceutically acceptable salt thereof, is present in the liquid pharmaceutical composition in an amount of about 0.05% w/v to about 1% w/v. In some embodiments, hydrocortisone or a pharmaceutically acceptable salt thereof, is present in the liquid pharmaceutical composition in an amount of about 0.05% w/v to about 0.5% w/v. In other embodiments, hydrocortisone or a pharmaceutically acceptable salt thereof, is present in the liquid pharmaceutical composition in an amount of about 0.01% w/v to about 0.05% w/v, about 0.05% w/v to about 0.1% w/v, about 0.1% w/v to about 0.5% w/v, about 0.5% w/v to about 1% w/v, about 1% w/v to about 2% w/v, about 2% w/v to about 5% w/v, about 5% w/v to about 10% w/v, about 10% w/v to about 20% w/v, or about 20% w/v to about 30% w/v. In some embodiments, hydrocortisone or a pharmaceutically acceptable salt thereof, is present in the liquid pharmaceutical composition in an amount of about 0.1% w/v. In some embodiments, hydrocortisone or a pharmaceutically acceptable salt thereof, is present in the liquid pharmaceutical composition in an amount of about 0.2% w/v. In some embodiments, hydrocortisone or a pharmaceutically acceptable salt thereof, is present in the liquid pharmaceutical composition in an amount of about 0.5% w/v.

In some embodiments, hydrocortisone or a pharmaceutically acceptable salt thereof, is present in the liquid pharmaceutical composition in an amount of about 0.01% wt to about 30% wt. In some embodiments, hydrocortisone or a pharmaceutically acceptable salt thereof, is present in the liquid pharmaceutical composition in an amount of about 0.01% wt to about 10% wt. In some embodiments, hydrocortisone or a pharmaceutically acceptable salt thereof, is present in the liquid pharmaceutical composition in an amount of about 0.05% wt to about 5% wt. In some embodiments, hydrocortisone or a pharmaceutically acceptable salt thereof, is present in the liquid pharmaceutical composition in an amount of about 0.05% wt to about 1% wt. In some embodiments, hydrocortisone or a pharmaceutically acceptable salt thereof, is present in the liquid pharmaceutical composition in an amount of about 0.05% wt to about 0.5% wt. In other embodiments, hydrocortisone or a pharmaceutically acceptable salt thereof, is present in the liquid pharmaceutical composition in an amount of about 0.01% wt to about 0.05% wt, about 0.05% wt to about 0.1% wt, about 0.1% wt to about 0.5% wt, about 0.5% wt to about 1% wt, about 1% wt to about 2% wt, about 2% wt to about 5% wt, about 5% wt to about 10% wt, about 10% wt to about 20% wt, or about 20% wt to about 30% wt. In some embodiments, hydrocortisone or a pharmaceutically acceptable salt thereof, is present in the liquid pharmaceutical composition in an amount of about 0.083% wt. In some embodiments, hydrocortisone or a pharmaceutically acceptable salt thereof, is present in the liquid pharmaceutical composition in an amount of about 0.166% wt. In some embodiments, hydrocortisone or a pharmaceutically acceptable salt thereof, is present in the liquid pharmaceutical composition in an amount of about 0.415% wt.

In one aspect, disclosed herein are liquid pharmaceutical compositions comprising hydrocortisone or a pharmaceutically acceptable salt thereof, a nonaqueous liquid carrier, and a preservative. In some embodiments, hydrocortisone or a pharmaceutically acceptable salt thereof is present in an amount of about 0.01% to about 10% weight by volume (w/v). In some embodiments, hydrocortisone or a pharmaceutically acceptable salt thereof is present in an amount of about 0.01% to about 10% w/v, about 0.01% to about 8%, about 0.01% to about 5%, about 0.01% to about 2% w/v. In some embodiments, hydrocortisone or a pharmaceutically acceptable salt thereof is present in an amount of about 0.01% to about 2% w/v. In some embodiments, the nonaqueous liquid carrier comprises propylene glycol. In some embodiments, the nonaqueous liquid carrier comprises glycerin. In some embodiments, the nonaqueous liquid carrier comprises PEG. In some embodiments, the nonaqueous liquid carrier comprises propylene glycol, glycerin, PEG, or a combination thereof. In some embodiments, the PEG is PEG 400. In some embodiments, the nonaqueous liquid carrier comprises propylene glycol, glycerin, and PEG 400. In some embodiments, the preservative comprises an antioxidant. In some embodiments, the preservative comprises an antimicrobial agent. In some embodiments, the preservative comprises an antioxidant, an antimicrobial agent, or a combination thereof. In some embodiments, the preservative comprises an antioxidant and an antimicrobial agent. In some embodiments, the liquid pharmaceutical compositions further comprise optionally, a sweetener. In some embodiments, the liquid pharmaceutical compositions further comprise optionally, a flavoring agent. In some embodiments, the liquid pharmaceutical compositions described herein comprises hydrocortisone or a pharmaceutically acceptable salt thereof in an amount of about 0.01% to about 2% w/v, a nonaqueous liquid carrier comprising propylene glycol, glycerin, PEG, or a combination thereof, a preservative comprising an antioxidant, an antimicrobial agent, or a combination thereof, optionally, a sweetener, and optionally, a flavoring agent.

In some embodiments, liquid pharmaceutical compositions described herein comprise hydrocortisone or a pharmaceutically acceptable salt thereof in an amount of about 0.05% to about 0.5% w/v. In some embodiments, the liquid pharmaceutical compositions comprise a nonaqueous liquid carrier.

In some cases, the nonaqueous liquid carrier is present in the liquid pharmaceutical compositions in an amount of about 70% to about 99% wt. In some embodiments, the nonaqueous liquid carrier comprises propylene glycol, glycerin, and PEG 400. In some embodiments, the propylene glycol is present in the liquid pharmaceutical compositions in an amount of about 2% to about 10% w/v. In some embodiments, the propylene glycol is present in the liquid pharmaceutical compositions in an amount of about 3% to about 7% w/v. In some embodiments, the PEG 400 is present in the liquid pharmaceutical compositions in an amount of about 20% to about 70% w/v. In some embodiments, the PEG 400 is present in the liquid pharmaceutical compositions in an amount of about 30% to about 60% w/v. In some embodiments, the glycerin is present in the liquid pharmaceutical compositions in an amount of about 40% to about 80% w/v. In some embodiments, the glycerin is present in the liquid pharmaceutical compositions in an amount of about 50% to about 70% w/v. In some embodiments, the liquid pharmaceutical compositions comprise a preservative. In some embodiments, the preservative comprises an antioxidant and an antimicrobial agent. In some embodiments, the antioxidant is present in the liquid pharmaceutical composition in an amount of about 0.005% to about 0.05% w/v. In some embodiments, the antioxidant comprises BHA, BHT, or a combination thereof. In some embodiments, the antioxidant comprises BHA. In some embodiments, the antimicrobial agent is present in the liquid pharmaceutical composition in an amount of about 0.05% to about 0.5% w/v. In some embodiments, the antimicrobial agent comprises parabens. In some embodiments, the parabens comprise methyl paraben, propyl paraben, or a combination thereof. In some embodiments, the liquid pharmaceutical compositions comprise optionally a sweetener, such as sucralose. In some embodiments, the liquid pharmaceutical compositions comprise optionally a flavoring agent, for example, berry flavor, maltol, ethyl maltol, or a combination thereof.

In some embodiments, liquid pharmaceutical compositions described herein comprise hydrocortisone or a pharmaceutically acceptable salt thereof in an amount of about 0.1% w/v. In some embodiments, the liquid pharmaceutical compositions comprise a nonaqueous liquid carrier. In some embodiments, the nonaqueous liquid carrier comprises propylene glycol, glycerin, and PEG 400. In some cases, the nonaqueous liquid carrier is present in the liquid pharmaceutical compositions in an amount of about 98.6% wt. In some embodiments, the propylene glycol is present in the liquid pharmaceutical compositions in an amount of about 5% w/v. In some embodiments, the PEG 400 is present in the liquid pharmaceutical compositions in an amount of about 50% w/v. In some embodiments, the glycerin is present in the liquid pharmaceutical compositions in an amount of about 62.2% w/v. In some embodiments, the liquid pharmaceutical compositions comprise a preservative. In some embodiments, the preservative comprises an antioxidant and an antimicrobial agent. In some embodiments, the antioxidant is present in the liquid pharmaceutical composition in an amount of about 0.01% w/v. In some embodiments, the antioxidant is BHA. In some embodiments, the BHA is present in the liquid pharmaceutical composition in an amount of about 0.01% w/v. In some embodiments, the antimicrobial agent is present in the liquid pharmaceutical composition in an amount of about 0.2% w/v. In some embodiments, the antimicrobial agent comprises methyl paraben and propyl paraben. In some embodiments, the antimicrobial agent is present in the liquid pharmaceutical composition in an amount of about 0.2% w/v. In some embodiments, the methyl paraben is present in the liquid pharmaceutical composition in an amount of about 0.18% w/v. In some embodiments, the propyl paraben is present in the liquid pharmaceutical composition in an amount of about 0.02% w/v. In some embodiments, the liquid pharmaceutical compositions comprise a sweetener. In some embodiments, the sweetener is present in the liquid pharmaceutical composition in an amount of about 1% w/v. In some embodiments, the sweetener is sucralose. In some embodiments, the sucralose is present in the liquid pharmaceutical composition in an amount of about 1% w/v. In some embodiments, the liquid pharmaceutical compositions comprise a flavoring agent. In some embodiments, the flavoring agent is present in the liquid pharmaceutical composition in an amount of about 0.3% to about 0.4% w/v. In some embodiments, the flavoring agent is present in the liquid pharmaceutical composition in an amount of about 0.4% w/v. In some embodiments, the flavoring agent comprises berry flavor and ethyl maltol. In some embodiments, the sucralose is present in the liquid pharmaceutical composition in an amount of about 1% w/v. In some embodiments, the berry flavor is present in the liquid pharmaceutical composition in an amount of about 0.2% w/v. In some embodiments, the ethyl maltol is present in the liquid pharmaceutical composition in an amount of about 0.1% w/v. In some embodiments, the ethyl maltol is present in the liquid pharmaceutical composition in an amount of about 0.2% w/v. In some embodiments, the liquid pharmaceutical compositions described herein are ready-to-use. In some embodiments, the liquid pharmaceutical compositions described herein do not contain monothioglycerol. In some embodiments, the liquid pharmaceutical compositions described herein do not contain monobasic sodium phosphate.

In some embodiments, the liquid pharmaceutical compositions described herein do not contain dibasic sodium phosphate. In some embodiments, the liquid pharmaceutical compositions described herein do not contain disodium EDTA. In some embodiments, the liquid pharmaceutical compositions described herein do not contain a buffer. In some embodiments, the liquid pharmaceutical compositions described herein do not contain a buffering agent. In some embodiments, the liquid pharmaceutical compositions described herein do not contain sodium citrate. In some embodiments, the liquid pharmaceutical compositions described herein do not contain a propellant. In some embodiments, the liquid pharmaceutical compositions described herein do not contain an organic acid. In some embodiments, the liquid pharmaceutical compositions described herein do not contain citric acid. In some embodiments, the liquid pharmaceutical compositions described herein do not contain tartaric acid. In some embodiments, the liquid pharmaceutical compositions described herein do not contain a surfactant.

Stability

In some embodiments, hydrocortisone oral liquid formulations described herein are stable or shelf-stable in various storage conditions including refrigerated conditions, ambient conditions, room temperature, and accelerated conditions. Stable or shelf stable as used herein refer to hydrocortisone oral liquid formulations having about 95% or greater of the initial hydrocortisone amount and about 5% wt or less total impurities or related substances at the end of a given storage period. Alternatively, stable or shelf stable as used herein refer to hydrocortisone oral liquid formulations having about 90% wt or greater of initial hydrocortisone amount and about 10% wt or less total impurities or related substances at the end of a given storage period. In some embodiments, the hydrocortisone oral liquid formulations are stored in an unopened container, such as an unopened bottle.

The percentage of impurities can be calculated from the amount of impurities relative to the amount of hydrocortisone. The percentage of impurities can be assessed by HPLC, such as using the United States Pharmacopeia (USP) method for hydrocortisone, the HPLC method described in Example B, or any other known testing method. In some embodiments, a stable hydrocortisone liquid pharmaceutical composition contains no more than about 10% wt, about 5% wt, about 4% wt, about 3% wt, about 2.5% wt, about 2% wt, about 1.5% wt, about 1% wt, or about 0.5% wt total impurities or related substances. In other embodiments, a stable hydrocortisone liquid pharmaceutical composition contains no more than about 10% wt total impurities or related substances. In other embodiments, a stable hydrocortisone liquid pharmaceutical composition contains no more than about 5% wt total impurities or related substances. In yet other embodiments, a stable hydrocortisone liquid pharmaceutical composition contains no more than about 4% wt total impurities or related substances. In yet other embodiments, a stable hydrocortisone liquid pharmaceutical composition contains no more than about 3% wt total impurities or related substances. In yet other embodiments, a stable hydrocortisone liquid pharmaceutical composition contains no more than about 2% wt total impurities or related substances. In yet other embodiments, a stable hydrocortisone liquid pharmaceutical composition contains no more than about 1% wt total impurities or related substances.

In some embodiments, a stable hydrocortisone liquid pharmaceutical composition contains no more than about 0.5% wt, about 0.4% wt, about 0.3% wt, about 0.2% wt, or about 0.1% wt of a single impurity. In some embodiments, a stable hydrocortisone liquid pharmaceutical composition contains no more than about 0.5% wt of a single impurity. In some embodiments, a stable hydrocortisone liquid pharmaceutical composition contains no more than about 0.4% wt of a single impurity. In some embodiments, a stable hydrocortisone liquid pharmaceutical composition contains no more than about 0.3% wt of a single impurity. In some embodiments, a stable hydrocortisone liquid pharmaceutical composition contains no more than about 0.2% wt of a single impurity. In some embodiments, a stable hydrocortisone liquid pharmaceutical composition contains no more than about 0.1% wt of a single impurity. In some embodiments, the single impurity is a unknown impurity. In some embodiments, the single impurity is a known impurity. In some embodiments, the single impurity is a process impurity. In some cases, the single impurity is 11β,17-Dihydroxy-3,20-dioxopregn-4-en-21-yl acetate, also termed "H. acetate" in the present application. In some embodiments, H. acetate is characterized as having an RRT of 1.79 when measured using the HPLC method described in Table B-3. In some embodiments, the single impurity is cortisol Impurity 1. In some embodiments, the single impurity is cortisone (17,21-Dihydroxy-pregn-4-ene-3,11,20-trione), also termed "Impurity B" (Imp B) in the present application. In some embodiments, Impurity B is characterized as having an RRT of 1.09 when measured using the HPLC method described in Table B-3. In some embodiments, the single impurity is Impurity E (Imp E). In some embodiments, the single impurity is 21-Aldehyde (11β,17-Dihydroxy-3,20-dioxopregn-4-en-21-al hydrate), also termed "Impurity G" (Imp G) in the present application. In some embodiments, Impurity G is characterized as having an RRT of 0.88 when measured using the HPLC method described in Table B-3. In some embodiments, the single impurity is Impurity h (Imp h). In some embodiments, the single impurity is Impurity D (Imp d). In some embodiments, the single impurity is Impurity N (Imp N). In some embodiments, the single impurity is characterized as having a relative retention time (RRT) of 0.226 when measured using the HPLC method described in Table B-3. In some embodiments, the single impurity is characterized as having a relative retention time (RRT) of 0.336 when measured using the HPLC method described in Table B-3. In some embodiments, the single impurity is characterized as having a relative retention time (RRT) of 0.373 when measured using the HPLC method described in Table B-3. In some embodiments, the single impurity is characterized as having a relative retention time (RRT) of 0.393 when measured using the HPLC method described in Table B-3. In some embodiments, the single impurity is characterized as having a relative retention time (RRT) of 0.452 when measured using the HPLC method described in Table B-3. In some embodiments, the single impurity is characterized as having a relative retention time (RRT) of 0.622 when measured using the HPLC method described in Table B-3. In some embodiments, the single impurity is characterized as having a relative retention time (RRT) of 0.71 when measured using the HPLC method described in Table B-3. In some embodiments, the single impurity is characterized as having a relative retention time (RRT) of 0.82 when measured using the HPLC method described in Table B-3. In some embodiments, the single impurity is characterized as having a relative retention time (RRT) of 0.836 when measured using the HPLC method described in Table B-3. In some embodiments, the single impurity is characterized as having a relative retention time (RRT) of 0.915 when measured using the HPLC method described in Table B-3. In some embodiments, the single impurity is characterized as having a relative retention time (RRT) of 0.932 when measured using the HPLC method described in Table B-3. In some embodiments, the single impurity is characterized as having a relative retention time (RRT) of 0.948 when measured using the HPLC method described in Table B-3. In some embodiments, the single impurity is characterized as having a relative retention time (RRT) of 1.064 when measured using the HPLC method described in Table B-3. In some embodiments, the single impurity is characterized as having a relative retention time (RRT) of 1.068 when measured using the HPLC method described in Table B-3. In some embodiments, the single impurity is characterized as having a relative retention time (RRT) of 1.071 when measured using the HPLC method described in Table B-3. In some embodiments, the single impurity is 4-Androsten-11-ol-3,17-dione, also termed "Keto" (U-03) in the present application. In some embodiments, Keto is characterized as having a relative retention time (RRT) of 1.51 when measured using the HPLC method described in Table B-3. In some embodiments, the single impurity is U-04. In some embodiments, the single impurity is characterized as having a relative retention time (RRT) of 1.091 when measured using the HPLC method described in Table B-3. In some embodiments, the single impurity is characterized as having a relative retention time (RRT) of 1.101 when measured using the HPLC method described in Table B-3. In some embodiments, the single impurity is characterized as having a relative retention time (RRT) of 1.131 when measured using the HPLC method described in Table B-3. In some embodiments, the single impurity is characterized as having a relative retention time (RRT) of 1.138 when measured using the HPLC method described in Table B-3. In some embodiments, the single impurity is characterized as having a relative retention time (RRT) of 1.182 when measured using the HPLC method described in Table B-3. In some embodiments, the single impurity is characterized as having a relative retention time (RRT) of 1.211 when measured using the HPLC method described in Table B-3. In some embodiments, the single impurity is characterized as having a relative retention time (RRT) of 1.215 when measured using the HPLC method described in Table B-3. In some embodiments, the single impurity is characterized as having a relative retention time (RRT) of 1.221 when measured using the HPLC method described in Table B-3. In some embodiments, the single impurity is characterized as having a relative retention time (RRT) of 1.233 when measured using the HPLC method described in Table B-3. In some embodiments, the single impurity is characterized as having a relative retention time (RRT) of 1.275 when measured using the HPLC method described in Table B-3. In some embodiments, the single impurity is characterized as having a relative retention time (RRT) of 1.279 when measured using the HPLC method described in Table B-3. In some embodiments, the single impurity is characterized as having a relative retention time (RRT) of 1.331 when measured using the HPLC method described in Table B-3. In some embodiments, the single impurity is characterized as having a relative retention time (RRT) of 1.341 when measured using the HPLC method described in Table B-3. In some embodiments, the single impurity is characterized as having a relative retention time (RRT) of 1.358 when measured using the HPLC method described in Table B-3. In some embodiments, the single impurity is characterized as having a relative retention time (RRT) of 1.366 when measured using the HPLC method described in Table B-3. In some embodiments, the single impurity is characterized as having a relative retention time (RRT) of 1.368 when measured using the HPLC method described in Table B-3. In some embodiments, the single impurity is Enol 1 (U-08). In some embodiments, Enol 1 (U-08) is characterized as having a relative retention time (RRT) of 1.432 when measured using the HPLC method described in Table B-3. In some embodiments, the single impurity is characterized as having a relative retention time (RRT) of 1.474 when measured using the HPLC method described in Table B-3. In some embodiments, the single impurity is (Z)-2-hydroxy-2-((8S,9S,10R,11S,13S,14S)-11-hydroxy-10,13-dimethyl-3-oxo-1,2,3,6,7,8,9,10,11,12,13,14,15,16-tetradecahydro-17H-cyclopenta[a]phenanthren-17-ylidene)acetaldehyde, also termed as "Enol 2" or "U-05" in the present application. In some embodiments, Enol 2 is characterized as having a relative retention time (RRT) of 2.33 when measured using the HPLC method described in Table B-3. In some embodiments, the single impurity is characterized as having a relative retention time (RRT) of 1.493 when measured using the HPLC method described in Table B-3. In some embodiments, the single impurity is characterized as having a relative retention time (RRT) of 1.527 when measured using the HPLC method described in Table B-3. In some embodiments, the single impurity is characterized as having a relative retention time (RRT) of 1.536 when measured using the HPLC method described in Table B-3. In some embodiments, the single impurity is characterized as having a relative retention time (RRT) of 1.592 when measured using the HPLC method described in Table B-3. In some embodiments, the single impurity is characterized as having a relative retention time (RRT) of 1.595 when measured using the HPLC method described in Table B-3. In some embodiments, the single impurity is characterized as having a relative retention time (RRT) of 1.598 when measured using the HPLC method described in Table B-3. In some embodiments, the single impurity is characterized as having a relative retention time (RRT) of 1.649 when measured using the HPLC method described in Table B-3. In some embodiments, the single impurity is 1-((10R,11S,13S,17R)-11,17-dihydroxy-10,13-dimethyl-3-oxo-2,3,4,5,6,7,10,11,12,13,14,15,16,17-tetradecahydro-1Hcyclopenta[a]phenanthrene-17-yl)-2,3-dihydroxy-4-((10R,11S,13S,17S)-11-hydroxy-10,13-dimethyl-3-oxo-2,3,6,7,8,9,10,11,12,13,14,15,16,17-tetradecahydro-1H-cyclopenta[a]phenanthrene-17-yl)butane-1,4-dione, also termed as "Asym dimer." In some embodiments, Asym dimer is characterized as having a relative retention time (RRT) of 2.94 when measured using the HPLC method described in Table B-3. In some embodiments, the single impurity is characterized as having a relative retention time (RRT) of 1.654 when measured using the HPLC method described in Table B-3. In some embodiments, the single impurity is characterized as having a relative retention time (RRT) of 1.674 when measured using the HPLC method described in Table B-3. In some embodiments, the single impurity is characterized as having a relative retention time (RRT) of 1.702 when measured using the HPLC method described in Table B-3. In some embodiments, the single impurity is characterized as having a relative retention time (RRT) of 1.802 when measured using the HPLC method described in Table B-3. In some embodiments, the single impurity is characterized as having a relative retention time (RRT) of 1.979 when measured using the HPLC method described in Table B-3. In some embodiments, the single impurity is characterized as having a relative retention time (RRT) of 2.62 when measured using the HPLC method described in Table B-3. In some embodiments, the single impurity is characterized as having a relative retention time (RRT) of 2.876 when measured using the HPLC method described in Table B-3. In some embodiments, the single impurity is characterized as having a relative retention time (RRT) of 2.912 when measured using the HPLC method described in Table B-3. In some embodiments, the single impurity is characterized as having a relative retention time (RRT) of 2.949 when measured using the HPLC method described in Table B-3. In some embodiments, the single impurity is characterized as having a relative retention time (RRT) of 2.952 when measured using the HPLC method described in Table B-3. In some embodiments, the single impurity is characterized as having a relative retention time (RRT) of 2.981 when measured using the HPLC method described in Table B-3. In some embodiments, the single impurity is characterized as having a relative retention time (RRT) of 3.026 when measured using the HPLC method described in Table B-3. In some embodiments, the single impurity is characterized as having a relative retention time (RRT) of 3.121 when measured using the HPLC method described in Table B-3. In some embodiments, the single impurity is characterized as having a relative retention time (RRT) of 3.157 when measured using the HPLC method described in Table B-3. In some embodiments, the single impurity is characterized as having a relative retention time (RRT) of 3.191 when measured using the HPLC method described in Table B-3.

In some embodiments, a stable hydrocortisone liquid pharmaceutical composition contains no more than about 0.5% wt of Keto. In some embodiments, a stable hydrocortisone liquid pharmaceutical composition contains no more than about 0.4% wt of Keto. In some embodiments, a stable hydrocortisone liquid pharmaceutical composition contains no more than about 0.3% wt of Keto. In some embodiments, a stable hydrocortisone liquid pharmaceutical composition contains no more than about 0.5% wt of Asym Dimer. In some embodiments, a stable hydrocortisone liquid pharmaceutical composition contains no more than about 0.2% wt of Asym Dimer. In some embodiments, a stable hydrocortisone liquid pharmaceutical composition contains no more than about 0.1% wt of Asym Dimer. In some embodiments, a stable hydrocortisone liquid pharmaceutical composition contains no more than about 0.5% wt of Enol 2. In some embodiments, a stable hydrocortisone liquid pharmaceutical composition contains no more than about 0.2% wt of Enol 2. In some embodiments, a stable hydrocortisone liquid pharmaceutical composition contains no more than about 0.1% wt of Enol 2. In some embodiments, a stable hydrocortisone liquid pharmaceutical composition contains no more than about 0.5% wt of Enol 1. In some embodiments, a stable hydrocortisone liquid pharmaceutical composition contains no more than about 0.2% wt of Enol 1. In some embodiments, a stable hydrocortisone liquid pharmaceutical composition contains no more than about 0.1% wt of Enol 1. In some embodiments, a stable hydrocortisone liquid pharmaceutical composition contains no more than about 0.5% wt of H. acetate. In some embodiments, a stable hydrocortisone liquid pharmaceutical composition contains no more than about 0.2% wt of H. acetate. In some embodiments, a stable hydrocortisone liquid pharmaceutical composition contains no more than about 0.1% wt of H. acetate. In some embodiments, a stable hydrocortisone liquid pharmaceutical composition contains no more than about 0.5% wt of Impurity G. In some embodiments, a stable hydrocortisone liquid pharmaceutical composition contains no more than about 0.2% wt of Impurity G. In some embodiments, a stable hydrocortisone liquid pharmaceutical composition contains no more than about 0.1% wt of Impurity G. In some embodiments, a stable hydrocortisone liquid pharmaceutical composition contains no more than about 0.5% wt of Impurity B. In some embodiments, a stable hydrocortisone liquid pharmaceutical composition contains no more than about 0.2% wt of Impurity B. In some embodiments, a stable hydrocortisone liquid pharmaceutical composition contains no more than about 0.1% wt of Impurity B. In some embodiments, a stable hydrocortisone liquid pharmaceutical composition contains no more than about 0.5% wt of Impurity H. In some embodiments, a stable hydrocortisone liquid pharmaceutical composition contains no more than about 0.2% wt of Impurity H. In some embodiments, a stable hydrocortisone liquid pharmaceutical composition contains no more than about 0.1% wt of Impurity H. In some embodiments, a stable hydrocortisone liquid pharmaceutical composition contains no more than about 0.2% wt of an impurity characterized as having a relative retention time (RRT) of 1.603 when measured using the HPLC method described in Table B-3. In some embodiments, a stable hydrocortisone liquid pharmaceutical composition contains no more than about 0.2% wt of an impurity characterized as having a relative retention time (RRT) of 1.550 when measured using the HPLC method described in Table B-3. In some embodiments, a stable hydrocortisone liquid pharmaceutical composition contains no more than about 0.1% wt of an impurity characterized as having a relative retention time (RRT) of 1.479 when measured using the HPLC method described in Table B-3. In some embodiments, a stable hydrocortisone liquid pharmaceutical composition contains no more than about 0.1% wt of an impurity characterized as having a relative retention time (RRT) of 1.592 when measured using the HPLC method described in Table B-3.

The percentage of hydrocortisone retained can be calculated from the amount of hydrocortisone in the composition at a certain time point relative to the initial amount of hydrocortisone. Assay or hydrocortisone content is assessed by HPLC, such as using the United States Pharmacopeia (USP) method for hydrocortisone, the HPLC method described in Example B, or any other known testing method. In some embodiments, a stable hydrocortisone liquid pharmaceutical composition retains at least about 90% wt, about 91% wt, about 92% wt, about 93% wt, about 94% wt, about 95% wt, about 96% wt, about 97% wt, about 98% wt, about 99% wt, about 99.5% wt, or about 99.9% wt of the initial hydrocortisone amount. In yet other embodiments, a stable hydrocortisone liquid pharmaceutical composition retains at least about 90% wt of the initial hydrocortisone amount. In yet other embodiments, a stable hydrocortisone liquid pharmaceutical composition retains at least about 91% wt of the initial hydrocortisone amount. In yet other embodiments, a stable hydrocortisone liquid pharmaceutical composition retains at least about 92% wt of the initial hydrocortisone amount. In yet other embodiments, a stable hydrocortisone liquid pharmaceutical composition retains at least about 93% wt of the initial hydrocortisone amount. In yet other embodiments, a stable hydrocortisone liquid pharmaceutical composition retains at least about 94% wt of the initial hydrocortisone amount. In yet other embodiments, a stable hydrocortisone liquid pharmaceutical composition retains at least about 95% wt of the initial hydrocortisone amount. In yet other embodiments, a stable hydrocortisone liquid pharmaceutical composition retains at least about 96% wt of the initial hydrocortisone amount. In yet other embodiments, a stable hydrocortisone liquid pharmaceutical composition retains at least about 97% wt of the initial hydrocortisone amount. In yet other embodiments, a stable hydrocortisone liquid pharmaceutical composition retains at least about 98% wt of the initial hydrocortisone amount. In yet other embodiments, a stable hydrocortisone liquid pharmaceutical composition retains at least about 99% wt of the initial hydrocortisone amount. In yet other embodiments, a stable hydrocortisone liquid pharmaceutical composition retains at least about 99.5% wt of the initial hydrocortisone amount. In yet other embodiments, a stable hydrocortisone liquid pharmaceutical composition retains at least about 99.8% wt of the initial hydrocortisone amount.

In some embodiments, hydrocortisone oral liquid formulations described herein are stable when stored at refrigerated conditions for at least 1 month, at least 2 months, at least 3 months, at least 6 months, at least 9 months, at least 12 months, at least 15 months, at least 18 months, at least 24 months, at least 30 months, or at least 36 months. In some embodiments, the hydrocortisone oral liquid formulations described herein are stable when stored at about 2° C. to about 8° C. for at least 1 month, at least 2 months, at least 3 months, at least 6 months, at least 9 months, at least 12 months, at least 15 months, at least 18 months, at least 24 months, at least 30 months, or at least 36 months.

In some embodiments, a hydrocortisone liquid pharmaceutical composition described herein contains no more than 2% wt of total impurity after stored at about 2° C. to about 8° C. for at least 3 months, at least 6 months, at least 9 months, at least 12 months, at least 15 months, at least 18 months, at least 24 months, at least 30 months, or at least 36 months. In some embodiments, the hydrocortisone liquid pharmaceutical composition contains no more than 2% wt of total impurity after stored at about 2° C. to about 8° C. for 3 months. In some embodiments, the hydrocortisone liquid pharmaceutical composition contains no more than 2% wt of total impurity after stored at about 2° C. to about 8° C. for 6 months. In some embodiments, the hydrocortisone liquid pharmaceutical composition contains no more than 2% wt of total impurity after stored at about 2° C. to about 8° C. for 9 months. In some embodiments, the hydrocortisone liquid pharmaceutical composition contains no more than 2% wt of total impurity after stored at about 2° C. to about 8° C. for 12 months. In some embodiments, the hydrocortisone liquid pharmaceutical composition contains no more than 2% wt of total impurity after stored at about 2° C. to about 8° C. for 15 months. In some embodiments, the hydrocortisone liquid pharmaceutical composition contains no more than 2% wt of total impurity after stored at about 2° C. to about 8° C. for 18 months. In some embodiments, the hydrocortisone liquid pharmaceutical composition contains no more than 2% wt of total impurity after stored at about 2° C. to about 8° C. for 24 months. In some embodiments, the hydrocortisone liquid pharmaceutical composition contains no more than 2% wt of total impurity after stored at about 2° C. to about 8° C. for 30 months. In some embodiments, the hydrocortisone liquid pharmaceutical composition contains no more than 2% wt of total impurity after stored at about 2° C. to about 8° C. for 36 months.

In some embodiments, a hydrocortisone liquid pharmaceutical composition contains no more than 1% wt of total impurity after stored at about 2° C. to about 8° C. for at least 3 months, at least 6 months, at least 9 months, at least 12 months, at least 15 months, at least 18 months, at least 24 months, at least 30 months, or at least 36 months. In some embodiments, the hydrocortisone liquid pharmaceutical composition contains no more than 1% wt of total impurity after stored at about 2° C. to about 8° C. for 3 months. In some embodiments, the hydrocortisone liquid pharmaceutical composition contains no more than 1% wt of total impurity after stored at about 2° C. to about 8° C. for 6 months. In some embodiments, the hydrocortisone liquid pharmaceutical composition contains no more than 1% wt of total impurity after stored at about 2° C. to about 8° C. for 9 months. In some embodiments, the hydrocortisone liquid pharmaceutical composition contains no more than 1% wt of total impurity after stored at about 2° C. to about 8° C. for 12 months. In some embodiments, the hydrocortisone liquid pharmaceutical composition contains no more than 1% wt of total impurity after stored at about 2° C. to about 8° C. for 15 months. In some embodiments, the hydrocortisone liquid pharmaceutical composition contains no more than 1% wt of total impurity after stored at about 2° C. to about 8° C. for 18 months. In some embodiments, the hydrocortisone liquid pharmaceutical composition contains no more than 1% wt of total impurity after stored at about 2° C. to about 8° C. for 24 months. In some embodiments, the hydrocortisone liquid pharmaceutical composition contains no more than 1% wt of total impurity after stored at about 2° C. to about 8° C. for 30 months. In some embodiments, the hydrocortisone liquid pharmaceutical composition contains no more than 1% wt of total impurity after stored at about 2° C. to about 8° C. for 36 months.

In some embodiments, a hydrocortisone liquid pharmaceutical composition described herein retains at least 95% wt of the initial hydrocortisone amount after stored at about 2° C. to about 8° C. for at least 3 months, at least 6 months, at least 9 months, at least 12 months, at least 15 months, at least 18 months, at least 24 months, at least 30 months, or at least 36 months. In some embodiments, the hydrocortisone liquid pharmaceutical composition retains at least 95% wt of the initial hydrocortisone amount after stored at about 2° C. to about 8° C. for 3 months. In some embodiments, the hydrocortisone liquid pharmaceutical composition retains at least 95% wt of the initial hydrocortisone amount after stored at about 2° C. to about 8° C. for 6 months. In some embodiments, the hydrocortisone liquid pharmaceutical composition retains at least 95% wt of the initial hydrocortisone amount after stored at about 2° C. to about 8° C. for 9 months. In some embodiments, the hydrocortisone liquid pharmaceutical composition retains at least 95% wt of the initial hydrocortisone amount after stored at about 2° C. to about 8° C. for 12 months. In some embodiments, the hydrocortisone liquid pharmaceutical composition retains at least 95% wt of the initial hydrocortisone amount after stored at about 2° C. to about 8° C. for 15 months. In some embodiments, the hydrocortisone liquid pharmaceutical composition retains at least 95% wt of the initial hydrocortisone amount after stored at about 2° C. to about 8° C. for 18 months. In some embodiments, the hydrocortisone liquid pharmaceutical composition retains at least 95% wt of the initial hydrocortisone amount after stored at about 2° C. to about 8° C. for 24 months. In some embodiments, the hydrocortisone liquid pharmaceutical composition retains at least 95% wt of the initial hydrocortisone amount after stored at about 2° C. to about 8° C. for 30 months. In some embodiments, the hydrocortisone liquid pharmaceutical composition retains at least 95% wt of the initial hydrocortisone amount after stored at about 2° C. to about 8° C. for 36 months.

In some embodiments, a hydrocortisone liquid pharmaceutical composition described herein at least 98% wt of the initial hydrocortisone amount after stored at about 2° C. to about 8° C. for at least 3 months, at least 6 months, at least 9 months, at least 12 months, at least 15 months, at least 18 months, at least 24 months, at least 30 months, or at least 36 months. In some embodiments, the hydrocortisone liquid pharmaceutical composition retains at least 98% wt of the initial hydrocortisone amount after stored at about 2° C. to about 8° C. for 3 months. In some embodiments, the hydrocortisone liquid pharmaceutical composition retains at least 98% wt of the initial hydrocortisone amount after stored at about 2° C. to about 8° C. for 6 months. In some embodiments, the hydrocortisone liquid pharmaceutical composition retains at least 98% wt of the initial hydrocortisone amount after stored at about 2° C. to about 8° C. for 9 months. In some embodiments, the hydrocortisone liquid pharmaceutical composition retains at least 98% wt of the initial hydrocortisone amount after stored at about 2° C. to about 8° C. for 12 months. In some embodiments, the hydrocortisone liquid pharmaceutical composition retains at least 98% wt of the initial hydrocortisone amount after stored at about 2° C. to about 8° C. for 15 months. In some embodiments, the hydrocortisone liquid pharmaceutical composition retains at least 98% wt of the initial hydrocortisone amount after stored at about 2° C. to about 8° C. for 18 months. In some embodiments, the hydrocortisone liquid pharmaceutical composition retains at least 98% wt of the initial hydrocortisone amount after stored at about 2° C. to about 8° C. for 24 months. In some embodiments, the hydrocortisone liquid pharmaceutical composition retains at least 98% wt of the initial hydrocortisone amount after stored at about 2° C. to about 8° C. for 30 months. In some embodiments, the hydrocortisone liquid pharmaceutical composition retains at least 98% wt of the initial hydrocortisone amount after stored at about 2° C. to about 8° C. for 36 months.

In some embodiments, a hydrocortisone liquid pharmaceutical composition described herein contains no more than 2% wt of total impurity after stored at refrigerated conditions for at least 3 months, at least 6 months, at least 9 months, at least 12 months, at least 15 months, at least 18 months, at least 24 months, at least 30 months, or at least 36 months. In some embodiments, the hydrocortisone liquid pharmaceutical composition contains no more than 2% wt of total impurity after stored at refrigerated conditions for 3 months. In some embodiments, the hydrocortisone liquid pharmaceutical composition contains no more than 2% wt of total impurity after stored at refrigerated conditions for 6 months. In some embodiments, the hydrocortisone liquid pharmaceutical composition contains no more than 2% wt of total impurity after stored at refrigerated conditions for 9 months. In some embodiments, the hydrocortisone liquid pharmaceutical composition contains no more than 2% wt of total impurity after stored at refrigerated conditions for 12 months. In some embodiments, the hydrocortisone liquid pharmaceutical composition contains no more than 2% wt of total impurity after stored at refrigerated conditions for 15 months. In some embodiments, the hydrocortisone liquid pharmaceutical composition contains no more than 2% wt of total impurity after stored at refrigerated conditions for 18 months. In some embodiments, the hydrocortisone liquid pharmaceutical composition contains no more than 2% wt of total impurity after stored at refrigerated conditions for 24 months. In some embodiments, the hydrocortisone liquid pharmaceutical composition contains no more than 2% wt of total impurity after stored at refrigerated conditions for 30 months. In some embodiments, the hydrocortisone liquid pharmaceutical composition contains no more than 2% wt of total impurity after stored at refrigerated conditions for 36 months.

In some embodiments, a hydrocortisone liquid pharmaceutical composition contains no more than 1% wt of total impurity after stored at refrigerated conditions for at least 3 months, at least 6 months, at least 9 months, at least 12 months, at least 15 months, at least 18 months, at least 24 months, at least 30 months, or at least 36 months. In some embodiments, the hydrocortisone liquid pharmaceutical composition contains no more than 1% wt of total impurity after stored at refrigerated conditions for 3 months. In some embodiments, the hydrocortisone liquid pharmaceutical composition contains no more than 1% wt of total impurity after stored at refrigerated conditions for 6 months. In some embodiments, the hydrocortisone liquid pharmaceutical composition contains no more than 1% wt of total impurity after stored at refrigerated conditions for 9 months. In some embodiments, the hydrocortisone liquid pharmaceutical composition contains no more than 1% wt of total impurity after stored at refrigerated conditions for 12 months. In some embodiments, the hydrocortisone liquid pharmaceutical composition contains no more than 1% wt of total impurity after stored at refrigerated conditions for 15 months. In some embodiments, the hydrocortisone liquid pharmaceutical composition contains no more than 1% wt of total impurity after stored at refrigerated conditions for 18 months. In some embodiments, the hydrocortisone liquid pharmaceutical composition contains no more than 1% wt of total impurity after stored at refrigerated conditions for 24 months. In some embodiments, the hydrocortisone liquid pharmaceutical composition contains no more than 1% wt of total impurity after stored at refrigerated conditions for 30 months. In some embodiments, the hydrocortisone liquid pharmaceutical composition contains no more than 1% wt of total impurity after stored at refrigerated conditions for 36 months.

In some embodiments, a hydrocortisone liquid pharmaceutical composition described herein retains at least 95% wt of the initial hydrocortisone amount after stored at refrigerated conditions for at least 3 months, at least 6 months, at least 9 months, at least 12 months, at least 15 months, at least 18 months, at least 24 months, at least 30 months, or at least 36 months. In some embodiments, the hydrocortisone liquid pharmaceutical composition retains at least 95% wt of the initial hydrocortisone amount after stored at refrigerated conditions for 3 months. In some embodiments, the hydrocortisone liquid pharmaceutical composition retains at least 95% wt of the initial hydrocortisone amount after stored at refrigerated conditions for 6 months. In some embodiments, the hydrocortisone liquid pharmaceutical composition retains at least 95% wt of the initial hydrocortisone amount after stored at refrigerated conditions for 9 months. In some embodiments, the hydrocortisone liquid pharmaceutical composition retains at least 95% wt of the initial hydrocortisone amount after stored at refrigerated conditions for 12 months. In some embodiments, the hydrocortisone liquid pharmaceutical composition retains at least 95% wt of the initial hydrocortisone amount after stored at refrigerated conditions for 15 months. In some embodiments, the hydrocortisone liquid pharmaceutical composition retains at least 95% wt of the initial hydrocortisone amount after stored at refrigerated conditions for 18 months. In some embodiments, the hydrocortisone liquid pharmaceutical composition retains at least 95% wt of the initial hydrocortisone amount after stored at refrigerated conditions for 24 months. In some embodiments, the hydrocortisone liquid pharmaceutical composition retains at least 95% wt of the initial hydrocortisone amount after stored at refrigerated conditions for 30 months. In some embodiments, the hydrocortisone liquid pharmaceutical composition retains at least 95% wt of the initial hydrocortisone amount after stored at refrigerated conditions for 36 months.

In some embodiments, a hydrocortisone liquid pharmaceutical composition described herein at least 98% wt of the initial hydrocortisone amount after stored at refrigerated conditions for at least 3 months, at least 6 months, at least 9 months, at least 12 months, at least 15 months, at least 18 months, at least 24 months, at least 30 months, or at least 36 months. In some embodiments, the hydrocortisone liquid pharmaceutical composition retains at least 98% wt of the initial hydrocortisone amount after stored at refrigerated conditions for 3 months. In some embodiments, the hydrocortisone liquid pharmaceutical composition retains at least 98% wt of the initial hydrocortisone amount after stored at refrigerated conditions for 6 months. In some embodiments, the hydrocortisone liquid pharmaceutical composition retains at least 98% wt of the initial hydrocortisone amount after stored at refrigerated conditions for 9 months. In some embodiments, the hydrocortisone liquid pharmaceutical composition retains at least 98% wt of the initial hydrocortisone amount after stored at refrigerated conditions for 12 months. In some embodiments, the hydrocortisone liquid pharmaceutical composition retains at least 98% wt of the initial hydrocortisone amount after stored at refrigerated conditions for 15 months. In some embodiments, the hydrocortisone liquid pharmaceutical composition retains at least 98% wt of the initial hydrocortisone amount after stored at refrigerated conditions for 18 months. In some embodiments, the hydrocortisone liquid pharmaceutical composition retains at least 98% wt of the initial hydrocortisone amount after stored at refrigerated conditions for 24 months. In some embodiments, the hydrocortisone liquid pharmaceutical composition retains at least 98% wt of the initial hydrocortisone amount after stored at refrigerated conditions for 30 months. In some embodiments, the hydrocortisone liquid pharmaceutical composition retains at least 98% wt of the initial hydrocortisone amount after stored at refrigerated conditions for 36 months.

In some embodiments, hydrocortisone liquid compositions described herein are stable after stored at ambient or room temperature conditions for at least 1 month, at least 2 months, at least 3 months, at least 6 months, at least 9 months, at least 12 months, at least 15 months, at least 18 months, and at least 24 months. In some embodiments, temperature excursions are permitted when the hydrocortisone liquid compositions are stored at room temperature conditions. In some embodiments, temperature excursions for room temperature conditions are permitted up to 30° C. In some embodiments, the hydrocortisone oral liquid formulations described herein are stable after stored at ambient or room temperature conditions with temperature excursions permitted up to 30° C. for at least 1 month, at least 2 months, at least 3 months, at least 6 months, at least 9 months, at least 12 months, at least 15 months, at least 18 months, and at least 24 months.

In some embodiments, the hydrocortisone liquid pharmaceutical composition described herein contains no more than 2% wt of total impurity after stored at about 15° C. to about 25° C. for at least 3 months, at least 6 months, at least 9 months, at least 12 months, at least 15 months, at least 18 months, or at least 24 months. In some embodiments, the hydrocortisone liquid pharmaceutical composition contains no more than 2% wt of total impurity after stored at about 15° C. to about 25° C. for 3 months. In some embodiments, the hydrocortisone liquid pharmaceutical composition contains no more than 2% wt of total impurity after stored at about 15° C. to about 25° C. for 6 months. In some embodiments, the hydrocortisone liquid pharmaceutical composition contains no more than 2% wt of total impurity after stored at about 15° C. to about 25° C. for 9 months. In some embodiments, the hydrocortisone liquid pharmaceutical composition contains no more than 2% wt of total impurity after stored at about 15° C. to about 25° C. for 12 months. In some embodiments, the hydrocortisone liquid pharmaceutical composition contains no more than 2% wt of total impurity after stored at about 15° C. to about 25° C. for 15 months. In some embodiments, the hydrocortisone liquid pharmaceutical composition contains no more than 2% wt of total impurity after stored at about 15° C. to about 25° C. for 18 months. In some embodiments, the hydrocortisone liquid pharmaceutical composition contains no more than 2% wt of total impurity after stored at about 15° C. to about 25° C. for 24 months.

In some embodiments, a hydrocortisone liquid pharmaceutical composition contains no more than 1% wt of total impurity after stored at about 15° C. to about 25° C. for at least 3 months, at least 6 months, at least 9 months, at least 12 months, at least 15 months, at least 18 months, or at least 24 months. In some embodiments, the hydrocortisone liquid pharmaceutical composition contains no more than 1% wt of total impurity after stored at about 15° C. to about 25° C. for 3 months. In some embodiments, the hydrocortisone liquid pharmaceutical composition contains no more than 1% wt of total impurity after stored at about 15° C. to about 25° C. for 6 months. In some embodiments, the hydrocortisone liquid pharmaceutical composition contains no more than 1% wt of total impurity after stored at about 15° C. to about 25° C. for 9 months. In some embodiments, the hydrocortisone liquid pharmaceutical composition contains no more than 1% wt of total impurity after stored at about 15° C. to about 25° C. for 12 months. In some embodiments, the hydrocortisone liquid pharmaceutical composition contains no more than 1% wt of total impurity after stored at about 15° C. to about 25° C. for 15 months. In some embodiments, the hydrocortisone liquid pharmaceutical composition contains no more than 1% wt of total impurity after stored at about 15° C. to about 25° C. for 18 months. In some embodiments, the hydrocortisone liquid pharmaceutical composition contains no more than 1% wt of total impurity after stored at about 15° C. to about 25° C. for 24 months.

In some embodiments, a hydrocortisone liquid pharmaceutical composition described herein retains at least 95% wt of the initial hydrocortisone amount after stored at about 15° C. to about 25° C. for at least 3 months, at least 6 months, at least 9 months, at least 12 months, at least 15 months, at least 18 months, or at least 24 months. In some embodiments, the hydrocortisone liquid pharmaceutical composition retains at least 95% wt of the initial hydrocortisone amount after stored at about 15° C. to about 25° C. for 3 months. In some embodiments, the hydrocortisone liquid pharmaceutical composition retains at least 95% wt of the initial hydrocortisone amount after stored at about 15° C. to about 25° C. for 6 months. In some embodiments, the hydrocortisone liquid pharmaceutical composition retains at least 95% wt of the initial hydrocortisone amount after stored at about 15° C. to about 25° C. for 9 months. In some embodiments, the hydrocortisone liquid pharmaceutical composition retains at least 95% wt of the initial hydrocortisone amount after stored at about 15° C. to about 25° C. for 12 months. In some embodiments, the hydrocortisone liquid pharmaceutical composition retains at least 95% wt of the initial hydrocortisone amount after stored at about 15° C. to about 25° C. for 15 months. In some embodiments, the hydrocortisone liquid pharmaceutical composition retains at least 95% wt of the initial hydrocortisone amount after stored at about 15° C. to about 25° C. for 18 months. In some embodiments, the hydrocortisone liquid pharmaceutical composition retains at least 95% wt of the initial hydrocortisone amount after stored at about 15° C. to about 25° C. for 24 months.

In some embodiments, a hydrocortisone liquid pharmaceutical composition described herein retains at least 98% wt of the initial hydrocortisone amount after stored at about 15° C. to about 25° C. for at least 3 months, at least 6 months, at least 9 months, at least 12 months, at least 15 months, at least 18 months, or at least 24 months. In some embodiments, the hydrocortisone liquid pharmaceutical composition retains at least 98% wt of the initial hydrocortisone amount after stored at about 15° C. to about 25° C. for 3 months. In some embodiments, the hydrocortisone liquid pharmaceutical composition retains at least 98% wt of the initial hydrocortisone amount after stored at about 15° C. to about 25° C. for 6 months. In some embodiments, the hydrocortisone liquid pharmaceutical composition retains at least 98% wt of the initial hydrocortisone amount after stored at about 15° C. to about 25° C. for 9 months. In some embodiments, the hydrocortisone liquid pharmaceutical composition retains at least 98% wt of the initial hydrocortisone amount after stored at about 15° C. to about 25° C. for 12 months. In some embodiments, the hydrocortisone liquid pharmaceutical composition retains at least 98% wt of the initial hydrocortisone amount after stored at about 15° C. to about 25° C. for 15 months. In some embodiments, the hydrocortisone liquid pharmaceutical composition retains at least 98% wt of the initial hydrocortisone amount after stored at about 15° C. to about 25° C. for 18 months. In some embodiments, the hydrocortisone liquid pharmaceutical composition retains at least 98% wt of the initial hydrocortisone amount after stored at about 15° C. to about 25° C. for 24 months.

In some embodiments, a hydrocortisone liquid pharmaceutical composition described herein contains no more than 2% wt of total impurity after stored at about 15° C. to about 25° C., with temperature excursions permitted up to 30° C., for at least 3 months, at least 6 months, at least 9 months, at least 12 months, at least 15 months, at least 18 months, or at least 24 months. In some embodiments, the hydrocortisone liquid pharmaceutical composition contains no more than 2% wt of total impurity after stored at about 15° C. to about 25° C., with temperature excursions permitted up to 30° C., for 3 months. In some embodiments, the hydrocortisone liquid pharmaceutical composition contains no more than 2% wt of total impurity after stored at about 15° C. to about 25° C., with temperature excursions permitted up to 30° C., for 6 months. In some embodiments, the hydrocortisone liquid pharmaceutical composition contains no more than 2% wt of total impurity after stored at about 15° C. to about 25° C., with temperature excursions permitted up to 30° C., for 9 months. In some embodiments, the hydrocortisone liquid pharmaceutical composition contains no more than 2% wt of total impurity after stored at about 15° C. to about 25° C., with temperature excursions permitted up to 30° C., for 12 months. In some embodiments, the hydrocortisone liquid pharmaceutical composition contains no more than 2% wt of total impurity after stored at about 15° C. to about 25° C., with temperature excursions permitted up to 30° C., for 15 months. In some embodiments, the hydrocortisone liquid pharmaceutical composition contains no more than 2% wt of total impurity after stored at about 15° C. to about 25° C., with temperature excursions permitted up to 30° C., for 18 months. In some embodiments, the hydrocortisone liquid pharmaceutical composition contains no more than 2% wt of total impurity after stored at about 15° C. to about 25° C., with temperature excursions permitted up to 30° C., for 24 months.

In some embodiments, a hydrocortisone liquid pharmaceutical composition described herein contains no more than 1% wt of total impurity after stored at about 15° C. to about 25° C., with temperature excursions permitted up to 30° C., for at least 3 months, at least 6 months, at least 9 months, at least 12 months, at least 15 months, at least 18 months, or at least 24 months. In some embodiments, the hydrocortisone liquid pharmaceutical composition contains no more than 1% wt of total impurity after stored at about 15° C. to about 25° C., with temperature excursions permitted up to 30° C., for 3 months. In some embodiments, the hydrocortisone liquid pharmaceutical composition contains no more than 1% wt of total impurity after stored at about 15° C. to about 25° C., with temperature excursions permitted up to 30° C., for 6 months. In some embodiments, the hydrocortisone liquid pharmaceutical composition contains no more than 1% wt of total impurity after stored at about 15° C. to about 25° C., with temperature excursions permitted up to 30° C., for 9 months. In some embodiments, the hydrocortisone liquid pharmaceutical composition contains no more than 1% wt of total impurity after stored at about 15° C. to about 25° C., with temperature excursions permitted up to 30° C., for 12 months. In some embodiments, the hydrocortisone liquid pharmaceutical composition contains no more than 1% wt of total impurity after stored at about 15° C. to about 25° C., with temperature excursions permitted up to 30° C., for 15 months. In some embodiments, the hydrocortisone liquid pharmaceutical composition contains no more than 1% wt of total impurity after stored at about 15° C. to about 25° C., with temperature excursions permitted up to 30° C., for 18 months. In some embodiments, the hydrocortisone liquid pharmaceutical composition contains no more than 1% wt of total impurity after stored at about 15° C. to about 25° C., with temperature excursions permitted up to 30° C., for 24 months.

In some embodiments, a hydrocortisone liquid pharmaceutical composition described herein retains at least 95% wt of the initial hydrocortisone amount after stored at about 15° C. to about 25° C., with temperature excursions permitted up to 30° C., for at least 3 months, at least 6 months, at least 9 months, at least 12 months, at least 15 months, at least 18 months, or at least 24 months. In some embodiments, the hydrocortisone liquid pharmaceutical composition retains at least 95% wt of the initial hydrocortisone amount after stored at about 15° C. to about 25° C., with temperature excursions permitted up to 30° C., for 3 months. In some embodiments, the hydrocortisone liquid pharmaceutical composition retains at least 95% wt of the initial hydrocortisone amount after stored at about 15° C. to about 25° C., with temperature excursions permitted up to 30° C., for 6 months. In some embodiments, the hydrocortisone liquid pharmaceutical composition retains at least 95% wt of the initial hydrocortisone amount after stored at about 15° C. to about 25° C., with temperature excursions permitted up to 30° C., for 9 months. In some embodiments, the hydrocortisone liquid pharmaceutical composition retains at least 95% wt of the initial hydrocortisone amount after stored at about 15° C. to about 25° C., with temperature excursions permitted up to 30° C., for 12 months. In some embodiments, the hydrocortisone liquid pharmaceutical composition retains at least 95% wt of the initial hydrocortisone amount after stored at about 15° C. to about 25° C., with temperature excursions permitted up to 30° C., for 15 months. In some embodiments, the hydrocortisone liquid pharmaceutical composition retains at least 95% wt of the initial hydrocortisone amount after stored at about 15° C. to about 25° C., with temperature excursions permitted up to 30° C., for 18 months. In some embodiments, the hydrocortisone liquid pharmaceutical composition retains at least 95% wt of the initial hydrocortisone amount after stored at about 15° C. to about 25° C., with temperature excursions permitted up to 30° C., for 24 months.

In some embodiments, a hydrocortisone liquid pharmaceutical composition described herein retains at least 98% wt of the initial hydrocortisone amount after stored at about 15° C. to about 25° C., with temperature excursions permitted up to 30° C., for at least 3 months, at least 6 months, at least 9 months, at least 12 months, at least 15 months, at least 18 months, or at least 24 months. In some embodiments, the hydrocortisone liquid pharmaceutical composition retains at least 98% wt of the initial hydrocortisone amount after stored at about 15° C. to about 25° C., with temperature excursions permitted up to 30° C., for 3 months. In some embodiments, the hydrocortisone liquid pharmaceutical composition retains at least 98% wt of the initial hydrocortisone amount after stored at about 15° C. to about 25° C., with temperature excursions permitted up to 30° C., for 6 months. In some embodiments, the hydrocortisone liquid pharmaceutical composition retains at least 98% wt of the initial hydrocortisone amount after stored at about 15° C. to about 25° C., with temperature excursions permitted up to 30° C., for 9 months. In some embodiments, the hydrocortisone liquid pharmaceutical composition retains at least 98% wt of the initial hydrocortisone amount after stored at about 15° C. to about 25° C., with temperature excursions permitted up to 30° C., for 12 months. In some embodiments, the hydrocortisone liquid pharmaceutical composition retains at least 98% wt of the initial hydrocortisone amount after stored at about 15° C. to about 25° C., with temperature excursions permitted up to 30° C., for 15 months. In some embodiments, the hydrocortisone liquid pharmaceutical composition retains at least 98% wt of the initial hydrocortisone amount after stored at about 15° C. to about 25° C., with temperature excursions permitted up to 30° C., for 18 months. In some embodiments, the hydrocortisone liquid pharmaceutical composition retains at least 98% wt of the initial hydrocortisone amount after stored at about 15° C. to about 25° C., with temperature excursions permitted up to 30° C., for 24 months.

In some embodiments, the hydrocortisone liquid pharmaceutical composition described herein contains no more than 2% wt of total impurity after stored at about 15° C. to about 30° C. for at least 3 months, at least 6 months, at least 9 months, at least 12 months, at least 15 months, at least 18 months, or at least 24 months. In some embodiments, the hydrocortisone liquid pharmaceutical composition contains no more than 2% wt of total impurity after stored at about 15° C. to about 30° C. for 3 months. In some embodiments, the hydrocortisone liquid pharmaceutical composition contains no more than 2% wt of total impurity after stored at about 15° C. to about 30° C. for 6 months. In some embodiments, the hydrocortisone liquid pharmaceutical composition contains no more than 2% wt of total impurity after stored at about 15° C. to about 30° C. for 9 months. In some embodiments, the hydrocortisone liquid pharmaceutical composition contains no more than 2% wt of total impurity after stored at about 15° C. to about 30° C. for 12 months. In some embodiments, the hydrocortisone liquid pharmaceutical composition contains no more than 2% wt of total impurity after stored at about 15° C. to about 30° C. for 15 months. In some embodiments, the hydrocortisone liquid pharmaceutical composition contains no more than 2% wt of total impurity after stored at about 15° C. to about 30° C. for 18 months. In some embodiments, the hydrocortisone liquid pharmaceutical composition contains no more than 2% wt of total impurity after stored at about 15° C. to about 30° C. for 24 months.

In some embodiments, a hydrocortisone liquid pharmaceutical composition contains no more than 1% wt of total impurity after stored at about 15° C. to about 30° C. for at least 3 months, at least 6 months, at least 9 months, at least 12 months, at least 15 months, at least 18 months, or at least 24 months. In some embodiments, the hydrocortisone liquid pharmaceutical composition contains no more than 1% wt of total impurity after stored at about 15° C. to about 30° C. for 3 months. In some embodiments, the hydrocortisone liquid pharmaceutical composition contains no more than 1% wt of total impurity after stored at about 15° C. to about 30° C. for 6 months. In some embodiments, the hydrocortisone liquid pharmaceutical composition contains no more than 1% wt of total impurity after stored at about 15° C. to about 30° C. for 9 months. In some embodiments, the hydrocortisone liquid pharmaceutical composition contains no more than 1% wt of total impurity after stored at about 15° C. to about 30° C. for 12 months. In some embodiments, the hydrocortisone liquid pharmaceutical composition contains no more than 1% wt of total impurity after stored at about 15° C. to about 30° C. for 15 months. In some embodiments, the hydrocortisone liquid pharmaceutical composition contains no more than 1% wt of total impurity after stored at about 15° C. to about 30° C. for 18 months. In some embodiments, the hydrocortisone liquid pharmaceutical composition contains no more than 1% wt of total impurity after stored at about 15° C. to about 30° C. for 24 months.

In some embodiments, a hydrocortisone liquid pharmaceutical composition described herein retains at least 95% wt of the initial hydrocortisone amount after stored at about 15° C. to about 30° C. for at least 3 months, at least 6 months, at least 9 months, at least 12 months, at least 15 months, at least 18 months, or at least 24 months. In some embodiments, the hydrocortisone liquid pharmaceutical composition retains at least 95% wt of the initial hydrocortisone amount after stored at about 15° C. to about 30° C. for 3 months. In some embodiments, the hydrocortisone liquid pharmaceutical composition retains at least 95% wt of the initial hydrocortisone amount after stored at about 15° C. to about 30° C. for 6 months. In some embodiments, the hydrocortisone liquid pharmaceutical composition retains at least 95% wt of the initial hydrocortisone amount after stored at about 15° C. to about 30° C. for 9 months. In some embodiments, the hydrocortisone liquid pharmaceutical composition retains at least 95% wt of the initial hydrocortisone amount after stored at about 15° C. to about 30° C. for 12 months. In some embodiments, the hydrocortisone liquid pharmaceutical composition retains at least 95% wt of the initial hydrocortisone amount after stored at about 15° C. to about 30° C. for 15 months. In some embodiments, the hydrocortisone liquid pharmaceutical composition retains at least 95% wt of the initial hydrocortisone amount after stored at about 15° C. to about 30° C. for 18 months. In some embodiments, the hydrocortisone liquid pharmaceutical composition retains at least 95% wt of the initial hydrocortisone amount after stored at about 15° C. to about 30° C. for 24 months.

In some embodiments, a hydrocortisone liquid pharmaceutical composition described herein retains at least 98% wt of the initial hydrocortisone amount after stored at about 15° C. to about 30° C. for at least 3 months, at least 6 months, at least 9 months, at least 12 months, at least 15 months, at least 18 months, or at least 24 months. In some embodiments, the hydrocortisone liquid pharmaceutical composition retains at least 98% wt of the initial hydrocortisone amount after stored at about 15° C. to about 30° C. for 3 months. In some embodiments, the hydrocortisone liquid pharmaceutical composition retains at least 98% wt of the initial hydrocortisone amount after stored at about 15° C. to about 30° C. for 6 months. In some embodiments, the hydrocortisone liquid pharmaceutical composition retains at least 98% wt of the initial hydrocortisone amount after stored at about 15° C. to about 30° C. for 9 months. In some embodiments, the hydrocortisone liquid pharmaceutical composition retains at least 98% wt of the initial hydrocortisone amount after stored at about 15° C. to about 30° C. for 12 months. In some embodiments, the hydrocortisone liquid pharmaceutical composition retains at least 98% wt of the initial hydrocortisone amount after stored at about 15° C. to about 30° C. for 15 months. In some embodiments, the hydrocortisone liquid pharmaceutical composition retains at least 98% wt of the initial hydrocortisone amount after stored at about 15° C. to about 30° C. for 18 months. In some embodiments, the hydrocortisone liquid pharmaceutical composition retains at least 98% wt of the initial hydrocortisone amount after stored at about 15° C. to about 30° C. for 24 months.

In some embodiments, a hydrocortisone liquid pharmaceutical composition described herein contains no more than 2% wt of total impurity after stored at room temperature for at least 3 months, at least 6 months, at least 9 months, at least 12 months, at least 15 months, at least 18 months, or at least 24 months. In some embodiments, the hydrocortisone liquid pharmaceutical composition contains no more than 2% wt of total impurity after stored at room temperature for 3 months. In some embodiments, the hydrocortisone liquid pharmaceutical composition contains no more than 2% wt of total impurity after stored at room temperature for 6 months. In some embodiments, the hydrocortisone liquid pharmaceutical composition contains no more than 2% wt of total impurity after stored at room temperature for 9 months. In some embodiments, the hydrocortisone liquid pharmaceutical composition contains no more than 2% wt of total impurity after stored at room temperature for 12 months. In some embodiments, the hydrocortisone liquid pharmaceutical composition contains no more than 2% wt of total impurity after stored at room temperature for 15 months. In some embodiments, the hydrocortisone liquid pharmaceutical composition contains no more than 2% wt of total impurity after stored at room temperature for 18 months. In some embodiments, the hydrocortisone liquid pharmaceutical composition contains no more than 2% wt of total impurity after stored at room temperature for 24 months.

In some embodiments, a hydrocortisone liquid pharmaceutical composition described herein contains no more than 1% wt of total impurity after stored at room temperature for at least 3 months, at least 6 months, at least 9 months, at least 12 months, at least 15 months, at least 18 months, or at least 24 months. In some embodiments, the hydrocortisone liquid pharmaceutical composition contains no more than 1% wt of total impurity after stored at room temperature for 3 months. In some embodiments, the hydrocortisone liquid pharmaceutical composition contains no more than 1% wt of total impurity after stored at room temperature for 6 months. In some embodiments, the hydrocortisone liquid pharmaceutical composition contains no more than 1% wt of total impurity after stored at room temperature for 9 months. In some embodiments, the hydrocortisone liquid pharmaceutical composition contains no more than 1% wt of total impurity after stored at room temperature for 12 months. In some embodiments, the hydrocortisone liquid pharmaceutical composition contains no more than 1% wt of total impurity after stored at room temperature for 15 months. In some embodiments, the hydrocortisone liquid pharmaceutical composition contains no more than 1% wt of total impurity after stored at room temperature for 18 months. In some embodiments, the hydrocortisone liquid pharmaceutical composition contains no more than 1% wt of total impurity after stored at room temperature for 24 months.

In some embodiments, a hydrocortisone liquid pharmaceutical composition described herein retains at least 95% wt of the initial hydrocortisone amount after stored at room temperature for at least 3 months, at least 6 months, at least 9 months, at least 12 months, at least 15 months, at least 18 months, or at least 24 months. In some embodiments, the hydrocortisone liquid pharmaceutical composition retains at least 95% wt of the initial hydrocortisone amount after stored at room temperature for 3 months. In some embodiments, the hydrocortisone liquid pharmaceutical composition retains at least 95% wt of the initial hydrocortisone amount after stored at room temperature for 6 months. In some embodiments, the hydrocortisone liquid pharmaceutical composition retains at least 95% wt of the initial hydrocortisone amount after stored at room temperature for 9 months. In some embodiments, the hydrocortisone liquid pharmaceutical composition retains at least 95% wt of the initial hydrocortisone amount after stored at room temperature for 12 months. In some embodiments, the hydrocortisone liquid pharmaceutical composition retains at least 95% wt of the initial hydrocortisone amount after stored at room temperature for 15 months. In some embodiments, the hydrocortisone liquid pharmaceutical composition retains at least 95% wt of the initial hydrocortisone amount after stored at room temperature for 18 months. In some embodiments, the hydrocortisone liquid pharmaceutical composition retains at least 95% wt of the initial hydrocortisone amount after stored at room temperature for 24 months.

In some embodiments, a hydrocortisone liquid pharmaceutical composition described herein retains at least 98% wt of the initial hydrocortisone amount after stored at room temperature for at least 3 months, at least 6 months, at least 9 months, at least 12 months, at least 15 months, at least 18 months, or at least 24 months. In some embodiments, the hydrocortisone liquid pharmaceutical composition retains at least 98% wt of the initial hydrocortisone amount after stored at room temperature for 3 months. In some embodiments, the hydrocortisone liquid pharmaceutical composition retains at least 98% wt of the initial hydrocortisone amount after stored at room temperature for 6 months. In some embodiments, the hydrocortisone liquid pharmaceutical composition retains at least 98% wt of the initial hydrocortisone amount after stored at room temperature for 9 months. In some embodiments, the hydrocortisone liquid pharmaceutical composition retains at least 98% wt of the initial hydrocortisone amount after stored at room temperature for 12 months. In some embodiments, the hydrocortisone liquid pharmaceutical composition retains at least 98% wt of the initial hydrocortisone amount after stored at room temperature for 15 months. In some embodiments, the hydrocortisone liquid pharmaceutical composition retains at least 98% wt of the initial hydrocortisone amount after stored at room temperature for 18 months. In some embodiments, the hydrocortisone liquid pharmaceutical composition retains at least 98% wt of the initial hydrocortisone amount after stored at room temperature for 24 months.

In some embodiments, a hydrocortisone liquid pharmaceutical composition described herein contains no more than 2% wt of total impurity after stored at ambient conditions for at least 3 months, at least 6 months, at least 9 months, at least 12 months, at least 15 months, at least 18 months, or at least 24 months. In some embodiments, the hydrocortisone liquid pharmaceutical composition contains no more than 2% wt of total impurity after stored at ambient conditions for 3 months. In some embodiments, the hydrocortisone liquid pharmaceutical composition contains no more than 2% wt of total impurity after stored at ambient conditions for 6 months. In some embodiments, the hydrocortisone liquid pharmaceutical composition contains no more than 2% wt of total impurity after stored at ambient conditions for 9 months. In some embodiments, the hydrocortisone liquid pharmaceutical composition contains no more than 2% wt of total impurity after stored at ambient conditions for 12 months. In some embodiments, the hydrocortisone liquid pharmaceutical composition contains no more than 2% wt of total impurity after stored at ambient conditions for 15 months. In some embodiments, the hydrocortisone liquid pharmaceutical composition contains no more than 2% wt of total impurity after stored at ambient conditions for 18 months. In some embodiments, the hydrocortisone liquid pharmaceutical composition contains no more than 2% wt of total impurity after stored at ambient conditions for 24 months.

In some embodiments, a hydrocortisone liquid pharmaceutical composition described herein contains no more than 1% wt of total impurity after stored at ambient conditions for at least 3 months, at least 6 months, at least 9 months, at least 12 months, at least 15 months, at least 18 months, or at least 24 months. In some embodiments, the hydrocortisone liquid pharmaceutical composition contains no more than 1% wt of total impurity after stored at ambient conditions for 3 months. In some embodiments, the hydrocortisone liquid pharmaceutical composition contains no more than 1% wt of total impurity after stored at ambient conditions for 6 months. In some embodiments, the hydrocortisone liquid pharmaceutical composition contains no more than 1% wt of total impurity after stored at ambient conditions for 9 months. In some embodiments, the hydrocortisone liquid pharmaceutical composition contains no more than 1% wt of total impurity after stored at ambient conditions for 12 months. In some embodiments, the hydrocortisone liquid pharmaceutical composition contains no more than 1% wt of total impurity after stored at ambient conditions for 15 months. In some embodiments, the hydrocortisone liquid pharmaceutical composition contains no more than 1% wt of total impurity after stored at ambient conditions for 18 months. In some embodiments, the hydrocortisone liquid pharmaceutical composition contains no more than 1% wt of total impurity after stored at ambient conditions for 24 months.

In some embodiments, a hydrocortisone liquid pharmaceutical composition described herein retains at least 95% wt of the initial hydrocortisone amount after stored at ambient conditions for at least 3 months, at least 6 months, at least 9 months, at least 12 months, at least 15 months, at least 18 months, or at least 24 months. In some embodiments, the hydrocortisone liquid pharmaceutical composition retains at least 95% wt of the initial hydrocortisone amount after stored at ambient conditions for 3 months. In some embodiments, the hydrocortisone liquid pharmaceutical composition retains at least 95% wt of the initial hydrocortisone amount after stored at ambient conditions for 6 months. In some embodiments, the hydrocortisone liquid pharmaceutical composition retains at least 95% wt of the initial hydrocortisone amount after stored at ambient conditions for 9 months. In some embodiments, the hydrocortisone liquid pharmaceutical composition retains at least 95% wt of the initial hydrocortisone amount after stored at ambient conditions for 12 months. In some embodiments, the hydrocortisone liquid pharmaceutical composition retains at least 95% wt of the initial hydrocortisone amount after stored at ambient conditions for 15 months. In some embodiments, the hydrocortisone liquid pharmaceutical composition retains at least 95% wt of the initial hydrocortisone amount after stored at ambient conditions for 18 months. In some embodiments, the hydrocortisone liquid pharmaceutical composition retains at least 95% wt of the initial hydrocortisone amount after stored at ambient conditions for 24 months.

In some embodiments, a hydrocortisone liquid pharmaceutical composition described herein retains at least 98% wt of the initial hydrocortisone amount after stored at ambient conditions for at least 3 months, at least 6 months, at least 9 months, at least 12 months, at least 15 months, at least 18 months, or at least 24 months. In some embodiments, the hydrocortisone liquid pharmaceutical composition retains at least 98% wt of the initial hydrocortisone amount after stored at ambient conditions for 3 months. In some embodiments, the hydrocortisone liquid pharmaceutical composition retains at least 98% wt of the initial hydrocortisone amount after stored at ambient conditions for 6 months. In some embodiments, the hydrocortisone liquid pharmaceutical composition retains at least 98% wt of the initial hydrocortisone amount after stored at ambient conditions for 9 months. In some embodiments, the hydrocortisone liquid pharmaceutical composition retains at least 98% wt of the initial hydrocortisone amount after stored at ambient conditions for 12 months. In some embodiments, the hydrocortisone liquid pharmaceutical composition retains at least 98% wt of the initial hydrocortisone amount after stored at ambient conditions for 15 months. In some embodiments, the hydrocortisone liquid pharmaceutical composition retains at least 98% wt of the initial hydrocortisone amount after stored at ambient conditions for 18 months. In some embodiments, the hydrocortisone liquid pharmaceutical composition retains at least 98% wt of the initial hydrocortisone amount after stored at ambient conditions for 24 months.

In some embodiments, hydrocortisone oral liquid formulations described herein are stable after stored at accelerated conditions, for at least 1 month, at least 2 months, at least 3 months, at least 4 months, at least 5 months, at least 6 months, at least 7 months, at least 8 months, at least 9 months, at least 10 months, at least 11 months or at least 12 months. In some embodiments, the hydrocortisone oral liquid formulations described herein are stable after stored at about 40° C.±2° C., for at least 1 month, at least 2 months, at least 3 months, at least 4 months, at least 5 months, at least 6 months, at least 7 months, at least 8 months, at least 9 months, at least 10 months, at least 11 months or at least 12 months.

In some embodiments, a hydrocortisone liquid pharmaceutical composition described herein contains no more than 2% wt of total impurity after stored at about 40° C.±2° C. for at least 3 months, at least 6 months, at least 9 months, or at least 12 months. In some embodiments, the hydrocortisone liquid pharmaceutical composition contains no more than 2% wt of total impurity after stored at about 40° C.±2° C. for 3 months. In some embodiments, the hydrocortisone liquid pharmaceutical composition contains no more than 2% wt of total impurity after stored at about 40° C.±2° C. for 6 months. In some embodiments, the hydrocortisone liquid pharmaceutical composition contains no more than 2% wt of total impurity after stored at about 40° C.±2° C. for 9 months. In some embodiments, the hydrocortisone liquid pharmaceutical composition contains no more than 2% wt of total impurity after stored at about 40° C.±2° C. for 12 months.

In some embodiments, a hydrocortisone liquid pharmaceutical composition described herein contains no more than 1% wt of total impurity after stored at about 40° C.±2° C. for at least 3 months, at least 6 months, at least 9 months, at or least 12 months. In some embodiments, the hydrocortisone liquid pharmaceutical composition contains no more than 1% wt of total impurity after stored at about 40° C.±2° C. for 3 months. In some embodiments, the hydrocortisone liquid pharmaceutical composition contains no more than 1% wt of total impurity after stored at about 40° C.±2° C. for 6 months. In some embodiments, the hydrocortisone liquid pharmaceutical composition contains no more than 1% wt of total impurity after stored at about 40° C.±2° C. for 9 months. In some embodiments, the hydrocortisone liquid pharmaceutical composition contains no more than 1% wt of total impurity after stored at about 40° C.±2° C. for 12 months.

In some embodiments, a hydrocortisone liquid pharmaceutical composition described herein retains at least 95% wt of the initial hydrocortisone amount after stored at about 40° C.±2° C. for at least 3 months, at least 6 months, at least 9 months, or at least 12 months. In some embodiments, the hydrocortisone liquid pharmaceutical composition retains at least 95% wt of the initial hydrocortisone amount after stored at about 40° C.±2° C. for 3 months. In some embodiments, the hydrocortisone liquid pharmaceutical composition retains at least 95% wt of the initial hydrocortisone amount after stored at about 40° C.±2° C. for 6 months. In some embodiments, the hydrocortisone liquid pharmaceutical composition retains at least 95% wt of the initial hydrocortisone amount after stored at about 40° C.±2° C. for 9 months. In some embodiments, the hydrocortisone liquid pharmaceutical composition retains at least 95% wt of the initial hydrocortisone amount after stored at about 40° C.±2° C. for 12 months.

In some embodiments, a hydrocortisone liquid pharmaceutical composition described herein retains at least 98% wt of the initial hydrocortisone amount after stored at about 40° C.±2° C. for at least 3 months, at least 6 months, at least 9 months, or at least 12 months. In some embodiments, the hydrocortisone liquid pharmaceutical composition retains at least 98% wt of the initial hydrocortisone amount after stored at about 40° C.±2° C. for 3 months. In some embodiments, the hydrocortisone liquid pharmaceutical composition retains at least 98% wt of the initial hydrocortisone amount after stored at about 40° C.±2° C. for 6 months. In some embodiments, the hydrocortisone liquid pharmaceutical composition retains at least 98% wt of the initial hydrocortisone amount after stored at about 40° C.±2° C. for 9 months. In some embodiments, the hydrocortisone liquid pharmaceutical composition retains at least 98% wt of the initial hydrocortisone amount after stored at about 40° C.±2° C. for 12 months.

In some embodiments, a hydrocortisone liquid pharmaceutical composition described herein contains no more than 2% wt of total impurity after stored at accelerated conditions for at least 3 months, at least 6 months, at least 9 months, or at least 12 months. In some embodiments, the hydrocortisone liquid pharmaceutical composition contains no more than 2% wt of total impurity after stored at accelerated conditions for 3 months. In some embodiments, the hydrocortisone liquid pharmaceutical composition contains no more than 2% wt of total impurity after stored at accelerated conditions for 6 months. In some embodiments, the hydrocortisone liquid pharmaceutical composition contains no more than 2% wt of total impurity after stored at accelerated conditions for 9 months. In some embodiments, the hydrocortisone liquid pharmaceutical composition contains no more than 2% wt of total impurity after stored at accelerated conditions for 12 months.

In some embodiments, a hydrocortisone liquid pharmaceutical composition described herein contains no more than 1% wt of total impurity after stored at accelerated conditions for at least 3 months, at least 6 months, at least 9 months, at or least 12 months. In some embodiments, the hydrocortisone liquid pharmaceutical composition contains no more than 1% wt of total impurity after stored at accelerated conditions for 3 months. In some embodiments, the hydrocortisone liquid pharmaceutical composition contains no more than 1% wt of total impurity after stored at accelerated conditions for 6 months. In some embodiments, the hydrocortisone liquid pharmaceutical composition contains no more than 1% wt of total impurity after stored at accelerated conditions for 9 months. In some embodiments, the hydrocortisone liquid pharmaceutical composition contains no more than 1% wt of total impurity after stored at accelerated conditions for 12 months.

In some embodiments, a hydrocortisone liquid pharmaceutical composition described herein retains at least 95% wt of the initial hydrocortisone amount after stored at accelerated conditions for at least 3 months, at least 6 months, at least 9 months, or at least 12 months. In some embodiments, the hydrocortisone liquid pharmaceutical composition retains at least 95% wt of the initial hydrocortisone amount after stored at accelerated conditions for 3 months. In some embodiments, the hydrocortisone liquid pharmaceutical composition retains at least 95% wt of the initial hydrocortisone amount after stored at accelerated conditions for 6 months. In some embodiments, the hydrocortisone liquid pharmaceutical composition retains at least 95% wt of the initial hydrocortisone amount after stored at accelerated conditions for 9 months. In some embodiments, the hydrocortisone liquid pharmaceutical composition retains at least 95% wt of the initial hydrocortisone amount after stored at accelerated conditions for 12 months.

In some embodiments, a hydrocortisone liquid pharmaceutical composition described herein retains at least 98% wt of the initial hydrocortisone amount after stored at accelerated conditions for at least 3 months, at least 6 months, at least 9 months, or at least 12 months. In some embodiments, the hydrocortisone liquid pharmaceutical composition retains at least 98% wt of the initial hydrocortisone amount after stored at accelerated conditions for 3 months. In some embodiments, the hydrocortisone liquid pharmaceutical composition retains at least 98% wt of the initial hydrocortisone amount after stored at accelerated conditions for 6 months. In some embodiments, the hydrocortisone liquid pharmaceutical composition retains at least 98% wt of the initial hydrocortisone amount after stored at accelerated conditions for 9 months. In some embodiments, the hydrocortisone liquid pharmaceutical composition retains at least 98% wt of the initial hydrocortisone amount after stored at accelerated conditions for 12 months.

In some embodiments, hydrocortisone oral liquid formulations described herein are stable or shelf-stable when in use after stored in various conditions including refrigerated conditions, room temperature, ambient conditions, and accelerated conditions. Stable or shelf stable as used herein refer to hydrocortisone oral liquid formulations having about 95% or greater of the initial hydrocortisone amount and about 5% wt or less total impurities or related substances at the end of a given storage period. Alternatively, stable or shelf stable as used herein refer to hydrocortisone oral liquid formulations having about 90% wt or greater of initial hydrocortisone amount and about 10% wt or less total impurities or related substances at the end of a given storage period. In some embodiments, the hydrocortisone oral liquid formulations are in use when stored in an opened container.

In some embodiments, a hydrocortisone liquid pharmaceutical composition described herein are stable when in use after stored at refrigerated condition for at least 15 days, 30 days, 60 days, 90 days, or 120 days.

In some embodiments, a hydrocortisone liquid pharmaceutical composition described herein contains no more than 2% wt of total impurity when in use after stored at refrigerated condition for at least 15 days, 30 days, 60 days, 90 days, or 120 days. In some embodiments, the hydrocortisone liquid pharmaceutical composition contains no more than 2% wt of total impurity when in use after stored at refrigerated condition for at least 15 days. In some embodiments, the hydrocortisone liquid pharmaceutical composition contains no more than 2% wt of total impurity when in use after stored at refrigerated condition for at least 30 days. In some embodiments, the hydrocortisone liquid pharmaceutical composition contains no more than 2% wt of total impurity when in use after stored at refrigerated condition for at least 60 days. In some embodiments, the hydrocortisone liquid pharmaceutical composition contains no more than 2% wt of total impurity when in use after stored at refrigerated condition for at least 90 days. In some embodiments, the hydrocortisone liquid pharmaceutical composition contains no more than 2% wt of total impurity when in use after stored at refrigerated condition for at least 120 days.

In some embodiments, a hydrocortisone liquid pharmaceutical composition described herein contains no more than 1% wt of total impurity when in use after stored at refrigerated condition for at least 15 days, 30 days, 60 days, 90 days, or 120 days. In some embodiments, the hydrocortisone liquid pharmaceutical composition contains no more than 1% wt of total impurity when in use after stored at refrigerated condition for at least 15 days. In some embodiments, the hydrocortisone liquid pharmaceutical composition contains no more than 1% wt of total impurity when in use after stored at refrigerated condition for at least 30 days. In some embodiments, the hydrocortisone liquid pharmaceutical composition contains no more than 1% wt of total impurity when in use after stored at refrigerated condition for at least 60 days. In some embodiments, the hydrocortisone liquid pharmaceutical composition contains no more than 1% wt of total impurity when in use after stored at refrigerated condition for at least 90 days. In some embodiments, the hydrocortisone liquid pharmaceutical composition contains no more than 1% wt of total impurity when in use after stored at refrigerated condition for at least 120 days.

In some embodiments, a hydrocortisone liquid pharmaceutical composition described herein retains at least 95% wt of the initial hydrocortisone amount when in use after stored at refrigerated condition for at least 15 days, 30 days, 60 days, 90 days, or 120 days. In some embodiments, the hydrocortisone liquid pharmaceutical composition retains at least 95% wt of the initial hydrocortisone amount when in use after stored at refrigerated conditions for at least 15 days. In some embodiments, the hydrocortisone liquid pharmaceutical composition retains at least 95% wt of the initial hydrocortisone amount when in use after stored at refrigerated conditions for at least 30 days. In some embodiments, the hydrocortisone liquid pharmaceutical composition retains at least 95% wt of the initial hydrocortisone amount when in use after stored at refrigerated conditions for at least 60 days. In some embodiments, the hydrocortisone liquid pharmaceutical composition retains at least 95% wt of the initial hydrocortisone amount when in use after stored at refrigerated conditions for at least 90 days. In some embodiments, the hydrocortisone liquid pharmaceutical composition retains at least 95% wt of the initial hydrocortisone amount when in use after stored at refrigerated conditions for at least 120 days.

In some embodiments, a hydrocortisone liquid pharmaceutical composition described herein retains at least 98% wt of the initial hydrocortisone amount when in use after stored at refrigerated condition for at least 15 days, 30 days, 60 days, 90 days, or 120 days. In some embodiments, the hydrocortisone liquid pharmaceutical composition retains at least 98% wt of the initial hydrocortisone amount when in use after stored at refrigerated conditions for at least 15 days. In some embodiments, the hydrocortisone liquid pharmaceutical composition retains at least 98% wt of the initial hydrocortisone amount when in use after stored at refrigerated conditions for at least 30 days. In some embodiments, the hydrocortisone liquid pharmaceutical composition retains at least 98% wt of the initial hydrocortisone amount when in use after stored at refrigerated conditions for at least 60 days. In some embodiments, the hydrocortisone liquid pharmaceutical composition retains at least 98% wt of the initial hydrocortisone amount when in use after stored at refrigerated conditions for at least 90 days. In some embodiments, the hydrocortisone liquid pharmaceutical composition retains at least 98% wt of the initial hydrocortisone amount when in use after stored at refrigerated conditions for at least 120 days.

In some embodiments, a hydrocortisone liquid pharmaceutical composition described herein are stable when in use after stored at room temperature or ambient conditions for at least 15 days, 30 days, 60 days, 90 days, or 120 days.

In some embodiments, a hydrocortisone liquid pharmaceutical composition described herein contains no more than 2% wt of total impurity when in use after stored at room temperature or ambient conditions for at least 15 days, 30 days, 60 days, 90 days, or 120 days. In some embodiments, the hydrocortisone liquid pharmaceutical composition contains no more than 2% wt of total impurity when in use after stored at room temperature or ambient conditions for at least 15 days. In some embodiments, the hydrocortisone liquid pharmaceutical composition contains no more than 2% wt of total impurity when in use after stored at room temperature or ambient conditions for at least 30 days. In some embodiments, the hydrocortisone liquid pharmaceutical composition contains no more than 2% wt of total impurity when in use after stored at room temperature or ambient conditions for at least 60 days. In some embodiments, the hydrocortisone liquid pharmaceutical composition contains no more than 2% wt of total impurity when in use after stored at room temperature or ambient conditions for at least 90 days. In some embodiments, the hydrocortisone liquid pharmaceutical composition contains no more than 2% wt of total impurity when in use after stored at room temperature or ambient conditions for at least 120 days.

In some embodiments, a hydrocortisone liquid pharmaceutical composition described herein contains no more than 1% wt of total impurity when in use after stored at room temperature or ambient conditions for at least 15 days, 30 days, 60 days, 90 days, or 120 days. In some embodiments, the hydrocortisone liquid pharmaceutical composition contains no more than 1% wt of total impurity when in use after stored at room temperature or ambient conditions for at least 15 days. In some embodiments, the hydrocortisone liquid pharmaceutical composition contains no more than 1% wt of total impurity when in use after stored at room temperature or ambient conditions for at least 30 days. In some embodiments, the hydrocortisone liquid pharmaceutical composition contains no more than 1% wt of total impurity when in use after stored at room temperature or ambient conditions for at least 60 days. In some embodiments, the hydrocortisone liquid pharmaceutical composition contains no more than 1% wt of total impurity when in use after stored at room temperature or ambient conditions for at least 90 days. In some embodiments, the hydrocortisone liquid pharmaceutical composition contains no more than 1% wt of total impurity when in use after stored at room temperature or ambient conditions for at least 120 days.

In some embodiments, a hydrocortisone liquid pharmaceutical composition described herein retains at least 95% wt of the initial hydrocortisone amount when in use after stored at room temperature or ambient conditions for at least 15 days, 30 days, 60 days, 90 days, or 120 days. In some embodiments, the hydrocortisone liquid pharmaceutical composition retains at least 95% wt of the initial hydrocortisone amount when in use after stored at room temperature or ambient conditions for at least 15 days. In some embodiments, the hydrocortisone liquid pharmaceutical composition retains at least 95% wt of the initial hydrocortisone amount when in use after stored at room temperature or ambient conditions for at least 30 days. In some embodiments, the hydrocortisone liquid pharmaceutical composition retains at least 95% wt of the initial hydrocortisone amount when in use after stored at room temperature or ambient conditions for at least 60 days. In some embodiments, the hydrocortisone liquid pharmaceutical composition retains at least 95% wt of the initial hydrocortisone amount when in use after stored at room temperature or ambient conditions for at least 90 days. In some embodiments, the hydrocortisone liquid pharmaceutical composition retains at least 95% wt of the initial hydrocortisone amount when in use after stored at room temperature or ambient conditions for at least 120 days.

In some embodiments, a hydrocortisone liquid pharmaceutical composition described herein retains at least 98% wt of the initial hydrocortisone amount when in use after stored at room temperature or ambient conditions for at least 15 days, 30 days, 60 days, 90 days, or 120 days. In some embodiments, the hydrocortisone liquid pharmaceutical composition retains at least 98% wt of the initial hydrocortisone amount when in use after stored at room temperature or ambient conditions for at least 15 days. In some embodiments, the hydrocortisone liquid pharmaceutical composition retains at least 98% wt of the initial hydrocortisone amount when in use after stored at room temperature or ambient conditions for at least 30 days. In some embodiments, the hydrocortisone liquid pharmaceutical composition retains at least 98% wt of the initial hydrocortisone amount when in use after stored at room temperature or ambient conditions for at least 60 days. In some embodiments, the hydrocortisone liquid pharmaceutical composition retains at least 98% wt of the initial hydrocortisone amount when in use after stored at room temperature or ambient conditions for at least 90 days. In some embodiments, the hydrocortisone liquid pharmaceutical composition retains at least 98% wt of the initial hydrocortisone amount when in use after stored at room temperature or ambient conditions for at least 120 days.

In some embodiments, a hydrocortisone liquid pharmaceutical composition described herein are stable when in use after stored at accelerated conditions for at least 15 days, 30 days, 60 days, or 90 days.

In some embodiments, a hydrocortisone liquid pharmaceutical composition described herein contains no more than 2% wt of total impurity when in use after stored at accelerated conditions for at least 15 days, 30 days, 60 days, or 90 days. In some embodiments, the hydrocortisone liquid pharmaceutical composition contains no more than 2% wt of total impurity when in use after stored at accelerated conditions for at least 15 days. In some embodiments, the hydrocortisone liquid pharmaceutical composition contains no more than 2% wt of total impurity when in use after stored at accelerated conditions for at least 30 days. In some embodiments, the hydrocortisone liquid pharmaceutical composition contains no more than 2% wt of total impurity when in use after stored at accelerated conditions for at least 60 days. In some embodiments, the hydrocortisone liquid pharmaceutical composition contains no more than 2% wt of total impurity when in use after stored at accelerated conditions for at least 90 days.

In some embodiments, a hydrocortisone liquid pharmaceutical composition described herein contains no more than 1% wt of total impurity when in use after stored at accelerated conditions for at least 15 days, 30 days, 60 days, or 90 days. In some embodiments, the hydrocortisone liquid pharmaceutical composition contains no more than 1% wt of total impurity when in use after stored at accelerated conditions for at least 15 days. In some embodiments, the hydrocortisone liquid pharmaceutical composition contains no more than 1% wt of total impurity when in use after stored at accelerated conditions for at least 30 days. In some embodiments, the hydrocortisone liquid pharmaceutical composition contains no more than 1% wt of total impurity when in use after stored at accelerated conditions for at least 60 days. In some embodiments, the hydrocortisone liquid pharmaceutical composition contains no more than 1% wt of total impurity when in use after stored at accelerated conditions for at least 90 days.

In some embodiments, a hydrocortisone liquid pharmaceutical composition described herein retains at least 95% wt of the initial hydrocortisone amount when in use after stored at accelerated conditions for at least 15 days, 30 days, 60 days, or 90 days. In some embodiments, the hydrocortisone liquid pharmaceutical composition retains at least 95% wt of the initial hydrocortisone amount when in use after stored at accelerated conditions for at least 15 days. In some embodiments, the hydrocortisone liquid pharmaceutical composition retains at least 95% wt of the initial hydrocortisone amount when in use after stored at accelerated conditions for at least 30 days. In some embodiments, the hydrocortisone liquid pharmaceutical composition retains at least 95% wt of the initial hydrocortisone amount when in use after stored at accelerated conditions for at least 60 days. In some embodiments, the hydrocortisone liquid pharmaceutical composition retains at least 95% wt of the initial hydrocortisone amount when in use after stored at accelerated conditions for at least 90 days.

In some embodiments, a hydrocortisone liquid pharmaceutical composition described herein retains at least 98% wt of the initial hydrocortisone amount when in use after stored at accelerated conditions for at least 15 days, 30 days, 60 days, or 90 days. In some embodiments, the hydrocortisone liquid pharmaceutical composition retains at least 98% wt of the initial hydrocortisone amount when in use after stored at accelerated conditions for at least 15 days. In some embodiments, the hydrocortisone liquid pharmaceutical composition retains at least 98% wt of the initial hydrocortisone amount when in use after stored at accelerated conditions for at least 30 days. In some embodiments, the hydrocortisone liquid pharmaceutical composition retains at least 98% wt of the initial hydrocortisone amount when in use after stored at accelerated conditions for at least 60 days. In some embodiments, the hydrocortisone liquid pharmaceutical composition retains at least 98% wt of the initial hydrocortisone amount when in use after stored at accelerated conditions for at least 90 days.

Refrigerated Condition, Room Temperature, Accelerated Conditions, Temperature Excursions Refrigerated temperature, also as defined by the USP, is between 2 and 8 degrees Celsius, and is sometimes designated by the nominal value of 5 degrees Celsius. In some embodiments, refrigerated temperatures can be defined as 5±3° C. In each case, the formulations described in the present disclosure that were shown to be stable showed acceptable recovery of the expected hydrocortisone from the dose, where acceptable is >95% or alternately >90% of the nominal or starting dose of hydrocortisone, as well as maintaining acceptably constant therapeutic potential. Refrigerated conditions include temperature and/or relative humidity (RH) in typical refrigeration units (e.g., 5±3° C.). In some instances, a refrigerated condition is about 2° C., about 3° C., about 4° C., about 5° C., about 6° C., about 7° C., or about 8° C. In some instances, a refrigerated condition is about 2° C. to about 8° C.

As used herein, the term "room temperature," "ambient conditions," or "ambient temperature" refers to room temperature or "controlled room temperature". In some embodiments, the room temperatures are about 15° C. to about 25° C. In some embodiments, the room temperatures are about 15° C. to about 30° C. In some embodiments, the room temperatures are 25±5° C. In some embodiments, the controlled room temperatures are about 20° C. to about 25° C. In some embodiments, ambient conditions are about 15° C. to about 30° C. In some embodiments, ambient conditions are about 25±5° C. and 60±5% RH. In some embodiments, ambient conditions are about 25±2° C. and 60±5% RH. In some embodiments, the room temperature is about 25° C. and about 60% RH. In some instances, a room temperature or ambient temperature is at about 20° C., about 21° C., about 22° C., about 23° C., about 24° C., about 25° C., about 26° C., about 27° C., about 28° C., about 29° C., and about 30° C. In other instances, an ambient condition is about 55% RH, about 60% RH, or about 65% RH.

As used herein, the term "temperature excursions" or "temperature excursion" refers to a deviation from a predetermined condition, such as a deviation from a "controlled room temperature." In some instances, the deviation is about ±5° C., ±6° C., ±7° C., ±8° C., ±9° C., ±10° C. from the controlled room temperature. In some instances, the deviation is about ±5° C. from the controlled room temperature.

In some instances, temperature excursion for controlled room temperature is about 15° C. to about 30° C. In some instances, the temperature excursion takes place less than 1%, 2%, 3%, 4%, 5%, 10%, 15%, 20%, 30%, 40%, or 50% of the time during the entire period when the liquid pharmaceutical composition is measured for stability.

Accelerated conditions for the hydrocortisone oral liquid formulations described herein include temperature and/or relative humidity (RH) that are at or above ambient levels or room temperature (e.g. 25±5° C.; 55±10% RH). In some instances, an accelerated condition is at about 25° C., about 30° C., about 35° C., about 40° C., about 45° C., about 50° C., about 55° C. or about 60° C. In other instances, an accelerated condition is above 55% RH, about 65% RH, about 70% RH, about 75% RH or about 80% RH. In further instances, an accelerated condition is about 40° C.±2° C. and 60±5% RH. In other instances, an accelerated condition is about 40° C.±2° C. and 65±5% RH. In yet further instances, an accelerated condition is about 40° C.±2° C. at 75±5% RH humidity.

Non-Aqueous Liquid Carrier in the Hydrocortisone Oral Liquid Formulations

In some embodiments, hydrocortisone oral liquid formulations described herein comprise a non-aqueous liquid carrier. The non-aqueous liquid carrier can include oils (e.g., edible vegetable oils or synthetic edible oils), propylene glycol, glycerin, polypropylene glycol, polyethylene glycol (PEG), alcohol (e.g., ethanol), or any combinations thereof. In some embodiments, hydrocortisone oral liquid formulations described herein comprise polyoxylglycerides (e.g., caprylocaproyl polyoxyl-8 glycerides, sold under the trade name Labrasol®). In some embodiments, hydrocortisone oral liquid formulations described herein does not comprises added water.

In some embodiments, the non-aqueous liquid carrier can include an edible vegetable oil, such as soybean oil, partially hydrogenated soybean oil, corn oil, sunflower oil, or peanut oil. In some instances, non-aqueous liquid carriers are commercially available synthetic edible oils that are equivalent to the vegetable oils. For example, the triglycerides of the $C_8$-$C_{10}$ fatty acids of fractionated coconut oil are available under the trade name of "Miglyol." Specifically, Miglyol is a triglyceride of capric and caprylic acids with glycerol. The oils can also include sugar fatty acids known as "Olestras."

In some embodiments, the non-aqueous liquid carrier is present in a hydrocortisone oral liquid formulation described herein in an amount of from about 50% wt to about 99.9% wt. In some embodiments, the non-aqueous liquid carrier is present in the hydrocortisone oral liquid formulation in an amount of from about 50% wt to about 60% wt, about 60% wt to about 70% wt, about 70% wt to about 80% wt, about 80% wt to about 90% wt, about 90% wt to about 95% wt, about 95% wt to about 96% wt, about 96% wt to about 97% wt, about 97% wt to about 98% wt, about 98% wt to about 99% wt, about 99% wt to about 99.5% wt, or about 99.5% wt to about 99.9% wt. In some embodiments, the non-aqueous liquid carrier is present in the hydrocortisone oral liquid formulation in an amount of from about 70% wt to about 99.9% wt. In some embodiments, the non-aqueous liquid carrier is present in the hydrocortisone oral liquid formulation in an amount of from about 80% wt to about 99.9% wt. In some embodiments, the non-aqueous liquid carrier is present in the hydrocortisone oral liquid formulation in an amount of from about 90% wt to about 99.5% wt. In some embodiments, the non-aqueous liquid carrier is present in the hydrocortisone oral liquid formulation in an amount of from about 95% wt to about 99.5% wt. In some embodiments, the non-aqueous liquid carrier is present in the hydrocortisone oral liquid formulation in an amount of from about 97% wt to about 99.5% wt. In some embodiments, the non-aqueous liquid carrier is present in the hydrocortisone oral liquid formulation in an amount of about 95% wt. In some embodiments, the non-aqueous liquid carrier is present in the hydrocortisone oral liquid formulation in an amount of about 96% wt. In some embodiments, the non-aqueous liquid carrier is present in the hydrocortisone oral liquid formulation in an amount of about 97% wt. In some embodiments, the non-aqueous liquid carrier is present in the hydrocortisone oral liquid formulation in an amount of about 97% wt. In some embodiments, the non-aqueous liquid carrier is present in the hydrocortisone oral liquid formulation in an amount of about 98% wt. In some embodiments, the non-aqueous liquid carrier is present in the hydrocortisone oral liquid formulation in an amount of about 98.5% wt. In some embodiments, the non-aqueous liquid carrier is present in the hydrocortisone oral liquid formulation in an amount of about 99% wt. In some embodiments, the non-aqueous liquid carrier is present in the hydrocortisone oral liquid formulation in an amount of about 99.5% wt. In some embodiments, the non-aqueous liquid carrier comprises propylene glycol, PEG 400 and glycerin.

In some embodiments, the non-aqueous liquid carrier comprises propylene glycol. In some embodiments, the non-aqueous liquid carrier is glycerin. In some embodiments, the non-aqueous liquid carrier is alcohol, such as ethyl alcohol or ethanol. In some embodiments, the non-aqueous liquid carrier is PEG. In some embodiments, the PEG has an average molecular weight of about 200 to about 10,000 g/mol. In some embodiments, the PEG has an average molecular weight of about 200 to about 500 g/mol, about 500 to about 1000 g/mol, about 1000 to about 5000 g/mol, about 5000 to about 10,000 g/mol. In some embodiments, the PEG has an average molecular weight of about 200 to about 500 g/mol. In some embodiments, the PEG has an average molecular weight of about 300 to about 500 g/mol. In some embodiments, the PEG has an average molecular weight of about 350 to about 450 g/mol. In some embodiments, the PEG has an average molecular weight of about 400 g/mol. In some embodiments, the PEG has a number average molecular weight of about 200 to about 10,000 g/mol. In some embodiments, the PEG has a number average molecular weight of about 200 to about 500 g/mol, about 500 to about 1000 g/mol, about 1000 to about 5000 g/mol, about 5000 to about 10,000 g/mol. In some embodiments, the PEG has a number average molecular weight of about 200 to about 500 g/mol. In some embodiments, the PEG has a number average molecular weight of about 300 to about 500 g/mol. In some embodiments, the PEG has a number average molecular weight of about 350 to about 450 g/mol. In some embodiments, the PEG has a number average molecular weight of about 400 g/mol. In some embodiments, the PEG is PEG 400.

In some embodiments, the non-aqueous liquid carrier comprises a combination of alcohol (e.g., ethanol) and glycerin. In some embodiments, the combination of ethanol and glycerin is in a weight ratio of about 3:97 to about 30:70. In some embodiments, the combination of ethanol and glycerin is in a weight ratio of about 4:96 to about 20:80. In some embodiments, the combination of ethanol and glycerin is in a weight ratio of about 5:95 to about 10:90. In some embodiments, the combination of ethanol and glycerin is in a weight ratio of about 5:95.

In some embodiments, the non-aqueous liquid carrier comprises a combination of propylene glycol and glycerin. In some embodiments, the combination of propylene glycol and glycerin is in a weight ratio of about 7:93 to about 30:70. In some embodiments, the combination of propylene glycol and glycerin is in a weight ratio of about 8:92 to about 20:80. In some embodiments, the combination of propylene glycol and glycerin is in a weight ratio of about 9:91 to about 15:85. In some embodiments, the combination of propylene glycol and glycerin is in a weight ratio of about 10:90.

In some embodiments, the non-aqueous liquid carrier comprises a combination of propylene glycol and PEG 400. In some embodiments, the combination of propylene glycol and PEG 400 is in a weight ratio of about 3:97 to about 30:70. In some embodiments, the combination of propylene glycol and PEG 400 is in a weight ratio of about 5:95 to about 20:80. In some embodiments, the combination of propylene glycol and PEG 400 is in a weight ratio of about 5:95 to about 10:90. In some embodiments, the combination of propylene glycol and PEG 400 is in a weight ratio of about 5:95. In some embodiments, the combination of propylene glycol and PEG 400 is in a weight ratio of about 10:90.

In some embodiments, the non-aqueous liquid carrier comprises a combination of PEG and glycerin. In some embodiments, the combination of PEG and glycerin is in a weight ratio of about 10:90 to about 80:20. In some embodiments, the combination of PEG and glycerin is in a weight ratio of about 20:80 to about 70:30. In some embodiments, the combination of PEG and glycerin is in a weight ratio of about 25:75 to about 60:40. In some embodiments, the combination of PEG and glycerin is in a weight ratio of about 30:70 to about 50:50. In some embodiments, the combination of PEG and glycerin is in a weight ratio of about 30:70. In some embodiments, the combination of PEG and glycerin is in a weight ratio of about 50:50.

In some embodiments, the non-aqueous liquid carrier comprises a combination of propylene glycol, PEG, and glycerin. In some embodiments, the combination of propylene glycol, PEG, and glycerin is in a weight ratio of about 2:10:88 to about 10:70:30. In some embodiments, the combination of propylene glycol, PEG, and glycerin is in a weight ratio of about 3:15:82 to about 9:60:31. In some embodiments, the combination of propylene glycol, PEG, and glycerin is in a weight ratio of about 4:20:86 to about 7:55:43. In some embodiments, the combination of propylene glycol, PEG, and glycerin is in a weight ratio of about 5:25:70 to about 5:50:45. In some embodiments, the combination of propylene glycol, PEG, and glycerin is in a weight ratio of about 5:25:70. In some embodiments, the combination of propylene glycol, PEG, and glycerin is in a weight ratio of about 5:50:45. In some embodiments, the PEG is PEG 400.

In some embodiments, the non-aqueous liquid carrier is present in the liquid pharmaceutical composition in an amount of about 0.01% w/v to about 99.9% w/v. In other embodiments, the non-aqueous liquid carrier is present in the liquid pharmaceutical composition in an amount of about 0.01% w/v to about 0.1% w/v, about 0.1% w/v to about 1% w/v, about 1% w/v to about 5% w/v, about 5% w/v to about 10% w/v, about 10% w/v to about 15% w/v, about 15% w/v to about 20% w/v, about 20% w/v to about 30% w/v, about 30% w/v to about 40% w/v, about 40% w/v to about 50% w/v, about 50% w/v to about 60% w/v, about 60% w/v to about 70% w/v, about 70% w/v to about 80% w/v, about 80% w/v to about 90% w/v, about 90% w/v to about 95% w/v, about 95% w/v to about 98% w/v, about 98% w/v to about 99% w/v, or about 99% w/v to about 99.9% w/v. In some embodiments, the non-aqueous liquid carrier is present in the liquid pharmaceutical composition in an amount of about 99% w/v to about 99.9% w/v. In some embodiments, the non-aqueous liquid carrier is present in the liquid pharmaceutical composition in an amount of about 25% w/v to about 120% w/v. In some embodiments, the non-aqueous liquid carrier is present in the liquid pharmaceutical composition in an amount of about 80% w/v to about 110% w/v. In some embodiments, the non-aqueous liquid carrier is present in the liquid pharmaceutical composition in an amount of about 100% w/v to about 120% w/v. In some embodiments, the non-aqueous liquid carrier is present in the liquid pharmaceutical composition in an amount of about 110% w/v to about 120% w/v. In some embodiments, the non-aqueous liquid carrier comprises PEG 400, propylene glycol, and glycerin.

In some embodiments, PEG is present in the liquid pharmaceutical composition in an amount of about 20% to about 80% w/v. In some embodiments, PEG is present in the liquid pharmaceutical composition in an amount of about 20% to about 25% w/v, about 25% to about 30% w/v, about 30% to about 35% w/v, about 35% to about 40% w/v, about 40% to about 45% w/v, about 45% to about 50% w/v, about 50% to about 55% w/v, about 55% to about 60% w/v, about 60% to about 65% w/v, about 65% to about 70% w/v, about 70% to about 75% w/v, or about 75% to about 80% w/v. In some embodiments, PEG is present in the liquid pharmaceutical composition in an amount of about 40% to about 60% w/v. In some embodiments, PEG is present in the liquid pharmaceutical composition in an amount of about 45% to about 55% w/v. In some embodiments, PEG is present in the liquid pharmaceutical composition in an amount of about 50% w/v. In some embodiments, the PEG is PEG 400. In some embodiments, PEG 400 is present in the liquid pharmaceutical composition in an amount of about 45% to about 55% w/v. In some embodiments, PEG 400 is present in the liquid pharmaceutical composition in an amount of about 50% w/v.

In some embodiments, PEG is present in the liquid pharmaceutical composition in an amount of about 20% to about 80% wt. In some embodiments, PEG is present in the liquid pharmaceutical composition in an amount of about 20% to about 25% wt, about 25% to about 30% wt, about 30% to about 35% wt, about 35% to about 40% wt, about 40% to about 45% wt, about 45% to about 50% wt, about 50% to about 55% wt, about 55% to about 60% wt, about 60% to about 65% wt, about 65% to about 70% wt, about 70% to about 75% wt, or about 75% to about 80% wt. In some embodiments, PEG is present in the liquid pharmaceutical composition in an amount of about 20% to about 50% wt. In some embodiments, PEG is present in the liquid pharmaceutical composition in an amount of about 30% to about 45% wt. In some embodiments, PEG is present in the liquid pharmaceutical composition in an amount of about 40% wt. In some embodiments, PEG is present in the liquid pharmaceutical composition in an amount of about 42% wt. In some embodiments, the PEG is PEG 400. In some embodiments, PEG 400 is present in the liquid pharmaceutical composition in an amount of about 25% to about 35% wt. In some embodiments, PEG 400 is present in the liquid pharmaceutical composition in an amount of about 33% wt.

In some embodiments, propylene glycol is present in the liquid pharmaceutical composition in an amount of about 0.1% to about 20% w/v. In some embodiments, propylene glycol is present in the liquid pharmaceutical composition in an amount of about 0.1% to about 1% w/v, about 1% to about 2% w/v, about 2% to about 3% w/v, about 3% to about 4% w/v, about 4% to about 5% w/v, about 5% to about 6% w/v, about 6% to about 7% w/v, about 7% to about 10% w/v, about 10% to about 15% w/v, or about 15% to about 20% w/v. In some embodiments, propylene glycol is present in the liquid pharmaceutical composition in an amount of about 0.5% to about 10% w/v. In some embodiments, propylene glycol is present in the liquid pharmaceutical composition in an amount of about 2% to about 8% w/v. In some embodiments, propylene glycol is present in the liquid pharmaceutical composition in an amount of about 4% to about 6% w/v. In some embodiments, propylene glycol is present in the liquid pharmaceutical composition in an amount of about 5% w/v.

In some embodiments, propylene glycol is present in the liquid pharmaceutical composition in an amount of about 0.1% to about 20% wt. In some embodiments, propylene glycol is present in the liquid pharmaceutical composition in an amount of about 0.1% to about 1% wt, about 1% to about 2% wt, about 2% to about 3% wt, about 3% to about 4% wt, about 4% to about 5% wt, about 5% to about 6% wt, about 6% to about 7% wt, about 7% to about 10% wt, about 10% to about 15% wt, or about 15% to about 20% wt. In some embodiments, propylene glycol is present in the liquid pharmaceutical composition in an amount of about 0.5% to about 10% wt. In some embodiments, propylene glycol is present in the liquid pharmaceutical composition in an amount of about 2% to about 8% wt. In some embodiments, propylene glycol is present in the liquid pharmaceutical composition in an amount of about 3% to about 5% wt. In some embodiments, propylene glycol is present in the liquid pharmaceutical composition in an amount of about 4.2% wt.

In some embodiments, glycerin is present in the liquid pharmaceutical composition in an amount of about 20% to about 90% w/v. In some embodiments, glycerin is present in the liquid pharmaceutical composition in an amount of about 20% to about 25% w/v, about 25% to about 30% w/v, about 30% to about 35% w/v, about 35% to about 40% w/v, about 40% to about 45% w/v, about 45% to about 50% w/v, about 50% to about 55% w/v, about 55% to about 60% w/v, about 60% to about 65% w/v, about 65% to about 70% w/v, about 70% to about 75% w/v, or about 75% to about 90% w/v. In some embodiments, glycerin is present in the liquid pharmaceutical composition in an amount of about 40% to about 80% w/v. In some embodiments, glycerin is present in the liquid pharmaceutical composition in an amount of about 50% to about 70% w/v. In some embodiments, glycerin is present in the liquid pharmaceutical composition in an amount of about 60% to about 65% w/v. In some embodiments, glycerin is present in the liquid pharmaceutical composition in an amount of about 62% w/v. In some embodiments, glycerin is present in the liquid pharmaceutical composition in an amount of about 62.2% w/v.

In some embodiments, glycerin is present in the liquid pharmaceutical composition in an amount of about 20% to about 90% wt. In some embodiments, glycerin is present in the liquid pharmaceutical composition in an amount of about 20% to about 25% wt, about 25% to about 30% wt, about 30% to about 35% wt, about 35% to about 40% wt, about 40% to about 45% wt, about 45% to about 50% wt, about 50% to about 55% wt, about 55% to about 60% wt, about 60% to about 65% wt, about 65% to about 70% wt, about 70% to about 75% wt, or about 75% to about 90% wt. In some embodiments, glycerin is present in the liquid pharmaceutical composition in an amount of about 30% to about 80% wt. In some embodiments, glycerin is present in the liquid pharmaceutical composition in an amount of about 40% to about 60% wt. In some embodiments, glycerin is present in the liquid pharmaceutical composition in an amount of about 45% to about 55% wt. In some embodiments, glycerin is present in the liquid pharmaceutical composition in an amount of about 50% to about 70% wt. In some embodiments, glycerin is present in the liquid pharmaceutical composition in an amount of about 45% wt. In some embodiments, glycerin is present in the liquid pharmaceutical composition in an amount of about 50% wt. In some embodiments, glycerin is present in the liquid pharmaceutical composition in an amount of about 52.3% wt. In some embodiments, glycerin is present in the liquid pharmaceutical composition in an amount of about 60% wt. In some embodiments, glycerin is present in the liquid pharmaceutical composition in an amount of about 65% wt.

In some embodiment, the non-aqueous liquid carrier is a combination of glycerin, PEG 400, and propylene glycol. In some embodiment, glycerin is present in the liquid pharmaceutical composition in an amount of about 43.5% w/v, propylene glycol is present in the liquid pharmaceutical composition in an amount of about 5% w/v, and PEG 400 is present in the liquid pharmaceutical composition in an amount of about 50% w/v.

Preservative in the Hydrocortisone Oral Liquid Formulations

In some embodiments, hydrocortisone oral liquid formulations described herein comprise a preservative. Preservatives can include anti-microbials, antioxidants, chelating agents, and other agents that enhance sterility, such that a low bioburden is maintained in the formulation of the invention from preparation through storage, and during routine use by patients and clinicians. Exemplary preservatives include ascorbic acid, ascorbyl palmitate, BHA, BHT, citric acid, EDTA and its salts, erythorbic acid, fumaric acid, malic acid, propyl gallate, sodium ascorbate, sodium bisulfate, sodium metabisulfite, sodium sulfite, parabens (such as methylparaben, ethylparaben, propylparaben, butylparaben and their salts), benzoic acid, sodium benzoate, potassium sorbate, vanillin, and the like.

In some embodiments, the preservative comprises an antimicrobial agent, a chelating agent, an antioxidant, or a combination thereof. In some embodiments, the preservative comprises an antimicrobial agent. In some embodiments, the preservative comprises a chelating agent. In some embodiments, the preservative comprises an antioxidant. In some embodiments, the preservative comprises an antimicrobial agent and an antioxidant. In some embodiments, the preservative comprises an antimicrobial agent, a chelating agent, and an antioxidant.

In some embodiments, the preservative is present in the liquid pharmaceutical composition in an amount of about 0.01% to about 30% w/v. In some embodiments, the preservative is present in the liquid pharmaceutical composition in an amount of about 0.01% to about 0.1% w/v, about 0.1% to about 0.5% w/v, about 0.5% to about 1% w/v, about 1% to about 5% w/v, about 5% to about 10% w/v, about 10% to about 15% w/v, about 15% to about 20% w/v, about 20% to about 25% w/v, or about 25% to about 30% w/v. In some embodiments, the preservative is present in the liquid pharmaceutical composition in an amount of about 0.05% to about 1% w/v. In some embodiments, the preservative is present in the liquid pharmaceutical composition in an amount of about 0.1% to about 0.5% w/v. In some embodiments, the preservative is present in the liquid pharmaceutical composition in an amount of about 0.2% to about 0.25% w/v. In some embodiments, the preservative is present in the liquid pharmaceutical composition in an amount of about 0.21% w/v.

In some embodiments, the preservative is present in the liquid pharmaceutical composition in an amount of about 0.01% to about 30% wt. In some embodiments, the preservative is present in the liquid pharmaceutical composition in an amount of about 0.01% to about 0.1% wt, about 0.1% to about 0.5% wt, about 0.5% to about 1% wt, about 1% to about 5% wt, about 5% to about 10% wt, about 10% to about 15% wt, about 15% to about 20% wt, about 20% to about 25% wt, or about 25% to about 30% wt. In some embodiments, the preservative is present in the liquid pharmaceutical composition in an amount of about 0.05% to about 1% wt. In some embodiments, the preservative is present in the liquid pharmaceutical composition in an amount of about 0.1% to about 0.5% wt. In some embodiments, the preservative is present in the liquid pharmaceutical composition in an amount of about 0.15% to about 0.2% wt. In some embodiments, the preservative is present in the liquid pharmaceutical composition in an amount of about 0.175% wt. In some embodiments, the preservative is present in the liquid pharmaceutical composition in an amount of about 0.18% wt. In some embodiments, the preservative comprises butylated hydroxyanisole (BHA), methyl paraben and propyl paraben.

In some embodiments, the preservative comprises an antimicrobial agent. In some embodiments, the antimicrobial agent is a paraben or a mixture of parabens, benzoic acid or a pharmaceutically acceptable salt thereof, sorbic acid or a pharmaceutically acceptable salt thereof, phenoxyethanol, benzyl alcohol, propionic acid, or a combination thereof. In some embodiments, the antimicrobial agent is a paraben or a mixture of parabens. In some embodiments, the antimicrobial agent is a paraben or a mixture of parabens. In some embodiments, the antimicrobial agent is a paraben, such as methyl paraben, ethyl paraben, propyl paraben, or a combination thereof. In some embodiments, the antimicrobial agent is methyl paraben. In some embodiments, the antimicrobial agent is propyl paraben. In some embodiments, the antimicrobial agent is a mixture of methyl paraben and propyl paraben.

In some embodiments, an antimicrobial agent is present in the liquid pharmaceutical composition in an amount of about 0.01% to about 10% w/v. In some embodiments, the antimicrobial agent is present in the liquid pharmaceutical composition in an amount of about 0.01% to about 0.1% w/v, about 0.1% to about 0.5% w/v, about 0.5% to about 1% w/v, about 1% to about 5% w/v, or about 5% to about 10% w/v. In some embodiments, the antimicrobial agent is present in the liquid pharmaceutical composition in an amount of about 0.05% to about 1% w/v. In some embodiments, the antimicrobial agent is present in the liquid pharmaceutical composition in an amount of about 0.1% to about 0.5% w/v.

In some embodiments, the antimicrobial agent is present in the liquid pharmaceutical composition in an amount of about 0.2% to about 0.25% w/v. In some embodiments, the antimicrobial agent is present in the liquid pharmaceutical composition in an amount of about 0.20% w/v. In some embodiments, the antimicrobial agent is a mixture of methyl paraben and propyl paraben. In some embodiments, the antimicrobial agent is a mixture of parabens or salts thereof.

In some embodiments, the mixture of parabens or salts thereof (e.g., methyl paraben and propyl paraben) is present in the liquid pharmaceutical composition in an amount of about 0.1% w/v to about 1% w/v. In some embodiments, the mixture of parabens or salts thereof (e.g., methyl paraben and propyl paraben) is present in the liquid pharmaceutical composition in an amount of about 0.1% w/v to about 0.15% w/v, about 0.15% w/v to about 0.2% w/v, about 0.2% w/v to about 0.25% w/v, about 0.25% w/v to about 0.3% w/v, about 0.3% w/v to about 0.5% w/v, or about 0.5% w/v to about 1% w/v. In some embodiments, the mixture of methyl paraben and propyl paraben is present in the liquid pharmaceutical composition in an amount of about 0.1% w/v to about 0.3% w/v. In some embodiments, the mixture of methyl paraben and propyl paraben is present in the liquid pharmaceutical composition in an amount of about 0.2% w/v.

In some embodiments, methyl paraben is present in the liquid pharmaceutical composition in an amount of about 0.05% w/v to about 0.3% w/v. In other embodiments, methyl paraben is present in the liquid pharmaceutical composition in an amount of about 0.05% w/v to about 0.08% w/v, about 0.08% w/v to about 0.15% w/v, about 0.15% w/v to about 0.17% w/v, about 0.17% w/v to about 0.19% w/v, about 0.20% w/v to about 0.25% w/v, or about 0.25% to about 0.3% w/v. In some embodiments, methyl paraben is present in the liquid pharmaceutical composition in an amount of about 0.18% w/v.

In some embodiments, propyl paraben is present in the liquid pharmaceutical composition in an amount of about 0.001% w/v to about 0.05% w/v. In other embodiments, propyl paraben is present in the liquid pharmaceutical composition in an amount of about 0.001% w/v to about 0.005% w/v, about 0.005% w/v to about 0.01% w/v, about 0.01% w/v to about 0.02% w/v, about 0.02% w/v to about 0.03% w/v, or about 0.03% w/v to about 0.05% w/v. In some embodiments, propyl paraben is present in the liquid pharmaceutical composition in an amount of about 0.02% w/v.

In some embodiments, methyl paraben and propyl paraben are present in an amount sufficient to provide antimicrobial effectiveness to the hydrocortisone liquid pharmaceutical composition described herein.

In some embodiments, the preservative comprises an antioxidant. In some embodiments, the antioxidant is vitamin A, monothioglycerol, ascorbic acid, sodium bisulfite, sodium sulfite, α-Tocopherol acetate (vitamin E), butylated hydroxyanisole (BHA), butylated hydroxytoluene (BHT), or a combination thereof. In some embodiments, the antioxidant is butylated hydroxyanisole (BHA). In some embodiments, the antioxidant is butylated hydroxytoluene (BHT). In some embodiments, the antioxidant is butylated hydroxyanisole (BHA) and butylated hydroxytoluene (BHT).

In some embodiments, an antioxidant is present in the liquid pharmaceutical composition in an amount of about 0.001% w/v to about 0.5% w/v. In other embodiments, the antioxidant is present in the liquid pharmaceutical composition in an amount of about 0.001% w/v to about 0.005% w/v, about 0.005% w/v to about 0.007% w/v, about 0.007% w/v to about 0.01% w/v, about 0.01% w/v to about 0.011% w/v, about 0.011% w/v to about 0.015% w/v, about 0.015% w/v to about 0.02% w/v, about 0.02% w/v to about 0.03% w/v, about 0.03% w/v to about 0.05% w/v, about 0.05% w/v to about 0.1% w/v, or about 0.1% w/v to about 0.5% w/v. In some embodiments, the antioxidant is present in the liquid pharmaceutical composition in an amount of about 0.005% w/v to about 0.05% w/v. In some embodiments, the antioxidant is present in the liquid pharmaceutical composition in an amount of about 0.008% w/v to about 0.02% w/v. In some embodiments, the antioxidant is present in the liquid pharmaceutical composition in an amount of about 0.01% w/v. In some embodiments, the antioxidant is BHA. In some embodiments, the antioxidant is BHT.

In some embodiments, BHA is present in the liquid pharmaceutical composition in an amount of about 0.001% w/v to about 0.5% w/v. In other embodiments, BHA is present in the liquid pharmaceutical composition in an amount of about 0.001% w/v to about 0.005% w/v, about 0.005% w/v to about 0.008% w/v, about 0.008% w/v to about 0.01% w/v, about 0.01% w/v to about 0.015% w/v, about 0.015% w/v to about 0.02% w/v, about 0.02% w/v to about 0.03% w/v, about 0.03% w/v to about 0.05% w/v, about 0.05% w/v to about 0.1% w/v, or about 0.1% to about 0.5% w/v. In some embodiments, BHA is present in the liquid pharmaceutical composition in an amount of about 0.005% w/v to about 0.05% w/v. In some embodiments, BHA is present in the liquid pharmaceutical composition in an amount of about 0.01% w/v.

In some embodiments, the preservative comprises a chelating agent. In some embodiments, the chelating agent is disodium ethylenediaminetetraacetic acid, polyphosphates, citric acid, calcium disodium edetate, ethylenediaminetetraacetic acid (EDTA), or a combination thereof. In some embodiments, the chelating agent is EDTA.

In some embodiments, a chelating agent is present in the liquid pharmaceutical composition in an amount of about 0.001% w/v to about 5% w/v. In other embodiments, the chelating agent is present in the liquid pharmaceutical composition in an amount of about 0.001% w/v to about 0.005% w/v, about 0.005% w/v to about 0.01% w/v, about 0.01% w/v to about 0.05% w/v, about 0.05% w/v to about 0.1% w/v, about 0.1% w/v to about 0.5% w/v, about 0.5% w/v to about 1% w/v, about 1% w/v to about 2% w/v, or about 2% w/v to about 5% w/v. In some embodiments, the chelating agent is present in the liquid pharmaceutical composition in an amount of about 0.005% w/v to about 0.5% w/v. In some embodiments, the chelating agent is present in the liquid pharmaceutical composition in an amount of about 0.05% w/v to about 0.2% w/v. In some embodiments, the chelating agent is present in the liquid pharmaceutical composition in an amount of about 0.1% w/v. In some embodiments, the chelating agent is EDTA.

Sweetener and Flavoring Agents in the Hydrocortisone Oral Liquid Formulations

In some embodiments, hydrocortisone oral liquid formulations described herein comprise a flavoring agent. The flavoring agent or flavorant can be used to enhance the flavor or aroma of the dose, and to improve general palatability of the dose, thus helping to mask the flavor of the active pharmaceutical ingredient, which patients may find unpleasant. The flavoring agent can provide an improved experience for patients, and better compliance with the drug regimen desired by clinicians. Suitable natural or artificial flavors can be selected from pharmaceutically acceptable options as described in standard pharmacy references which are known to those skilled in the art. Suitable natural or synthetic flavoring agents can be selected from standard reference books, such as Remington: The Science and Practice of Pharmacy (2000) and Fenaroli's Handbook of Flavor Ingredients (1994).

In some embodiments, pharmaceutically acceptable flavors, such as (4-hydroxy-3-methoxybenzaldehyde (vanillin), methyl anthranilate (grape flavor), 3,5-Dimethyl-1,2-Cyclopentadione (caramel flavor), maltol, 4-(4-Hydroxyphenyl)butan-2-one (raspberry flavor), ethyl maltol, ethyl propionate (fruity flavor) and berry flavor, can be used to improve the flavor of hydrocortisone and other excipients in the formulation, and to enhance palatability and thus compliance in a range of patient populations. Natural and synthetic flavors can be used and adapted to the palate of diverse patient populations, including but not limited to, age- and culturally related flavor preferences (for example bubble gum flavor for pediatric patients). Non-limiting examples of suitable natural flavors, some of which can be readily simulated with synthetic agents or combinations thereof, include almond, anise, apple, apricot, banana, blackberry, blackcurrant, blueberry, caramel, cherry, chocolate, cinnamon, cranberry, grape, lemon, lime, orange, peppermint, pineapple, raspberry, spearmint, strawberry, vanilla, etc. In some embodiments, the flavors include which can be readily simulated with synthetic agents or combinations thereof include fat, poultry, fish, beef, and other meats. In some embodiments, berry flavor (e.g., Berry Mixed Flavor WONF, WS Natural 13.17579) is used. In some embodiments, ethyl maltol is used. The use of berry flavor or ethyl maltol has been found to be effective in helping to improve the palatability of hydrocortisone oral liquid solution. In other embodiments, both berry flavor and ethyl maltol are used in the liquid pharmaceutical composition described herein. In some embodiments, the flavoring agent comprises a natural flavoring agent, an artificial flavoring agent, or a combination thereof.

In some embodiments, a flavoring agent is present in the liquid pharmaceutical composition in an amount of about 0.001% w/v to about 5% w/v. In other embodiments, the flavoring agent is present in the liquid pharmaceutical composition in an amount of about 0.001% w/v to about 0.005% w/v, about 0.005% w/v to about 0.01% w/v, about 0.01% w/v to about 0.05% w/v, about 0.05% w/v to about 0.1% w/v, about 0.1% w/v to about 0.5% w/v, about 0.5% w/v to about 1% w/v, about 1% w/v to about 2% w/v, or about 2% w/v to about 5% w/v. In some embodiments, the flavoring agent is present in the liquid pharmaceutical composition in an amount of about 0.005% w/v to about 0.5% w/v. In some embodiments, the flavoring agent is present in the liquid pharmaceutical composition in an amount of about 0.01% w/v to about 0.1% w/v. In some embodiments, the flavoring agent is present in the liquid pharmaceutical composition in an amount of about 0.2% w/v to about 0.5% w/v. In some embodiments, the flavoring agent is present in the liquid pharmaceutical composition in an amount of about 0.4% w/v. In some embodiments, the flavoring agent is berry flavor. In some embodiments, the flavoring agent is ethyl maltol. In some embodiments, the flavoring agent is a combination of berry flavor and ethyl maltol.

In some embodiments, a flavoring agent is present in the liquid pharmaceutical composition in an amount of about 0.001% wt to about 5% wt. In other embodiments, the flavoring agent is present in the liquid pharmaceutical composition in an amount of about 0.001% wt to about 0.005% wt, about 0.005% wt to about 0.01% wt, about 0.01% wt to about 0.05% wt, about 0.05% wt to about 0.1% wt, about 0.1% wt to about 0.5% wt, about 0.5% wt to about 1% wt, about 1% wt to about 2% wt, or about 2% wt to about 5% wt. In some embodiments, the flavoring agent is present in the liquid pharmaceutical composition in an amount of about 0.005% wt to about 0.5% wt. In some embodiments, the flavoring agent is present in the liquid pharmaceutical composition in an amount of about 0.01% wt to about 0.1% wt. In some embodiments, the flavoring agent is present in the liquid pharmaceutical composition in an amount of about 0.1% wt to about 0.4% wt. In some embodiments, the flavoring agent is present in the liquid pharmaceutical composition in an amount of about 0.33% wt. In some embodiments, the flavoring agent is berry flavor. In some embodiments, the flavoring agent is ethyl maltol. In some embodiments, the flavoring agent is a combination of berry flavor and ethyl maltol.

In some embodiments, berry flavor is present in the liquid pharmaceutical composition in an amount of about 0.001% w/v to about 5% w/v. In other embodiments, berry flavor is present in the liquid pharmaceutical composition in an amount of about 0.001% w/v to about 0.005% w/v, about 0.005% w/v to about 0.01% w/v, about 0.01% w/v to about 0.05% w/v, about 0.05% w/v to about 0.1% w/v, about 0.1% w/v to about 0.5% w/v, about 0.5% w/v to about 1% w/v, about 1% w/v to about 2% w/v, or about 2% w/v to about 5% w/v. In some embodiments, berry flavor is present in the liquid pharmaceutical composition in an amount of about 0.005% w/v to about 0.5% w/v. In some embodiments, berry flavor is present in the liquid pharmaceutical composition in an amount of about 0.01% w/v to about 0.5% w/v. In some embodiments, berry flavor is present in the liquid pharmaceutical composition in an amount of about 0.2% w/v.

In some embodiments, ethyl maltol is present in the liquid pharmaceutical composition in an amount of about 0.001% w/v to about 5% w/v. In other embodiments, ethyl maltol is present in the liquid pharmaceutical composition in an amount of about 0.001% w/v to about 0.005% w/v, about 0.005% w/v to about 0.01% w/v, about 0.01% w/v to about 0.05% w/v, about 0.05% w/v to about 0.1% w/v, about 0.1% w/v to about 0.5% w/v, about 0.5% w/v to about 1% w/v, about 1% w/v to about 2% w/v, or about 2% w/v to about 5% w/v. In some embodiments, ethyl maltol is present in the liquid pharmaceutical composition in an amount of about 0.005% w/v to about 0.5% w/v. In some embodiments, ethyl maltol is present in the liquid pharmaceutical composition in an amount of about 0.05% w/v to about 0.5% w/v. In some embodiments, ethyl maltol is present in the liquid pharmaceutical composition in an amount of about 0.2% w/v. In some embodiments, ethyl maltol is present in the liquid pharmaceutical composition in an amount of about 0.1% w/v.

In some embodiments, hydrocortisone oral liquid formulations described herein comprise a sweetener. Sweeteners or sweetening agents can include any compounds that provide a sweet taste to enhance the palatability of the formulation, including natural and synthetic sugars and natural and synthetic sweeteners (i.e., non-sugar sweetening agents). Sweeteners can include glucose, fructose, sucrose, lactose, maltose or other pharmaceutically acceptable monosaccharides and disaccharides or sugar alcohols, such as xylitol, mannitol, lactitol, maltitol, or sorbitol. Also, sweeteners can include maltodextrin, polydextrose and the like. Other sweeteners can include glycerin, inulin, maltol, salts of acesulfame, alitame, aspartame, neotame, cyclamate salts, sucralose, sorbitol solution, saccharin and its salts, and other artificial and naturally occurring agents providing sweetness either singly or in combination.

Sweeteners illustratively include glucose, fructose, sucrose, maltose, xylitol, tagatose, sucralose, maltitol, isomaltulose, hydrogenated isomaltulose (e.g., sold under the trademark Isomalt™), lactitol, sorbitol, erythritol, trehalose, maltodextrin, polydextrose, and the like. Other sweeteners illustratively include glycerin, inulin, maltol, acesulfame and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweeteners can be used in the form of crude or refined products such as hydrogenated starch hydrolysates, maltitol syrup, high fructose corn syrup, etc., and as branded products, e.g., a combination of propylene glycol, ethyl alcohol, and proprietary artificial flavor sold under the trademark Sweet Am™ liquid by Flavors of North America, a combination of maltodextrin, sorbitol, and fructose sold under the trademark Sweet Am™ powder with Product Code 918.005, a combination of water, propylene glycol, sorbitol, fructose, and proprietary natural and artificial flavor sold under the trademark Sweet Am™ powder with Product Code 918.010 by Flavors of North America, a combination of 1-10% proprietary plant/vegetable extract and 90-99% dextrose sold under the trademark ProSweet™ by Virginia Dare, a maltitol solution sold under the trademark Maltisweet™ by Ingredion, a sorbitol and sorbitol/xylitol solution sold under the trademark Sorbo™ by SPI Polyols, a high fructose corn syrup sold under the trademark Invertose™ by Ingredion, a combination of sucralose and maltodextrin sold under the trademark Rebalance M60 and X60 by Tate and Lyle, and a sugar containing and sugar-free flavored syrups sold under the trademarks Ora-Sweet® and Ora-Sweet-SF®, respectively, by Paddock Laboratories, Inc. Sweeteners can be used singly or in combinations of two or more. Suitable concentrations of different sweetening agents can be selected based on published information, manufacturers' data sheets and by routine testing. In some embodiments, the sweetener is glucose, fructose, sucrose, xylitol, tagatose, sucralose, maltitol, isomaltulose, hydrogenated isomaltulose, lactitol, sorbitol, erythritol, trehalose, maltodextrin, or polydextrose. In some embodiments, the sweetener is glucose. In some embodiments, the sweetener is sucrose. In some embodiments, the sweetener is sucralose.

In some embodiments, a sweetener is present in the liquid pharmaceutical composition in an amount of about 0.01% w/v to about 15% w/v. In some embodiments, the sweetener is present in the liquid pharmaceutical composition in an amount of about 0.01% w/v to about 0.05% w/v, about 0.05% w/v to about 0.1% w/v, about 0.1% w/v to about 0.5% w/v, about 0.5% w/v to about 0.7% w/v, about 0.7% w/v to about 1% w/v, about 1% w/v to about 2% w/v, about 2% w/v to about 5% w/v, about 5% w/v to about 10% w/v, or about 10% w/v to about 15% w/v. In some embodiments, the sweetener is present in the liquid pharmaceutical composition in an amount of about 0.1% w/v to about 5% w/v. In some embodiments, the sweetener is present in the liquid pharmaceutical composition in an amount of about 0.5% w/v to about 2% w/v. In some embodiments, the sweetener is present in the liquid pharmaceutical composition in an amount of about 1% w/v. In some embodiments, the sweetener is sucralose.

In some embodiments, a sweetener is present in the liquid pharmaceutical composition in an amount of about 0.01% wt to about 15% wt. In some embodiments, the sweetener is present in the liquid pharmaceutical composition in an amount of about 0.01% wt to about 0.05% wt, about 0.05% wt to about 0.1% wt, about 0.1% wt to about 0.5% wt, about 0.5% wt to about 0.7% wt, about 0.7% wt to about 1% wt, about 1% wt to about 2% wt, about 2% wt to about 5% wt, about 5% wt to about 10% wt, or about 10% wt to about 15% wt. In some embodiments, the sweetener is present in the liquid pharmaceutical composition in an amount of about 0.1% wt to about 5% wt. In some embodiments, the sweetener is present in the liquid pharmaceutical composition in an amount of about 0.5% wt to about 2% wt. In some embodiments, the sweetener is present in the liquid pharmaceutical composition in an amount of about 0.84% wt. In some embodiments, the sweetener is sucralose.

In some embodiments, sucralose is present in the liquid pharmaceutical composition in an amount of about 0.01% w/v to about 15% w/v. In some embodiments, sucralose is present in the liquid pharmaceutical composition in an amount of about 0.01% w/v to about 0.05% w/v, about 0.05% w/v to about 0.1% w/v, about 0.1% w/v to about 0.5% w/v, about 0.5% w/v to about 0.7% w/v, about 0.7% w/v to about 1% w/v, about 1% w/v to about 2% w/v, about 2% w/v to about 5% w/v, about 5% w/v to about 10% w/v, or about 10% w/v to about 15% w/v. In some embodiments, sucralose is present in the liquid pharmaceutical composition in an amount of about 0.1% w/v to about 5% w/v. In some embodiments, sucralose is present in the liquid pharmaceutical composition in an amount of about 0.5% w/v to about 2% w/v. In some embodiments, sucralose is present in the liquid pharmaceutical composition in an amount of about 1% w/v.

Additional Excipients

In further embodiments, a hydrocortisone liquid formulation described herein comprises additional excipients including, but not limited to coloring agents and thickeners. Additional excipients such as bulking agents and tonicity agents are within the scope of the embodiments.

In further embodiments, the hydrocortisone liquid formulation comprises a coloring agent for identity and/or aesthetic purposes. Suitable coloring agents illustratively include FD&C Red No. 3, FD&C Red No. 20, FD&C Red No. 40, FD&C Yellow No. 6, FD&C Blue No. 2, D&C Green No. 5, D&C Orange No. 5, caramel, ferric oxide and mixtures thereof.

Thickeners impart viscosity or weight to the resultant liquid forms from hydrocortisone formulations described herein. Exemplary thickeners include dextrin, cellulose derivatives (carboxymethylcellulose and its salts, ethylcellulose, hydroxyethyl cellulose, methylcellulose, hypromellose, and the like) starches, pectin, polyethylene glycol, polyethylene oxide, trehalose and certain gums (xanthan gum, locust bean gum, etc.). In certain embodiments, the hydrocortisone liquid formulation comprises a thickener.

Additional excipients are contemplated in the hydrocortisone liquid formulation embodiments.

These additional excipients are selected based on function and compatibility with the hydrocortisone liquid formulations described herein and may be found, for example in *Remington: The Science and Practice of Pharmacy*, Nineteenth Ed (Easton, PA: Mack Publishing Company, 1995); Hoover, John E., *Remington's Pharmaceutical Sciences*, (Easton, PA: Mack Publishing Co 1975); Liberman, H. A. and Lachman, L., Eds., *Pharmaceutical Dosage Forms* (New York, NY: Marcel Decker 1980); and *Pharmaceutical Dosage Forms and Drug Delivery Systems*, Seventh Ed (Lippincott Williams & Wilkins 1999), herein incorporated by reference in their entirety.

Methods of Treatment

Provided herein, in one aspect, are methods of treating a disease or condition comprising administration of hydrocortisone liquid pharmaceutical compositions described herein to a subject in need thereof. In some embodiments, the liquid pharmaceutical composition is administered to the subject orally. In some embodiments, the hydrocortisone liquid pharmaceutical composition is administered to the subject through a nasogastric tube. In some embodiments, the liquid pharmaceutical composition is administered to the subject through jejunostomy tube. In some embodiments, the liquid pharmaceutical composition is administered to the subject through gastrostomy tube. In some embodiments, the disease or condition is inflammation. In some embodiments, the disease or condition is adrenogenital syndrome, hypercalcemia, or chronic obstructive pulmonary disease. In some embodiments, the disease or condition is selected from endocrine disorders, rheumatic disorders, collagen diseases, dermatologic diseases, allergic states, ophthalmic diseases, respiratory diseases, hematologic disorders, neoplastic diseases, edematous states, gastrointestinal diseases, tuberculous meningitis with subarachnoid block or impending block when used concurrently with appropriate anti-tuberculous chemotherapy, and trichinosis with neurologic or myocardial involvement.

In one instance, hydrocortisone liquid pharmaceutical compositions described herein treat endocrine disorders in a subject in need thereof. In some embodiments, the endocrine disorders comprise primary or secondary adrenocortical insufficiency, congenital adrenal hyperplasia, non-suppurative thyroiditis, or hypercalcemia associated with cancer. In some embodiments, liquid pharmaceutical compositions described herein treat adrenocortical deficiency in a subject in need thereof. In some embodiments, liquid pharmaceutical compositions described herein treat adrenal insufficiency. In some embodiments, a liquid pharmaceutical composition described herein treat pediatric adrenal insufficiency. Adrenocortical deficiency as used herein includes both primary adrenocortical deficiency and secondary adrenocortical deficiency. In one instance, the hydrocortisone oral liquid formulations described herein treat primary adrenocortical deficiency in a subject in need thereof. In other instances, the hydrocortisone oral liquid formulations described herein treat secondary adrenocortical deficiency in a subject in need thereof. In some instances, the subjects are not older than 17 years in age.

In one embodiment, hydrocortisone liquid pharmaceutical compositions described herein treat rheumatic disorders in a subject in need thereof. In some embodiments, the hydrocortisone liquid pharmaceutical composition is used to treat rheumatic disorders as an adjunctive therapy for short-term administration to tide a subject in need thereof over exacerbation. In some embodiments, the hydrocortisone liquid pharmaceutical composition is used to treat acute exacerbation in multiple sclerosis. In some embodiments, the hydrocortisone liquid pharmaceutical composition is used to treat rheumatic disorders as an adjunctive therapy for short-term administration to tide a subject in need thereof over an acute episode. In some embodiments, the rheumatic disorders comprise psoriatic arthritis, rheumatoid arthritis, including juvenile rheumatoid arthritis, ankylosing spondylitis, acute and subacute bursitis, acute nonspecific tenosynovitis, acute gouty arthritis, post-traumatic osteoarthritis, synovitis of osteoarthritis, or epicondylitis.

In other embodiments, hydrocortisone liquid pharmaceutical compositions described herein treat collagen diseases. In some embodiments, the hydrocortisone liquid pharmaceutical composition is used to treat collagen diseases during an exacerbation. In some embodiments, the hydrocortisone liquid pharmaceutical composition is used to treat collagen diseases as a maintenance therapy. In some embodiments, the collagen diseases comprise systemic lupus erythematosus, systemic dermatomyositis (polymyositis), or acute rheumatic carditis.

In yet other embodiments, hydrocortisone liquid pharmaceutical compositions described herein are dermatologic diseases. In some embodiments, the dermatologic diseases comprise pemphigus, bullous dermatitis herpetiformis, severe erythema multiforme (Stevens-Johnson syndrome), exfoliative dermatitis, mycosis fungoides, severe psoriasis, or severe seborrheic dermatitis.

In further embodiments, hydrocortisone liquid pharmaceutical compositions described herein treat allergic states.

In some embodiments, the hydrocortisone liquid pharmaceutical composition is used to treat allergic states for control of severe or incapacitating allergic conditions intractable to adequate trials of conventional treatment. In some embodiments, the dermatologic diseases comprise seasonal or perennial allergic rhinitis, serum sickness, bronchial asthma, contact dermatitis, atopic dermatitis, or drug hypersensitivity reactions.

In some embodiments, hydrocortisone liquid pharmaceutical compositions described herein treat ophthalmic diseases. In some embodiments, ophthalmic diseases comprise allergic conjunctivitis, keratitis, allergic corneal marginal ulcers, herpes zoster ophthalmicus, iritis and iridocyclitis, chorioretinitis, anterior segment inflammation, diffuse posterior uveitis and choroiditis, optic neuritis, or sympathetic ophthalmia.

In further embodiments, hydrocortisone liquid pharmaceutical compositions described herein treat respiratory diseases. In some embodiments, respiratory diseases comprise symptomatic sarcoidosis, Loeffler's syndrome, berylliosis, fulminating or disseminated pulmonary tuberculosis when used concurrently with appropriate anti-tuberculous chemotherapy, or aspiration pneumonitis.

In some embodiments, hydrocortisone liquid pharmaceutical compositions described herein treat hematologic disorders. In some embodiments, hematologic disorders comprise idiopathic thrombocytopenic purpura in adults, secondary thrombocytopenia in adults, acquired (autoimmune) hemolytic anemia, erythroblastopenia (RBC anemia), or congenital (erythroid) hypoplastic anemia.

In further embodiments, hydrocortisone liquid pharmaceutical compositions described herein treat neoplastic diseases. In some embodiments, the hydrocortisone liquid pharmaceutical compositions are used to treat neoplastic diseases for palliative management. In some embodiments, neoplastic diseases comprise leukemias and lymphomas in adults, or acute leukemia of childhood.

In some embodiments, hydrocortisone liquid pharmaceutical compositions described herein treat neoplastic diseases. In some embodiments, the hydrocortisone liquid pharmaceutical compositions are used to treat neoplastic diseases for palliative management. In some embodiments, neoplastic diseases comprise leukemias and lymphomas in adults, or acute leukemia of childhood.

In further embodiments, hydrocortisone liquid pharmaceutical compositions described herein treat edematous states. In some embodiments, the hydrocortisone liquid pharmaceutical compositions are used to induce a diuresis or remission of proteinuria in the nephrotic syndrome, without uremia, of the idiopathic type or that due to lupus erythematosus. In some embodiments, edematous states comprise proteinuria in nephrotic syndrome.

In some embodiments, hydrocortisone liquid pharmaceutical compositions described herein treat gastrointestinal diseases. In some embodiments, the hydrocortisone liquid pharmaceutical compositions are used to tide a subject in need thereof over a critical period of the gastrointestinal diseases. In some embodiments, gastrointestinal diseases comprise ulcerative colitis or regional enteritis.

Administration of hydrocortisone liquid pharmaceutical compositions described herein is at a dosage described herein or at other dose levels and formulations determined and contemplated by a medical practitioner. In certain embodiments, the hydrocortisone oral liquid formulations described herein are administered as an adjunctive therapy for short-term administration to tide the subject over an acute episode or exacerbation. In certain embodiments, the hydrocortisone oral liquid formulations described herein are administered as low-dose maintenance therapy. In some embodiments, the hydrocortisone oral liquid formulations described herein are used to induce a diuresis or remission of proteinuria in the nephrotic syndrome, without uremia, of the idiopathic type or that due to lupus erythematosus. In certain embodiments, the hydrocortisone oral liquid formulations described herein are used for control of severe or incapacitating allergic conditions intractable to adequate trials of conventional treatment. In certain embodiments, the hydrocortisone oral liquid formulations described herein are used for Severe acute and chronic allergic and inflammatory processes involving the eye and its adnexa. In certain embodiments, the hydrocortisone oral liquid formulations described herein are used to tide the subject over a critical period of gastrointestinal diseases. In certain embodiments, the hydrocortisone oral liquid formulations described herein are used for palliative management. In certain embodiments, the hydrocortisone oral liquid formulations described herein are administered for prophylactic and/or therapeutic treatments.

In certain therapeutic applications, the hydrocortisone oral liquid formulations are administered to a patient already suffering from a disease, e.g., inflammation or adrenocortical deficiency, in an amount sufficient to cure the disease or at least partially arrest or ameliorate the symptoms, e.g., increase blood pressure, blood sugar, or appetite. Amounts effective for this use depend on the severity of the disease, previous therapy, the patient's health status, weight, and response to the hydrocortisone oral liquid formulations, and the judgment of the treating physician. In some embodiments, the liquid pharmaceutical compositions are administered in a therapeutically effective amount. Therapeutically effective amounts for each use described herein can optionally be determined by methods including, but not limited to, a dose escalation clinical trial. The precise therapeutically effective amounts for each use described herein can also depend on the patient's state of health, weight, and the like. When used in a patient, the therapeutically effective amounts for each use described herein can depend on the risk or susceptibility of developing the particular disease, previous therapy, the patient's health status and response to the hydrocortisone formulations, and the judgment of the treating physician.

In certain embodiments wherein the patient's condition does not improve, upon the doctor's discretion the administration of a hydrocortisone oral liquid composition described herein are administered chronically, that is, for an extended period of time, including throughout the duration of the patient's life in order to ameliorate or otherwise control or limit the symptoms of the patient's disease. In other embodiments, administration of a hydrocortisone liquid pharmaceutical composition continues until complete or partial response of a disease.

In certain embodiments wherein a patient's status does improve, the dose of a hydrocortisone liquid pharmaceutical composition being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In some embodiments, hydrocortisone oral liquid compositions described herein are administered chronically. For example, in some embodiments, a hydrocortisone liquid pharmaceutical composition is administered as a continuous dose, i.e., administered daily to a subject. In some other embodiments, hydrocortisone oral liquid compositions described herein are administered intermittently (e.g. drug holiday that includes a period of time in which the formulation is not administered or is administered in a reduced amount).

In some embodiments a hydrocortisone liquid pharmaceutical composition is administered to a subject who is in a fasted state. A fasted state refers to a subject who has gone without food or fasted for a certain period of time. General fasting periods include at least 4 hours, at least 6 hours, at least 8 hours, at least 10 hours, at least 12 hours, at least 14 hours and at least 16 hours without food. In some embodiments, a hydrocortisone liquid pharmaceutical composition is administered orally to a subject who is in a fasted state for at least 8 hours. In other embodiments, a hydrocortisone liquid pharmaceutical composition is administered to a subject who is in a fasted state for at least 10 hours. In yet other embodiments, a hydrocortisone liquid pharmaceutical composition is administered to a subject who is in a fasted state for at least 12 hours. In other embodiments, a hydrocortisone liquid pharmaceutical composition is administered to a subject who has fasted overnight.

In other embodiments a hydrocortisone liquid pharmaceutical composition is administered to a subject who is in a fed state. A fed state refers to a subject who has taken food or has had a meal. In certain embodiments, a hydrocortisone liquid pharmaceutical composition is administered to a subject in a fed state 5 minutes post-meal, 10 minutes post-meal, 15 minutes post-meal, 20 minutes post-meal, 30 minutes post-meal, 40 minutes post-meal, 50 minutes post-meal, 1-hour post-meal, or 2 hours post-meal. In certain instances, a hydrocortisone liquid pharmaceutical composition is administered to a subject in a fed state 30 minutes post-meal. In other instances, a hydrocortisone liquid pharmaceutical composition is administered to a subject in a fed state 1-hour post-meal. In yet further embodiments, a hydrocortisone liquid pharmaceutical composition is administered to a subject with food.

In further embodiments described herein, a hydrocortisone liquid pharmaceutical composition is administered at a certain time of day for the entire administration period. For example, a hydrocortisone liquid pharmaceutical composition can be administered at a certain time in the morning, in the evening, or prior to bed. In certain instances, a hydrocortisone liquid pharmaceutical composition is administered in the morning. In other embodiments, a hydrocortisone liquid pharmaceutical composition can be administered at different times of the day for the entire administration period. For example, a hydrocortisone liquid pharmaceutical composition can be administered on 8:00 am in the morning for the first day, 12 pm noon for the next day or administration, 4 pm in the afternoon for the third day or administration, and so on.

Dosing

In one aspect, hydrocortisone oral liquid compositions described herein are used for the treatment of diseases and conditions described herein. In addition, a method for treating any of the diseases or conditions described herein in a subject in need of such treatment, involves administration of hydrocortisone oral liquid compositions in therapeutically effective amounts to said subject.

Dosages of hydrocortisone oral liquid compositions described can be determined by any suitable method. Maximum tolerated doses (MTD) and maximum response doses (MRD) for hydrocortisone can be determined via established animal and human experimental protocols as well as in the examples described herein. For example, toxicity and therapeutic efficacy of hydrocortisone can be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Hydrocortisone dosages exhibiting high therapeutic indices are of interest. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized. Additional relative dosages, represented as a percent of maximal response or of maximum tolerated dose, are readily obtained via the protocols.

In some embodiments, the amount of a given hydrocortisone liquid pharmaceutical composition that corresponds to such an amount varies depending upon factors such as the particular hydrocortisone salt or form, disease condition and its severity, the identity (e.g., weight, sex) of the subject or host in need of treatment, but can nevertheless be determined according to the particular circumstances surrounding the case, including, e.g., the specific agent being administered, the liquid composition type, the condition being treated, and the subject or host being treated. In some instances, the hydrocortisone oral liquid compositions can be discontinued if there is a lack of satisfactory response is noted.

In some embodiments, hydrocortisone oral liquid compositions described herein are provided in a dose per day from about 1 to about 50 mg/m$^2$/day. In some embodiments, the hydrocortisone oral liquid compositions are provided in a dose per day from about 1 to about 3 mg/m$^2$/day, from about 3 to about 5 mg/m$^2$/day, about 5 to about 8 mg/m$^2$/day, about 8 to about 10 mg/m$^2$/day, about 10 to about 15 mg/m$^2$/day, about 15 to about 20 mg/m$^2$/day, about 20 to about 30 mg/m$^2$/day, about 30 to about 40 mg/m$^2$/day, or about 40 to about 50 mg/m$^2$/day. In some embodiments, the hydrocortisone oral liquid compositions are provided in a dose per day from about 1 to about 3 mg/m$^2$/day. In some embodiments, the hydrocortisone oral liquid compositions are provided in a dose per day from about 3 to about 5 mg/m$^2$/day. In some embodiments, the hydrocortisone oral liquid compositions are provided in a dose per day from about 5 to about 8 mg/m$^2$/day. In some embodiments, the hydrocortisone oral liquid compositions are provided in a dose per day from about 8 to about 10 mg/m$^2$/day. In some embodiments, the hydrocortisone oral liquid compositions are provided in a dose per day from about 10 to about 15 mg/m$^2$/day. In some embodiments, the hydrocortisone oral liquid compositions are provided in a dose per day from about 15 to about 20 mg/m$^2$/day. In some embodiments, the hydrocortisone oral liquid compositions are provided in a dose per day from about 20 to about 30 mg/m$^2$/day. In some embodiments, the hydrocortisone oral liquid compositions are provided in a dose per day from about 30 to about 40 mg/m²/day. In some embodiments, the hydrocortisone oral liquid compositions are provided in a dose per day from about 40 to about 50 mg/m²/day. In some embodiments, the hydrocortisone oral liquid compositions are provided in a dose per day from about 8 to about 10 mg/m²/day.

In some embodiments, hydrocortisone oral liquid compositions described herein are provided in a dose per day from about 0.01 mg to 1000 mg, from about 0.1 mg to about 500 mg, from about 10 mg to about 300 mg, from about 20 mg to about 240 mg of hydrocortisone. In certain embodiments, the hydrocortisone oral liquid compositions described herein are provided in a daily dose of about 0.01 mg to about 0.05 mg, about 0.05 mg to about 0.5 mg, about 0.5 mg to about 1 mg, about 1 mg to about 5 mg, about 5 mg to about 10 mg, about 10 mg to about 20 mg, about 20 mg to about 50 mg, about 50 mg to about 80 mg, about 80 mg to about 120 mg, about 120 mg to about 150 mg, about 150 mg to about 180 mg, about 180 mg to about 210 mg, about 210 mg to about 240 mg, about 240 mg to about 300 mg, about 300 mg to about 400 mg, about 400 mg to about 500 mg, about 500 mg to about 800 mg, about 800 mg to about 1000 mg. In certain instances, the hydrocortisone oral liquid compositions described herein are provided in a dose per day of about 10 mg. In certain instances, the hydrocortisone oral liquid compositions described herein are provided in a dose per day of about 20 mg. In certain instances, the hydrocortisone oral liquid compositions described herein are provided in a dose per day of about 25 mg. In certain instances, the hydrocortisone oral liquid compositions described herein are provided in a dose per day of about 30 mg. In certain instances, the hydrocortisone oral liquid compositions described herein are provided in a dose per day of about 35 mg. In certain instances, the hydrocortisone oral liquid compositions described herein are provided in a dose per day of about 40 mg. In certain instances, the hydrocortisone oral liquid compositions described herein are provided in a dose per day of about 50 mg. In certain instances, the hydrocortisone oral liquid compositions described herein are provided in a dose per day of about 80 mg. In certain instances, the hydrocortisone oral liquid compositions described herein are provided in a dose per day of about 100 mg. In certain instances, the hydrocortisone oral liquid compositions described herein are provided in a dose per day of about 150 mg. In certain instances, the hydrocortisone oral liquid compositions described herein are provided in a dose per day of about 200 mg. In certain instances, the hydrocortisone oral liquid compositions described herein are provided in a dose per day of about 240 mg. The dose per day described herein can be given once per day or multiple times per day in the form of sub-doses given b.i.d., t.i.d., q.i.d., or the like where the number of sub-doses equal the dose per day.

In further embodiments, the daily dosages appropriate for the hydrocortisone oral liquid compositions described herein are from about 0.01 to about 1.0 mg/kg per body weight. In one embodiment, the daily dosages appropriate for the hydrocortisone oral liquid compositions are from about 0.02 to about 0.8 mg/kg hydrocortisone per body weight. In another embodiment, the daily dosage appropriate for the hydrocortisone oral liquid compositions are from about 0.05 to about 0.6 mg/kg per body weight. In another embodiment, the daily dosage appropriate for the hydrocortisone oral liquid compositions is about 0.05 mg/kg, about 0.06 mg/kg, about 0.07 mg/kg, about 0.08 mg/kg, about 0.10 mg/kg, about 0.15 mg/kg, about 0.20 mg/kg, about 0.25 mg/kg, about 0.30 mg/kg, about 0.40 mg/kg, about 0.50 mg/kg, or about 0.60 mg/kg.

In other embodiments the hydrocortisone oral liquid compositions are provided at the maximum tolerated dose (MTD) for hydrocortisone or a pharmaceutically acceptable salt thereof. In other embodiments, the amount of the hydrocortisone oral liquid compositions administered is from about 10% to about 90% of the maximum tolerated dose (MTD), from about 25% to about 75% of the MTD, or about 50% of the MTD. In particular embodiments, the amount of the hydrocortisone oral liquid compositions administered is from about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to about 99% or higher, of the MTD for hydrocortisone or a pharmaceutically acceptable salt thereof.

In further embodiments, the hydrocortisone oral liquid compositions are provided in a dosage that is similar, comparable or equivalent to a dosage of a known hydrocortisone tablet formulation (Cortef®). In other embodiments, the hydrocortisone oral liquid compositions are provided in a dosage that provides similar, comparable or equivalent pharmacokinetic parameters (e.g., AUC, $C_{max}$, $T_{max}$, $C_{min}$, $T_{1/2}$) as a dosage of a known hydrocortisone tablet formulation. Similar, comparable or equivalent pharmacokinetic parameters, in some instances, refer to within about 80% to about 125%, about 80% to about 120%, about 85% to about 125%, about 90% to about 110%, or increments therein, of the given values. It should be recognized that the ranges can, but need not be symmetrical, e.g., 85% to 105%.

Further Combinations

The treatment of certain diseases or conditions (e.g., adrenocortical insufficiency, other endocrine disorders, rheumatic disorders and the like) in a subject with a hydrocortisone liquid pharmaceutical composition described herein encompass additional therapies and treatment regimens with other agents in some embodiments. Such additional therapies and treatment regimens can include another therapy, e.g., additional corticosteroids, such as mineralocorticoids or fludrocortisone, for treatment of the particular disease or condition in some embodiments. In one instance, hydrocortisone liquid pharmaceutical composition can be used in conjunction in conjunction with mineralocorticoids to treat primary or secondary adrenocortical insufficiency where applicable, for example, in infancy mineralocorticoid supplementation is particularly important. Alternatively, in other embodiments, additional therapies and treatment regimens include other agents used to treat adjunct conditions associated with the disease or condition or a side effect from the hydrocortisone liquid pharmaceutical composition in the therapy.

Additional agents for use in combination with a hydrocortisone liquid pharmaceutical composition described herein include, but are not limited to, corticosteroids (e.g., fludrocortisone), chemotherapy (e.g., appropriate antituberculous chemotherapy, mitoxantrone), analgesic (e.g., acetaminophen), vitamin A or a derivative thereof, anti-inflammatory agents (e.g., NSAIDs, tumor necrosis factor-alpha inhibitors), bronchodilators (e.g., beta-2 agonists), colchicine, immunosuppressant (e.g., cyclosporine, azathioprine), antibiotics (e.g., cefazolin), antiviral drug (e.g., acyclovir), immunotherapy (e.g., anti-CD20 monoclonal antibody such as rituximab, chimeric antigen receptor (CAR) T-cell therapy).

Preparation of Hydrocortisone Liquid Formulations

Preparation of the hydrocortisone liquid pharmaceutical composition described herein includes any known pharmaceutical method. In one embodiment, the hydrocortisone liquid pharmaceutical composition described herein is prepared by mixing hydrocortisone or a pharmaceutically acceptable salt thereof with a nonaqueous liquid carrier, thereby forming a solution of hydrocortisone in the nonaqueous liquid carrier. In some cases, the method comprises adding a preservative, optionally a sweeter, and optionally a flavoring agent into the solution of hydrocortisone. In some cases, the preservative, optionally the sweeter, and optionally the flavoring agent is added to the nonaqueous liquid carrier before mixing hydrocortisone or a pharmaceutically acceptable salt thereof with the nonaqueous liquid carrier. In some instances, the method comprises optionally filtering the solution of hydrocortisone over a filter into a container. In some embodiments, the filter is a 5 m disposable filter.

In some embodiments, the hydrocortisone liquid pharmaceutical composition described herein is prepared by dissolving a preservative, a sweetener, a flavoring agent, and hydrocortisone or a pharmaceutically acceptable salt thereof in a nonaqueous liquid carrier (e.g., in a compounding container). In some embodiments, the hydrocortisone or a pharmaceutically acceptable salt thereof, the nonaqueous liquid carrier, and the excipients such as a preservative, a sweetener and a flavoring agent can be combined in any order of addition. In some embodiments, hydrocortisone or a pharmaceutically acceptable salt thereof is added after preservatives, sweeteners, flavoring agents are dissolved in PEG 400 in a compounding container. In some embodiments, propylene glycol is added to the compounding container after hydrocortisone or a pharmaceutically acceptable salt thereof is dissolved. In some embodiments, hydrocortisone or a pharmaceutically acceptable salt thereof is added after antimicrobial agent and sweetener are dissolved in PEG 400 in a compounding container. In some embodiments, ethyl maltol and antioxidant are dissolved in propylene glycol in a side container. In some embodiments, the propylene glycol with ethyl maltol and antioxidant dissolved is then added to the compounding container. In some embodiments, PEG 400 and propylene glycol are mixed in the compounding container before any excipients are dissolved. In some embodiments, hydrocortisone or a pharmaceutically acceptable salt thereof is added after preservative, ethyl maltol, and sweetener are dissolved in a compounding container. In some embodiments, berry flavor is dissolved at the same time when hydrocortisone or a pharmaceutically acceptable salt thereof is dissolved. In some embodiments, a sufficient amount of glycerin is added after hydrocortisone or a pharmaceutically acceptable salt thereof to the compounding container. In some embodiments, the liquid pharmaceutical composition in the compounding container is optionally filtered through a filter unit. In some embodiment, the filter unit comprises a 5 m disposable filter. In some embodiment, the liquid pharmaceutical composition in the compounding container is stored in a storage tank after filtration.

Kits and Articles of Manufacture

For the hydrocortisone liquid compositions described herein, kits and articles of manufacture are also described. Such kits can comprise a carrier, package, or container that is compartmentalized to receive one or more containers such as bottles, vials, tubes, and the like, each of the container(s) comprising one of the separate elements to be used in a method described herein including a hydrocortisone liquid composition. Suitable containers include, for example, tanks, bottles, vials, dosing cups, syringes, and test tubes. The containers can be formed from a variety of materials such as glass or plastic. The containers can further comprise a light protection mechanism, for example, an amber glass bottle. The containers can have different sizes, such as about 12 oz, about 10 oz, about 8 oz, or about 4 oz. The containers can have seal, such as induction seal. In some embodiments, the kit comprises a package enclosing the liquid pharmaceutical composition described herein. In some embodiments, the package is a bottle. In some embodiments, the package has a light protection mechanism.

A kit can comprise one or more additional containers, each with one or more of various materials (such as reagents, optionally in concentrated form, and/or devices) desirable from a commercial and user standpoint for a hydrocortisone liquid composition described herein. Non-limiting examples of such materials include, but not limited to, buffers, diluents, filters, needles, syringes, carrier, package, container, vial and/or tube labels listing contents and/or instructions for use, and package inserts with instructions for use associated with a hydrocortisone liquid formulation described herein. In some embodiments, the kit comprises a syringe or a dosing cup. A set of instructions can also be included. In some embodiments, the kit comprises instructions for use of the liquid pharmaceutical compositions described herein.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

Certain Definitions

Unless defined otherwise, all technical and scientific terms used herein have the same meanings as commonly understood by one of ordinary skill in the art. Although any methods and materials similar or equivalent to those described herein can be used in the practice or testing of embodiments described herein, certain preferred methods, devices, and materials are now described.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The use of the term "or" in the claims is used to mean "and/or" unless explicitly indicated to refer to alternatives only or the alternatives are mutually exclusive, although the disclosure supports a definition that refers to only alternatives and to "and/or." The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent such as hydrocortisone is directed to the treatment and/or the amelioration of, reversal of, or stabilization of the symptoms of adrenocortical insufficiency described herein.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with a hydrocortisone formulation, can include, but is not limited to providing a hydrocortisone formulation systemically to a patient by, e.g., oral administration whereby the therapeutic reaches the target tissue or cells. "Administering" a formulation may be accomplished by oral administration, injection, topical administration, or by other methods alone or in combination with other known techniques.

The term "animal" as used herein includes, but is not limited to, humans and non-human vertebrates such as wild, domestic and farm animals. As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is child. In further instances, the human is 12 years of age or younger. In certain instances, the human is elderly. In other instances, the human is 60 years of age or older. Other examples of subjects include experimental animals such as mice, rats, dogs, cats, goats, sheep, pigs, and cows. The experimental animal can be an animal model for a disorder, e.g., a transgenic mouse with adrenocortical insufficiency pathology. A patient can be a human suffering from adrenocortical insufficiency, or its variants or etiological forms.

By "pharmaceutically acceptable", it is meant the carrier, diluent or excipient must be compatible with the other ingredients of the formulation and not deleterious to the recipient thereof.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

"Effective amount," and "sufficient amount" may be used interchangeably, and refer to an amount of a substance that is sufficient to achieve an intended purpose or objective.

A "therapeutically effective amount" when used in connection with a pharmaceutical composition described herein is an amount of one or more pharmaceutically active agent(s) sufficient to produce a therapeutic result in a subject in need thereof.

"Therapeutically equivalent" when used in connection with a pharmaceutical composition de-scribed herein refers to an amount or quantity of a pharmaceutically acceptable salt or ester of a pharmaceutically active agent that is equivalent to the therapeutically effective amount of the free base or alcohol of the pharmaceutically active agent.

The terms "treat," "treated," "treatment," or "treating" as used herein refers to therapeutic treatment, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

EXAMPLES

The following examples are provided to further illustrate some embodiments of the present disclosure, but are not intended to limit the scope of the disclosure; it will be understood by their exemplary nature that other procedures, methodologies, or techniques known to those skilled in the art may alternatively be used.

Example A: Solubility Studies of Hydrocortisone in Different Solvents or Combination Solvent Systems Hydrocortisone powder was added into different solution or solvent systems to evaluate a suitable solvent or carrier for making a 1 mg/mL hydrocortisone liquid oral formulation. The single solvents and combination solvent systems tested, and their results are summarized in Table A-1 and Table A-2, respectively. Visual observations were made while carrying out the above experiments. It was found that hydrocortisone does not dissolve in glycerin. For combination solvent systems, hydrocortisone was dissolved in the other solvents and glycerin used as a vehicle. Hydrocortisone has good solubility (for 1 mg/mL strength) in PEG 400, propylene glycol, labrasol and ethanol.

TABLE A-1

Solubility of hydrocortisone in one solvent.

| Solvent | Solubility (mg/mL) |
|---|---|
| Propylene Glycol | >12 |
| Glycerin | <1 |
| PEG 400 | >9 |
| Ethanol | >12 |
| Labrasol | 8-9 |

TABLE A-1

Solubility of hydrocortisone in a combination solvent systems.

| Solvent system | Ratio (% w/w) | Solubility more than 1 mg/mL? |
|---|---|---|
| Ethanol/Glycerin | 2/98 | No |
|  | 5/95 | Yes |
| PG/Glycerin | 5/95 | No |
|  | 10/90 | Yes |
| PG/PEG | 5/95 | Yes |
|  | 10/90 | Yes |
| PEG/Glycerin | 30/70 | Yes |
|  | 50/50 | Yes |
| PG/PEG/Glycerin | 5/25/70 | Yes |
|  | 5/40/55 | Yes |

Example B: Solvent Screening for Compatibility

The compatibility of hydrocortisone and different solvents was evaluated. 10 mg of hydrocortisone was dissolved in 10 grams of each solvent listed in Table B-1. Initial samples and samples heated at 60° C. for 3 days were prepared and submitted to the lab for assay analysis. The sample with ethanol was heated for 6 hours at 60° C. The assay and impurity analysis were conducted according to the HPLC method in Table B-3. The results are summarized in Table B-1 and Table B-2.

TABLE B-1

Solvent screening for hydrocortisone content after heated at 60° C.

| Lot Number | Excipient | Assay Results (mg/mL) |
|---|---|---|
| RB0059-101-1A Initial | 10 mg hydrocortisone + 10 g Propylene Glycol | 0.96 |
| RB0059-101-1A 3 d/ 60° C. | 10 mg hydrocortisone + 10 g Propylene Glycol | 0.92 |
| RB0059-101-2A Initial | 10 mg hydrocortisone + 10 g PEG 400 | 0.96 |
| RB0059-101-2A 3 d/ 60° C. | 10 mg hydrocortisone + 10 g PEG 400 | 0.98 |
| RB0059-101-3A Initial | 10 mg hydrocortisone + 10 g Labrasol | 0.85 |
| RB0059-101-3A 3 d/ 60° C. | 10 mg hydrocortisone + 10 g Labrasol | 1.11 |
| RB0059-101-4A Initial | 10 mg hydrocortisone + 5 g PEG400 + 5 g Glycerin | 1.67 |
| RB0059-101-4A 3 d/ 60° C. | 10 mg hydrocortisone + 5 g PEG 400 + 5 g Glycerin | 1.47 |
| RB0059-101-5A Initial | 10 mg hydrocortisone + 10 g Ethanol | 0.77 |
| RB0059-101-5A 6 hours/60° C. | 10 mg hydrocortisone + 10 g Ethanol | 0.85 |

TABLE B-2

Impurity data for lot # RB0059-101-4A.

| Sample | Formula | Density (g/ml) | Assay (mg/mL) | G Imp | Imp B | RRT 0.819/0.820 | RRT 1.366 | RRT 1.368 | RRT 1.702 | Total Imp (%) |
|---|---|---|---|---|---|---|---|---|---|---|
| RB0059-101-4 Initial | PEG400/GLY-50/50 hydrocortisone | 1.20 | 1.64 | ND | 0.09 | 0.12 | 0.06 | — | — | 0.49 |
| RB0059-101-4 3D 60° C. | 1 mg/mL | 1.20 | 1.47 | 0.52 | 0.67 | — | — | 1.03 | 0.07 | 2.73 |

TABLE B-3

HPLC method for assay and impurity analysis for hydrocortisone.

| | |
|---|---|
| Instrument | Waters ACQUITY UPLC H-Class System with UV detector or equivalent |
| LC Column | Avantor C18-AR, 4.6 × 150 mm, 3.0 μm or equivalent |
| Column Temperature | 30° C. |
| Sample Temperature | Ambient |
| Detector Wavelength | 245 nm |
| Detector | UV |
| Flow Rate | 0.7 mL/min |
| Injection Volume | 10 μL |
| Run Time | 63 minutes |

| Mobile Phase Gradient Program | | | |
|---|---|---|---|
| Time (min) | Mobile Phase A (%) | Mobile Phase B (%) | Curve |
| 0.0 | 79.2 | 20.8 | 6 |
| 11.0 | 74.0 | 26.0 | 6 |
| 18.0 | 69.0 | 31.0 | 6 |
| 43.0 | 59.0 | 41.0 | 6 |
| 44.0 | 59.0 | 41.0 | 6 |
| 48.0 | 10.0 | 90.0 | 6 |
| 53.0 | 10.0 | 90.0 | 6 |
| 53.5 | 79.2 | 20.8 | 6 |
| 63.0 | 79.2 | 20.8 | 6 |

Example C: Prototype Hydrocortisone Oral Liquid Compositions and Stability Data Prototype hydrocortisone oral liquid compositions with and without purified water were prepared according to Table C-1. The formulations were tested for assay content and impurities at initial timepoint and after 2 weeks when stored at about 40° C. and about 75% RH. The testing results are summarized in Table C-2. Impurities observed at a level below 0.05% are not shown in Table C-2 but are tracked in future stability testing.

TABLE C-1

Prototype hydrocortisone oral liquid compositions for lot # RB0067-001B and lot # RB0067-003B3.

| | Quantity, g | |
|---|---|---|
| Ingredient | RB0067-001B | RB0067-003B3 |
| Hydrocortisone | 0.1 | 0.1 |
| PEG 400 | 40 | 35 |
| Glycerin | 60 | 60 |
| Purified Water | NA | 5 |
| Sucralose | 0.1 | 0.1 |
| Berry Flavor | 0.2 | 0.2 |
| Methylparaben | 0.18 | 0.18 |
| Propylparaben | 0.02 | 0.02 |
| Glycerin | Qs 100 mL | Qs 100 mL |

Qs = Quantum satis, or sufficient quantity

TABLE C-2

Stability results for lot # RB0067-001B and lot # RB0067-003B3.

| Sample | Formula | Density (g/ml) | Assay (mg/mL) | Imp G | Imp B | Imp E | RRT 0.819/0.820 | RRT 1.366 | RRT 1.215 | RRT 1.221 | RRT 1.233/1.235 | RRT 1.368 | RRT 1.493/1.497 | RRT 1.702 | Total Imp (%) |
|---|---|---|---|---|---|---|---|---|---|---|---|---|---|---|---|
| RB0067-001B Initial | Prototype formula in 40% PEG | 1.21 | 1.08 | — | — | 0.32 | — | — | 0.06 | — | — | — | — | — | 0.66 |
| RB0067-001B 2W 40/75 | | 1.21 | 1.04 | 1.08 | 0.10 | ND | — | — | — | 0.07 | 0.21 | — | 0.14 | — | 1.81 |
| RB0067-003B3 Initial | Prototype formula in 35% PEG and 5% Water | 1.20 | 1.01 | 0.14 | — | — | — | — | — | — | — | — | — | — | 0.44 |
| RB0067-003B3 2W 40/75 | | 1.20 | 0.98 | 1.70 | 0.15 | — | — | — | — | — | 0.31 | — | 0.06 | — | 2.51 |

Example D: Stability Data for Hydrocortisone Oral Liquid Compositions with and without Water Hydrocortisone oral liquid compositions with and without purified water were prepared according to Table D-1 and Table D-2, respectively.

TABLE D-1

Hydrocortisone oral liquid compositions with water, lot # RB0067-014A and RB0067-016A.

| | Quantity % w/v | |
|---|---|---|
| Ingredient | RB0067-014A | RB0067-016A |
| Hydrocortisone | 0.1 | 0.1 |
| PEG 400 | 50 | 50 |
| BHA | 0.01 | 0.01 |
| BHT | 0.01 | 0.01 |
| Methylparaben | 0.18 | 0.18 |
| Propylparaben | 0.02 | 0.02 |
| Sucralose | 1 | 1 |
| Berry Flavor | 0.2 | 0.2 |
| Purified Water | 5 | 10 |
| Maltose | 1.2 | 1.2 |
| EDTA | — | 0.1 |
| Glycerin | 61.28 | 55.18 |
| Observation | Clear solution | Clear solution |

TABLE D-2

Hydrocortisone oral liquid compositions without water, lot # RB0067-009A, RB0067-010A, RB0067-011A, RB0067-012A, and RB0067-019A.

| | Quantity % w/v | | | | |
|---|---|---|---|---|---|
| Ingredient | RB0067-009A | RB0067-010A | RB0067-011A | RB0067-012A | RB0067-019A |
| Hydrocortisone | 0.1 | 0.1 | 0.1 | 0.1 | 0.1 |
| PEG 400 | 50 | 40 | 50 | 40 | 50 |
| BHA | 0.01 | 0.01 | 0.01 | 0.01 | 0.01 |
| BHT | 0.01 | 0.01 | 0.01 | 0.01 | — |
| Methylparaben | 0.18 | 0.18 | 0.18 | 0.18 | 0.18 |
| Propylparaben | 0.02 | 0.02 | 0.02 | 0.02 | 0.02 |
| Sucralose | 1 | 1 | 1 | 1 | 1 |
| Berry Flavor | 0.2 | 0.2 | 10.2 | 0.2 | 0.2 |
| Propylene glycol | — | — | 5 | 5 | 5 |
| Ethyl maltol | — | — | — | — | 0.1 |
| Glycerin | 68.48 | 79.48 | 62.48 | 73.48 | 61.39 |
| Observation | Clear solution | Clear solution | Clear solution | Clear solution | Clear slight yellowish solution |

The formulations above were tested for assay content and impurities at different timepoints such as initial, after 3 days when heated at about 60° C., after 1 month, 2 months, 3 months, and 6 months when stored at about 25° C. and about 60% RH, and after 2 weeks, 1 month, 2 months, 3 months, and 6 months when stored at about 40° C. and about 75% RH. The testing results are summarized in Table D-3 to Table D-9. Impurities observed at a level below 0.05% are not shown in Table D-3 to Table D-9 but are tracked in future stability testing. Based on the stability data, it was decided that the final formulation would mostly be based on lot #RB0067-019A since its 3-month data under accelerated conditions shows the highest assay content and the lowest total impurities as compared to other batches made in Table D-1 and Table D-2.

TABLE D-3

Stability data for lot # RB0067-009A.

| Sample Name | Formula | Assay Result (mg/mL) | Density (g/mL) | 0.710 | 0.915 (U-01) | Imp h | Imp G | 1.071 (U-13) | 1.064 | Imp B | 1.101 | Keto (U-03) |
|---|---|---|---|---|---|---|---|---|---|---|---|---|
| Initial | RB0067-009A (no water) 50% PEG + BHA + BHT | 1.013 | 1.20 | — | — | — | ND | — | — | — | — | — |
| 3D60C | | 0.983 | 1.20 | — | — | — | 0.32 | — | — | — | — | 0.13 |
| 1m-25/60 | | 1.006 | 1.20 | — | — | — | 0.08 | — | — | — | — | — |
| 2m-25/60 | | 1.010 | 1.20 | — | — | — | 0.12 | — | — | — | — | — |
| 3m-25/60 | | 0.987 | 1.20 | — | — | — | 0.15 | — | — | — | — | 0.05 |
| 6m-25/60 | | 1.003 | 1.20 | — | — | 0.03 | 0.26 | — | — | — | — | 0.05 |
| 2w-40/75 | | 0.987 | 1.20 | 0.07 | — | — | 0.16 | — | — | — | — | — |
| 1m-40/75 | | 0.996 | 1.20 | — | 0.05 | — | 0.37 | — | — | — | — | 0.05 |
| 2m-40/75 | | 1.000 | 1.20 | — | 0.12 | — | — | 1.09 | 0.09 | — | — | 0.14 |
| 3m-40/75 | | 0.942 | 1.20 | — | 0.27 | — | 1.42 | — | 0.20 | 0.10 | — | 0.28 |
| 16m-40/75 | | 0.888 | 1.20 | — | — | 0.07 | 2.23 | — | — | 1.16 | 0.21 | 0.99 |

TABLE D-3-continued

Stability data for lot # RB0067-009A.

| Sample Name | Formula | (U-04) | Enol 1 1.432 (U-08) | 1.474 | (Unk 5 Enol 2 Imp) | 1.592/ 1.598 | 1.649 | 1.674 | 3.139 | 2.620 | Asym dimer | Total Imp (%) |
|---|---|---|---|---|---|---|---|---|---|---|---|---|
| Initial | RB0067-009A (no water) 50% PEG + BHA + BHT | — | — | — | — | — | — | — | — | — | — | ND |
| 3D60C | | 0.29 | — | — | 0.19 | — | — | — | — | — | — | 0.91 |
| 1m-25/60 | | — | — | — | — | — | — | — | — | — | — | 0.08 |
| 2m-25/60 | | — | — | — | — | — | — | — | — | — | — | 0.12 |
| 3m-25/60 | | — | — | — | 0.06 | — | — | — | — | — | — | 0.32 |
| 6m-25/60 | | — | — | — | 0.09 | 0.07 | — | — | — | — | 0.06 | 0.67 |
| 2w-40/75 | | — | — | — | 0.08 | — | — | 0.05 | — | — | — | 0.36 |
| 1m-40/75 | | — | 0.08 | — | 0.10 | — | — | — | — | — | — | 0.65 |
| 2m-40/75 | | 0.02 | — | — | 0.10 | — | — | — | — | — | — | 1.56 |
| 3m-40/75 | | — | — | 0.05 | 0.10 | 0.66 | 0.05 | — | — | 0.07 | — | 3.20 |
| 16m-40/75 | | — | — | — | — | 2.81 | 0.08 | — | 0.21 | — | 0.05 | 8.26 |

TABLE D-4

Stability data for lot # RB0067-010A.

| Sample Name | Formula | Assay Result mg/mL | Density (g/mL) | 0.915 (U-01) | Imp d | Imp h | Imp G | Imp E | 0.838 | 0.904 | Imp B | 1.064 | 1.071 (U-13) |
|---|---|---|---|---|---|---|---|---|---|---|---|---|---|
| Initial | RB0067-010A (no water) 40% PEG + BHA + BHT | 1.006 | 1.21 | — | — | — | 0.06 | — | — | — | — | — | — |
| 3D60C | | 0.975 | 1.21 | 0.12 | — | — | 0.83 | — | — | — | — | — | — |
| 1 m-25/60 | | 1.003 | 1.21 | — | — | — | 0.13 | — | — | — | — | — | — |
| 2 m-25/60 | | 1.015 | 1.21 | — | — | — | 0.17 | — | — | — | — | — | — |
| 3 m-25/60 | | 0.984 | 1.21 | 0.05 | — | — | 0.21 | — | — | — | — | — | — |
| 6 m-25/60 | | 0.999 | 1.21 | — | — | 0.03 | 0.39 | — | — | — | — | — | — |
| 2 w-40/75 | | 0.983 | 1.21 | — | — | — | 0.25 | — | — | — | — | — | — |
| 1 m-40/75 | | 0.995 | 1.21 | 0.13 | — | — | 0.71 | — | — | — | — | — | — |
| 2 m-40/75 | | 0.980 | 1.21 | 0.21 | — | — | 1.57 | — | — | — | 0.05 | — | 0.10 |
| 3 m-40/75 | | 0.926 | 1.21 | — | — | — | 2.15 | 0.06 | — | — | 0.12 | 0.24 | — |
| 6 m-40/75 | | 0.845 | 1.21 | — | 0.10 | 0.06 | 3.94 | — | 0.79 | 0.11 | 0.26 | — | — |

| Sample Name | Keto (U-03) | (U-04) | Enol 1 (U-08) | 1.473 | 1.598 | Enol 2 (U-05) | 1.674 | 2.618 | 3.120 | 3.169 | Asym dimer | Total Imp (%) |
|---|---|---|---|---|---|---|---|---|---|---|---|---|
| Initial | — | — | — | — | — | — | — | — | — | — | — | 0.06 |
| 3D60C | 0.19 | 0.22 | — | — | — | 0.17 | — | — | — | — | — | 1.53 |
| 1 m-25/60 | — | — | — | — | — | — | — | — | — | — | — | 0.13 |
| 2 m-25/60 | — | — | — | — | — | — | — | — | — | — | — | 0.17 |
| 3 m-25/60 | — | — | — | — | 0.06 | — | — | — | — | — | 0.06 | 0.38 |
| 6 m-25/60 | 0.05 | — | — | — | 0.11 | — | — | — | — | — | 0.07 | 0.93 |
| 2 w-40/75 | — | — | 0.08 | — | — | 0.05 | 0.05 | — | — | — | — | 0.43 |
| 1 m-40/75 | 0.05 | 0.10 | — | — | — | 0.07 | 0.06 | — | — | — | — | 1.12 |

TABLE D-4-continued

Stability data for lot # RB0067-010A.

| | | | | | | | | | | | |
|---|---|---|---|---|---|---|---|---|---|---|---|
| 2 m-40/75 | 0.14 | 0.35 | — | — | — | — | — | — | — | — | 2.52 |
| 3 m-40/75 | 0.33 | — | — | 0.06 | 0.92 | — | — | 0.11 | — | — | 0.06 | 4.72 |
| 6 m-40/75 | 1.22 | — | — | — | 2.62 | — | — | — | 0.10 | 0.37 | 0.05 | 10.29 |

TABLE D-5

Stability data for lot # RB0067-011A.

| Sample Name | Formula | Assay Result (mg/mL) | Density (g/mL) | 0.915 (U-01) | Imp d | Imp h | 0.838 | Imp G | Imp B | Asym Dimer | 1.068 | 1.102 |
|---|---|---|---|---|---|---|---|---|---|---|---|---|
| Initial | RB0067-011A | 0.998 | 1.19 | — | — | — | — | 0.14 | — | — | — | — |
| 3D60C | (no water) | 0.983 | 1.19 | — | — | — | — | 0.21 | — | — | — | — |
| 1 m-25/60 | 50% | 1.013 | 1.19 | — | — | — | — | 0.08 | — | — | — | — |
| 2 m-25/60 | PEG + | 1.012 | 1.19 | — | — | — | — | 0.11 | — | — | — | — |
| 3 m-25/60 | 5% PG + | 0.986 | 1.19 | — | — | — | — | 0.13 | — | 0.06 | — | — |
| 6 m-25/60 | BHA + | 1.000 | 1.19 | — | — | 0.03 | 0.03 | 0.20 | 0.03 | 0.06 | — | — |
| 2 w-40/75 | BHT | 0.987 | 1.19 | 0.06 | — | — | — | 0.12 | — | — | — | — |
| 1 m-40/75 | | 0.999 | 1.19 | — | — | — | — | 0.33 | — | — | — | — |
| 2 m-40/75 | | 0.985 | 1.19 | 0.08 | — | — | — | 0.70 | — | — | — | — |
| 3 m-40/75 | | 0.954 | 1.19 | 0.21 | — | — | — | 1.12 | 0.08 | 0.06 | 10.18 | — |
| 6 m-40/75 | | 0.900 | 1.19 | — | 0.07 | 0.05 | 0.41 | 2.47 | — | 0.06 | — | 0.19 |

| Sample Name | 1.064 U-13 | Keto (U-03) | (U-04) | Enol 2 (U-05) | 1.596 | 1.674 | 2.617 | 3.145 | 3.328 | Total Imp (%) |
|---|---|---|---|---|---|---|---|---|---|---|
| Initial | — | — | — | — | — | — | — | — | — | 0.14 |
| 3D60C | — | 0.12 | 0.28 | 0.18 | — | — | — | — | — | 0.78 |
| 1 m-25/60 | — | — | — | — | — | — | — | — | — | 0.08 |
| 2 m-25/60 | — | — | — | — | — | — | — | — | — | 0.11 |
| 3 m-25/60 | — | — | — | 0.08 | 0.04 | — | — | — | — | 0.31 |
| 6 m-25/60 | — | — | — | 0.09 | 0.07 | — | — | — | 0.10 | 0.81 |
| 2 w-40/75 | — | — | — | 0.07 | — | 0.05 | — | — | — | 0.30 |
| 1 m-40/75 | — | 0.05 | — | 0.11 | — | — | — | — | — | 0.49 |
| 2 m-40/75 | 0.73 | 0.13 | 0.20 | 0.11 | — | — | — | — | — | 1.95 |
| 3 m-40/75 | — | 0.25 | — | 0.11 | 0.54 | — | 0.05 | — | — | 2.76 |
| 6 m-40/75 | — | 0.94 | — | — | 2.52 | — | — | 0.21 | — | 7.48 |

TABLE D-6

Stability data for lot # RB0067-012A.

| Sample Name | Formula | Assay Result (mg/mL) | Density (g/mL) | 0.915 (U-01) | 0.838 | Imp d | Imp h | Imp G | Asym Dimer | Imp B | 1.102 |
|---|---|---|---|---|---|---|---|---|---|---|---|
| Initial | RB0067-012A (no water) | 1.010 | 1.20 | — | — | — | — | 0.15 | — | — | — |
| 3D60C | | 0.986 | 1.20 | — | — | — | — | 0.38 | — | — | — |
| 1 m-25/60 | | 1.002 | 1.20 | — | — | — | — | 0.09 | — | — | — |
| 2 m-25/60 | 40% | 1.016 | 1.20 | 0.06 | — | — | — | 0.25 | — | — | — |
| 3 m-25/60 | PEG + | 0.981 | 1.20 | — | — | — | — | 0.16 | 0.06 | — | — |
| 6 m-25/60 | 5% PG + | 0.993 | 1.19 | — | — | — | 0.03 | 0.27 | 0.06 | — | — |
| 2 w-40/75 | BHA + | 0.982 | 1.20 | 0.05 | — | — | — | 0.17 | — | — | — |
| 1 m-40/75 | BHT | 0.993 | 1.20 | 0.06 | — | — | — | 0.53 | — | — | — |
| 2 m-40/75 | | 0.987 | 1.20 | 0.12 | — | — | — | 1.08 | — | — | — |
| 3 m-40/75 | | 0.943 | 1.20 | 0.29 | — | — | — | 1.41 | 0.06 | 0.08 | — |
| 6 m-40/75 | | 0.878 | 1.19 | — | 0.63 | 0.10 | 0.06 | 3.32 | 0.05 | — | 0.22 |

TABLE D-6-continued

Stability data for lot # RB0067-012A.

| Sample Name | 1.473 | 1.068 (U-06) | Keto (U-03) | (U-04) | 1.358 | Enol/ U-05 | 1.597 | 2.616 | Total imp (%) |
|---|---|---|---|---|---|---|---|---|---|
| Initial | — | — | — | — | — | — | — | — | 0.15 |
| 3D60C | — | 0.06 | 0.12 | 0.32 | — | 0.20 | — | — | 1.07 |
| 1 m-25/60 | — | — | — | — | — | — | — | — | 0.09 |
| 2 m-25/60 | — | — | — | — | — | — | — | — | 0.31 |
| 3 m-25/60 | — | — | — | — | — | — | 0.05 | — | 0.27 |
| 6 m-25/60 | — | — | 0.05 | — | — | — | — | — | 0.63 |
| 2 w-40/75 | — | — | — | — | 0.09 | 0.06 | 0.06 | — | 0.43 |
| 1 m-40/75 | — | — | — | 0.08 | — | 0.07 | — | — | 0.74 |
| 2 m-40/75 | — | 0.07 | 0.12 | 0.24 | — | — | — | — | 1.63 |
| 3 m-40/75 | 0.05 | 0.18 | 0.25 | — | — | 0.05 | 0.63 | 0.07 | 3.15 |
| 6 m-40/75 | — | 1.07 | 0.98 | — | — | — | 2.73 | — | 9.67 |

TABLE D-7

Stability data for lot # RB0067-019A.

| Sample Name | Formula | Assay Result (mg/mL) | Density (g/mL) | 0.195 | Imp H | Imp G | Imp N | 1.091 | Keto (U-03) | 1.101 |
|---|---|---|---|---|---|---|---|---|---|---|
| Initial | RB0067-019A | 1.014 | 1.18 | — | — | ND | — | — | — | — |
| 3D60C | (no water) | 0.999 | 1.18 | — | — | 0.19 | — | 0.10 | 10.11 | — |
| 1 m-25/60 | 50% PEG + | 0.999 | 1.18 | — | — | 0.17 | — | — | — | — |
| 2 m-25/60 | 5% PG + + | 1.010 | 1.18 | 0.09 | — | 0.15 | — | — | — | — |
| 3 m-25/60 | BHA + EM | 0.985 | 1.18 | — | — | 0.07 | — | — | — | — |
| 6 m-25/60 |  | 1.011 | 1.19 | — | 0.04 | 0.07 | — | — | 0.04 | — |
| 2 w-40/75 |  | 0.995 | 1.18 | — | — | 0.04 | — | — | — | — |
| 1 m-40/75 |  | 0.999 | 1.18 | — | — | 0.19 | 0.14 | — | — | — |
| 2 m-40/75 |  | 0.993 | 1.18 | — | — | 0.19 | — | — | 0.06 | — |
| 3 m-40/75 |  | 0.970 | 1.18 | — | — | 0.09 | — | — | 0.11 | — |
| 6 m-40/75 |  | 0.987 | 1.19 | — | 0.06 | 0.08 | — | — | 0.24 | 0.06 |

| Sample Name | 1.259 | 1.358 | 1.432 (U-08) | U-05/ Enol 2 | 1.654 Asym Di | 1.595 | 1.674 | 3.045 | Total Imp (%) |
|---|---|---|---|---|---|---|---|---|---|
| Initial | — | — | — | — | — | — | 0.04 | — | 0.04 |
| 3D60C | — | 0.15 | 10.08 | 0.34 | — | — | 0.06 | — | 1.03 |
| 1 m-25/60 | — | — | — | — | — | — | — | — | 0.17 |
| 2 m-25/60 | — | — | — | — | — | — | — | — | 0.24 |
| 3 m-25/60 | — | — | — | 0.06 | 0.06 | — | — | — | 0.19 |
| 6 m-25/60 | — | — | — | 0.11 | 0.06 | — | — | 0.06 | 0.42 |
| 2 w-40/75 | — | — | — | 0.07 | — | — | 0.05 | — | 0.16 |
| 1 m-40/75 | — | — | — | — | 0.05 | — | — | — | 0.38 |
| 2 m-40/75 | — | — | — | 0.17 | — | — | — | — | 0.42 |
| 3 m-40/75 | — | — | — | 0.16 | 0.06 | 0.09 | — | — | 0.63 |
| 6 m-40/75 | 0.06 | — | — | 0.11 | 0.06 | 0.16 | — | 0.06 | 1.25 |

TABLE D-8

Stability data for lot # RB0067-014A.

| Sample Name | Formula | Assay Result (mg/mL) | Density (g/mL) | 0.710 (U-01) | Imp G | 0.336 | 0.373 | 0.836 | 1.063 | Imp B | Imp f |
|---|---|---|---|---|---|---|---|---|---|---|---|
| Initial | RB0067-014A | 1.008 | 1.19 | — | 0.05 | — | — | — | — | — | — |
| 3 d 60° C. | 50 % PEG + 5 | 0.990 | 1.19 | — | 0.16 | — | — | — | — | — | — |
| 1 m-25/60 | % Purified water | 1.000 | 1.19 | — | 0.15 | — | — | — | — | — | — |
| 2 m-25/60 | BHA + BHT + | 1.007 | 1.19 | — | 0.16 | — | — | — | — | — | — |
| 3 m-25/60 | maltose | 0.990 | 1.19 | — | ND | — | — | — | — | — | — |
| 2 w-40/75 |  | 1.008 | 1.19 | 0.06 | 0.06 | — | — | — | — | — | — |

TABLE D-8-continued

Stability data for lot # RB0067-014A.

| | | | | | | | | | | |
|---|---|---|---|---|---|---|---|---|---|---|
| 1 m-40/75 | 1.000 | 1.19 | — | 0.23 | — | — | — | — | — | — |
| 2 m-40/75 | 0.987 | 1.19 | — | 0.38 | — | — | — | — | — | — |
| 3 m-40/75 | 0.968 | 1.19 | — | 0.37 | 0.06 | 0.05 | 0.06 | 0.08 | 0.06 | 0.07 |

| Sample Name | Keto (U-03) | (U-04) | 1.358 | Enol 1 (U-08) | Enol 2 (U-05) | 1.536 | 1.596 | 1.672 | Total Imp (%) |
|---|---|---|---|---|---|---|---|---|---|
| Initial | — | — | — | — | — | — | — | — | 0.05 |
| 3 d 60° C. | 0.12 | 0.15 | — | 0.09 | 0.38 | — | — | — | 0.96 |
| 1 m-25/60 | — | — | — | — | — | — | — | — | 0.15 |
| 2 m-25/60 | — | — | — | — | — | — | — | — | 0.16 |
| 3 m-25/60 | — | — | — | — | 0.07 | — | — | — | 0.13 |
| 2 w-40/75 | 0.05 | — | 0.06 | 0.04 | 0.11 | 0.05 | — | 0.07 | 0.50 |
| 1 m-40/75 | 0.06 | — | — | — | 0.15 | — | — | — | 0.48 |
| 2 m-40/75 | 0.09 | 0.10 | — | — | 0.17 | — | — | — | 0.74 |
| 3 m-40/75 | 0.18 | — | — | — | 0.17 | — | 0.37 | — | 1.57 |

TABLE D-9

Stability data for lot # RB0067-016A.

| Sample Name | Formula | Assay Result (mg/mL) | Density (g/mL) | 0.452 | 0.226 (U-10) | Imp H | Imp G | dimer Asym | 1.068 | 1.131 | 1.182 | 1.211 |
|---|---|---|---|---|---|---|---|---|---|---|---|---|
| Initial | RB0067-016A | 1.011 | 1.18 | — | — | — | 0.11 | — | — | — | — | — |
| 3 d 60° C. | 50% PEG + | 0.980 | 1.18 | — | 0.12 | — | 0.14 | — | 0.12 | — | — | — |
| 1 m-25/60 | 10% PW | 1.013 | 1.18 | — | — | — | 0.16 | — | — | — | — | — |
| 2 m-25/60 | BHA + BHT + | 1.006 | 1.18 | 0.08 | — | — | 0.16 | — | — | — | — | — |
| 3 m-25/60 | maltose + | 0.989 | 1.18 | — | — | 0.05 | 0.07 | 0.06 | — | — | — | — |
| 2 w-40/75 | EDTA | 1.010 | 1.18 | — | — | — | 0.05 | — | — | 0.04 | — | — |
| 1 m-40/75 | | 0.981 | 1.18 | — | — | — | 0.18 | — | 0.09 | 0.06 | 0.05 | — |
| 2 m-40/75 | | 0.951 | 1.18 | 0.10 | — | — | 0.24 | — | 0.25 | 0.36 | 0.09 | — |
| 3 m-40/75 | | 0.914 | 1.18 | — | — | 0.07 | 0.18 | 0.06 | 0.29 | — | — | 0.21 |

| Sample Name | Keto/ U-03 | (U-04) | 1.331 | 1.341 | Enol 1 (U-08) | 1.5272 | Enol 2 (U-05) | 1.802 | 1.979 | Total Imp (%) |
|---|---|---|---|---|---|---|---|---|---|---|
| Initial | — | — | — | — | — | — | — | — | — | 0.11 |
| 3 d 60° C. | 0.22 | 0.09 | — | — | 0.30 | — | 1.30 | — | — | 2.17 |
| 1 m-25/60 | 0.08 | — | — | — | — | — | 0.24 | — | — | 0.48 |
| 2 m-25/60 | 0.13 | — | — | — | 0.09 | — | 0.24 | — | — | 0.70 |
| 3 m-25/60 | 0.19 | — | — | — | 0.12 | — | 0.54 | — | — | 1.09 |
| 2 w-40/75 | 0.18 | 0.07 | — | — | 0.19 | — | 0.80 | — | — | 1.66 |
| 1 m-40/75 | 0.24 | 0.23 | — | — | 0.29 | — | 1.27 | — | — | 2.41 |
| 2 m-40/75 | 0.30 | 0.39 | 0.12 | — | 0.47 | — | 2.01 | — | — | 4.33 |
| 3 m-40/75 | 0.40 | — | — | 1.08 | 0.54 | 0.11 | 2.27 | 0.66 | 0.15 | 6.43 |

Example E: Stability Data for Batches with Larger Scale

Reproducibility batch RB0067-031A, which has a batch size of 2.4 liter, was manufactured according to the same formulation of RB0067-019A. New batch RB0067-039A, with a batch size of 1 liter, was manufactured according to the formulation shown in Table E-1. A new batch RB0067-046A was manufactured according to the formulation shown in Table E-1 and was placed into 16-ounce glass amber bottles with a net weight of not more than 550 g and 16-ounce HDPE bottles with a net weight of 568 gram. Another 10-liter batch RB0067-052A was manufactured according to the formulation shown in Table E-1. The four batches above were tested for assay content and impurities at different timepoints such as initial, after 4 days when heated at about 60° C., after 1 month, 2 months, 3 months, and 6 months when stored at about 25° C. and about 60% RH, and after 1 month, 2 months, 3 months, and 6 months when stored at about 40° C. and about 75% RH. The testing results for RB0067-031A, RB0067-039A, RB0067-046A, and RB0067-052A are summarized in Table E-2, Table E-3, Table E-4, and Table E-5, respectively. Impurities observed at a level below 0.05% are not shown in the tables but are monitored.

TABLE E-1

Formulation for lot# RB0067-039A, RB0067-046A, and RB0067-052A.

| Ingredient | Quantity % w/v RB0067-039A, RB0067-046A, and RB0067-052A |
|---|---|
| Hydrocortisone | 0.1 |
| PEG 400 | 50 |

TABLE E-1-continued

Formulation for lot# RB0067-039A, RB0067-046A, and RB0067-052A.

| Ingredient | Quantity % w/v RB0067-039A, RB0067-046A, and RB0067-052A |
|---|---|
| Butylated Hydroxy Anisole (BHA) | 0.01 |
| Methylparaben (MP) | 0.18 |
| Propylparaben (PP) | 0.02 |
| Sucralose | 1 |
| Berry Flavor 13.17579 | 0.2 |
| Propylene glycol | 5 |
| Ethyl maltol | 0.2 |
| Glycerin | 62.2 |

TABLE E-2

Stability data for lot # RB0067-031A.

| Lot number | Time point | Assay (%) | Density (g/mL) | MP (%) | PP (%) | BHA (%) | Imp H | Imp G | Imp B | Keto | Hydrocortisone lacetate | 1.603 | Enol 1 | Enol 2 | Asym Dimer | Total Imp (%) |
|---|---|---|---|---|---|---|---|---|---|---|---|---|---|---|---|---|
| RB0067-031A | Initial - new | 95.9 | 1.17 | 95.1 | 97.2 | 103.1 | — | 0.06 | — | — | — | — | — | — | 0.06 | 0.12 |
| (2.4 lit batch) | 1 m-25/60 | 99.0 | 1.17 | 100.8 | 100.7 | 104.7 | 0.03 | 0.08 | — | — | 0.03 | — | — | 0.04 | 0.06 | 0.33 |
| 0.1% | 2 m-25/60 | 97.4 | 1.17 | 97.7 | 97.3 | 101.3 | — | 0.10 | — | 0.03 | 0.03 | — | — | 0.06 | 0.06 | 0.33 |
| Ethyl | 3 m-25/60 | 98.7 | 1.19 | 98.6 | 100.4 | 95.5 | 0.03 | 0.07 | — | 0.04 | — | 0.04 | — | 0.09 | 0.06 | 0.43 |
| Maltol | 1 m-40/75 | 98.1 | 1.17 | 99.8 | 100.1 | 104.0 | 0.03 | 0.13 | 0.02 | 0.06 | 0.03 | — | 0.04 | 0.17 | 0.06 | 0.66 |
|  | 2 m-40/75 | 96.7 | 1.17 | 97.6 | 97.2 | 100.4 | — | 0.14 | 0.03 | 0.13 | 0.02 | 0.06 | 0.04 | 0.20 | 0.06 | 0.87 |
|  | 3 m-40/75 | 98.7 | 1.19 | 99.4 | 101.2 | 95.0 | 0.05 | 0.10 | — | 0.18 | — | 0.13 | — | 0.20 | 0.06 | 1.06 |

TABLE E-3

Stability data for lot # RB0067-039A.

| Formula | Time point | Assay (%) | Density (g/mL) | MP (%) | PP (%) | BHA (%) | 0.932 | 1.056 | Cortisone | Imp G |
|---|---|---|---|---|---|---|---|---|---|---|
| RB0067- | Initial | 100.8 | 1.18 | 100.1 | 96.8 | 105.8 | 0.12 | — | — | 0.06 |
| 039A | 1 m-25/60 | 99.9 | 1.18 | 101.2 | 95.4 | 104.4 | — | — | — | 0.06 |
| 1 liter | 2 m-25/60 | 100.9 | 1.18 | 101.1 | 95.5 | 104.9 | — | — | — | 0.09 |
| Batch | 3 m-25/60 | 101.4 | 1.18 | 102.0 | 95.7 | 105.5 | — | — | — | — |
| 0.2% | 6 m-25/60 | 100.3 | 1.19 | 100.8 | 96.2 | 104.4 | — | — | 0.07 | — |
| Ethyl | 1 m-40/75 | 100.1 | 1.18 | 101.5 | 95.9 | 104.3 | — | — | — | 0.05 |
| Maltol | 2 m-40/75 | 97.5 | 1.18 | 98.1 | 92.4 | 100.5 | — | — | — | 0.07 |
|  | 3 m-40/75 | 100.2 | 1.18 | 101.2 | 95.0 | 102.8 | — | 0.09 | 0.07 | 0.12 |
|  | 6 m-40/75 | 98.8 | 1.19 | 100.3 | 95.7 | 102.7 | — | — | 0.07 | — |

| Formula | Imp B | Keto | Hydro acetate | 1.479 | 1.592 | 1.550 | Enol 2 | Asym Dimer | Total Imp (%) |
|---|---|---|---|---|---|---|---|---|---|
| RB0067- | — | — | — | — | — | — | — | 0.06 | 0.24 |
| 039A | — | — | 0.03 | — | — | — | — | 0.06 | 0.18 |
| 1 liter | 0.02 | 0.03 | 0.03 | — | — | — | 0.03 | 0.06 | 0.31 |
| Batch | — | — | — | — | — | — | — | 0.06 | 0.06 |
| 0.2% | — | 0.06 | — | — | — | — | — | 0.06 | 0.28 |
| Ethyl | 0.02 | 0.06 | 0.03 | — | 0.05 | — | 0.08 | 0.06 | 0.40 |
| Maltol | 0.03 | 0.10 | 0.03 | — | — | — | 0.08 | 0.06 | 0.52 |
|  | — | 0.14 | — | 0.06 | — | — | 0.08 | 0.06 | 0.72 |
|  | — | 0.23 | — | — | — | 0.11 | — | 0.06 | 0.74 |

TABLE E-4

Stability data for lot # RB0067-046A.

| Formula | Time point | Density (g/mL) | Assay (%) | MP % | PP (%) | BHA (%) | RRT 0.393 | RRT 0.622 | Imp G | Imp B | cortisone |
|---|---|---|---|---|---|---|---|---|---|---|---|
| RB0067-046A | Composite | 1.1741 | 98.4 | 90.8 | 96.4 | 94.4 | — | 0.03 | 0.06 | — | — |
| | 14 d/60° C. | 1.1867 | 99.0 | 91.8 | 98.9 | 95.9 | — | 0.04 | 0.22 | — | — |
| | 1 m-25/60 | 1.1895 | 100.4 | 92.4 | 97.9 | 96.1 | — | 0.04 | — | — | — |
| | 3 m-25/60 | 1.1805 | 98.2 | 90.6 | 98.1 | 94.2 | — | 0.05 | 0.07 | — | 0.02 |
| | 1 m-40/75 | 1.1786 | 98.8 | 91.3 | 97.2 | 95.1 | — | — | 0.13 | — | — |
| | 3 m-40/75 | 1.1796 | 97.5 | 90.6 | 98.3 | 94.2 | 0.11 | 0.03 | 0.11 | 0.06 | 0.03 |

| Formula | Hydro Acetate | Keto Imp | 1.548 | Cortisol Imp1 | Imp Enol #2 | RRT 2.912 | Unsym Dimer | RRT 3.191 | Total Imp (%) |
|---|---|---|---|---|---|---|---|---|---|
| RB0067-046A | 0.03 | — | — | — | 0.03 | 0.03 | 0.06 | — | 0.20 |
| | — | 0.09 | — | — | 0.40 | — | — | 0.13 | 0.88 |
| | — | — | — | — | — | — | 0.06 | — | 0.10 |
| | — | 0.04 | — | — | 0.09 | — | 0.06 | — | 0.52 |
| | — | 0.06 | — | — | 0.22 | — | 0.06 | — | 0.48 |
| | — | 0.19 | 0.14 | 0.06 | 0.21 | — | 0.06 | — | 1.33 |

TABLE E-5

Stability data for lot # RB0067-052A.

| Lot Number | Time point | Assay (%) | Density (g/mL) | MP (%) | PP (%) | BHA (%) | Imp G | Hydrocortisone acetate | 2.912 | Asym Dimer | RRT 3.026 | Total Imp (%) |
|---|---|---|---|---|---|---|---|---|---|---|---|---|
| RB0067-052A 10 lit batch | Initial | 100.4 | 1.1889 | 99.5 | 99.5 | 97.2 | 0.06 | 0.03 | 0.03 | 0.06 | 10.02 | 0.19 |

Example F: Evaluation of Photostability drug product was found to be sensitive to white light, therefore, white light exposure study was conducted on batch RB0067-031A (closed bottles in the photostability chamber) and on batch RB0067-042A at initial timepoint, and after exposure to white light for 3 days, 6 days, and 9 days. Samples were collected in glass vials, wrapped in aluminum foil and tested. Results reported shows no impact of white light is expected on hydrocortisone liquid oral formulations or during the manufacturing process since manufacturing is done under white light. The assay and impurity data for the white light exposure experiments is shown in Table F-i and Table F-2.

TABLE F-1

Photostability of RB0067-031A.

| Timepoint | Formula | Result Assay (%) | Density (g/mL) | MP (%) | PP (%) | BHA (%) | Imp G | Keto | Hydro-cortisone acetate | Enol 1 | Enol 2 | Asym Dimer | 2.949 | Imp Total (%) |
|---|---|---|---|---|---|---|---|---|---|---|---|---|---|---|
| Initial | RB0067-031A (240 mL as compared to 2.4 lit the dose batch) specified in ICH guidelines* | 95.9 | 1.17 | 95.1 | 97.2 | 103.1 | 0.06 | — | — | — | — | 0.06 | — | 0.12 |
| 5 times white light exposure | | 98.5 | 1.17 | 99.1 | 99.2 | 100.7 | 0.08 | 0.04 | 0.03 | — | 0.06 | 0.06 | — | 0.30 |
| 5 times UV exposure as compared to the dose specified in ICH guidelines* | | 98.2 | 1.17 | 99.0 | 98.9 | 102.6 | 0.07 | — | 0.03 | — | 0.05 | 0.06 | — | 0.25 |

*ICH guideline: stability testing: photostability testing of new drug substances and products Q1B.

TABLE F-2

Stability of RB0067-042A under white light exposure.

| Timepoint | Formula | Assay Result (%) | Density (g/mL) | MP (%) | PP (%) | BHA (%) | Imp G | Keto | Hydrocortisone acetate | Enol 1 | Enol 2 | Asym Dimer | 2.949 | Total Imp (%) |
|---|---|---|---|---|---|---|---|---|---|---|---|---|---|---|
| Initial | RB0067-042A | 98.4 | 1.16 | 97.3 | 103.1 | 95.9 | — | — | — | — | — | — | — | NT |
| 3-day white light | | 97.0 | 1.16 | 98.0 | 102.8 | 94.9 | 0.04 | — | 0.03 | — | — | 0.06 | 0.03 | 0.17 |
| 6-day white light | | 97.1 | 1.16 | 98.1 | 102.8 | 94.7 | 0.04 | — | 0.03 | — | — | 0.06 | 0.03 | 0.16 |
| 9-day white light | | 96.8 | 1.16 | 98.0 | 102.5 | 94.1 | 0.04 | — | 0.03 | — | — | 0.06 | 0.03 | 0.19 |

Example G: Evaluation of Container Material

The effect of container materials on the assay and impurity of the hydrocortisone liquid pharmaceutical composition batches was evaluated. Batch RB0067-019A was filled in 30 mL glass bottles and half-filed in HDPE bottles. Batch RB0067-019A in HDPE bottle was tested for assay and impurity after 6 months when placed at about 25° C. and about 60% RH and at about 40° C. and about 75% RH. Batch RB0067-019A in glass bottles were tested for assay and impurity after 4 months and 6 months when placed at about 25° C. and about 60% RH and at about 40° C. and about 75% RH. The testing results are summarized in Table G-1 and Table G-2. Impurities observed at a level below 0.05% are not shown in the tables but are monitored.

TABLE G-1

Stability of lot # RB0067-019A in HDPE container.

| Timepoint | Formula | Assay (%) | Density (g/mL) | MP (%) | PP (%) | BHA (%) | Imp H | Imp G | Keto | Enol 2 | Asym Dimer | 1.595 | Total Imp (%) |
|---|---|---|---|---|---|---|---|---|---|---|---|---|---|
| Initial | RB0067-019A Half-filled for HDPE bottles 1 liter batch | 101.4 | 1.18 | — | — | — | — | — | — | — | — | — | 0.04 |
| 6 m-25/60 HDPE | | 101.1 | 1.20 | 101.2 | 102.0 | 98.4 | 0.04 | 0.07 | 0.04 | 0.11 | | | 0.42 |
| 6 m-40/75 HDPE | | 98.7 | 1.20 | 100.2 | 100.8 | 95.7 | 0.06 | 0.08 | 0.24 | 0.11 | 0.06 | 0.16 | 1.25 |

TABLE G-2

Stability of lot # RB0067-019A in glass bottle container.

| Timepoint | Formula | Assay (%) | Density (g/mL) | MP (%) | PP (%) | BHA (%) | Imp H | Imp G | Imp B | 1.062 Imp N |
|---|---|---|---|---|---|---|---|---|---|---|
| Initial | RB0067-019A 30 mL glass bottles | 101.4 | 1.18 | — | — | — | — | — | — | — |
| 4 m-25/60-glass | | 99.5 | 1.18 | 101.2 | 100.0 | 97.3 | 0.02 | 0.24 | — | — |
| 6 m-25/60 glass | | 100.1 | 1.19 | 100.8 | 101.7 | 98.1 | 0.04 | 0.27 | — | — |
| 4 m-40/75 glass | | 96.1 | 1.18 | 100.2 | 99.1 | 95.0 | 0.03 | 0.25 | 0.06 | 0.45 |
| 6 m-40/75 glass | | 94.8 | 1.19 | 98.5 | 99.2 | 94.1 | 0.06 | 0.18 | 0.07 | — |

| Timepoint | Keto | Hydrocortisone Acetate | Enol 1 | Enol 2 | Asym Dimer | 1.595 | 1.645 | Imp F | Total Imp (%) |
|---|---|---|---|---|---|---|---|---|---|
| Initial | — | — | — | — | — | — | — | — | 0.04 |
| 4 m-25/60-glass | 0.08 | 0.03 | — | 0.16 | 0.06 | — | — | — | 0.77 |
| 6 m-25/60 glass | 0.12 | — | — | 0.21 | — | — | — | — | 1.10 |
| 4 m-40/75 glass | 0.46 | 0.03 | 0.13 | 0.50 | 0.06 | 0.26 | — | 0.07 | 2.74 |
| 6 m-40/75 glass | 0.56 | — | — | 0.44 | 0.06 | 0.26 | 0.12 | — | 2.99 |

Example H: Manufacturing Process

Some batches described in Examples C to E were manufactured following the steps described. PEG 400 was added in the compounding container, then preservatives and sweeteners were dissolved in the compounding container. Hydrocortisone and berry flavor were dissolved in the compounding container.

Propylene glycol was added in a side container, then ethyl maltol and BHA were dissolved to make propylene glycol solution. The propylene glycol solution was added to the compounding container. Finally, add sufficient quantity of glycerin.

Some batches described in Examples D and E were manufactured following the steps described. PEG 400 was added in the compounding container, then preservatives, sweeteners, and ethyl maltol were dissolved in the compounding container. Hydrocortisone and berry flavor were dissolved in the compounding container. Propylene glycol was added to the compounding container, and sufficient quantity of glycerin was added to the compounding container. Optionally, sample in compounding container can be filtered through a 5 μm disposable filter using an ALMATEC® pump and stored in a storage tank.

Some batches will be manufactured following the steps described. PEG 400 and propylene glycol were added in the compounding container, then preservatives, sweeteners, and ethyl maltol were dissolved in the compounding container. Hydrocortisone and berry flavor were dissolved in the compounding container.

Finally, add sufficient quantity of glycerin.

Example I: Exemplary Manufacturing Process

Exemplary procedures of making a formulation of the disclosure are provided as follows.

Weigh methylparaben, propylparaben, sucralose, ethyl maltol, butylated hydroxyanisole (BHA), and hydrocortisone; polyethylene glycol 400, propylene glycol, flavor and glycerin are weighed during the during the process Record the tare weight of a compounding tank and lid Add polyethylene glycol 400 and propylene glycol to the compounding tank and mix the content at a speed from about 450 to about to 1000 rpm (e.g., at about 750 rpm)

Add methylparaben and propylparaben to the compounding tank and mix for not less than 15 min at a speed from about 450 rpm to about 1000 rpm (e.g., at about 750 rpm)

Add sucralose to the compounding tank and mix for not less than 45 minutes at a speed from about 450 rpm to about 1000 rpm.

Add ethyl maltol and BHA to the compounding tank and mix for not less than 60 minutes at a speed from about 450 rpm to about 1000 rpm.

Add hydrocortisone to the compounding tank and mix for not less than 60 min at a speed from about 750 rpm to about 1350 rpm (e.g., at about 1000 rpm).

Add Berry Mixed Flavor WONF, WS Natural 13.17579 to the compounding tank and mix for 15 minutes at a speed from about 750 rpm to about 1350 rpm (e.g., at about 1000 rpm)

Add the first portion of glycerin to the compounding tank and mix for not less than 60 minutes at a speed from 600 rpm to 1200 rpm (e.g., at about 850 rpm)

Add remaining portion of glycerin to the compounding tank and QS (add sufficient quantity) to weight and mix for not less than 120 minutes at a speed from about 750 rpm to about 1400 rpm (e.g., 1050 rpm)

Filter the solution from the compounding tank through a 5-micron filter placed in the filter housing into a storage tank The final solution is stored in the storage tank until packaging Package the final solution into a 16 oz white HDPE bottle with 28 mm CRC closures with induction foil.

Example J: In-Use Stability Testing

In-use stability testing was performed using the batch RB0067-052A manufactured according to the formulation in Table E-1. The purpose of performing in-use stability testing is to establish a time period during which the liquid pharmaceutical formulation can be used while retaining acceptable stability once the container is opened. The liquid pharmaceutical formulation from batch RB0067-052A was dispensed into 4 oz and 8 oz pharmacy bottles, respectively. The assay contents and impurity analysis were performed on the drug product at initial time point and after the bottles were opened and stored at ambient conditions (from about 15° C. to about 30° C.) for 90 days. The testing results are summarized in Table J-1.

TABLE J-1

In-use stability data for lot # RB0067-052A.

| Lot Number | Time point | Assay (%) | Density (g/mL) | MP (%) | PP (%) | BHA (%) | Imp G | Hydro acetate | Cortisone | Cortisol Imp-2 Enol | Keto | Asym Dimer | Total Imp (%) |
|---|---|---|---|---|---|---|---|---|---|---|---|---|---|
| RB0067-052A | Initial - 4 oz | 99.0 | 1.889 | 95.7 | 99.4 | 100.4 | — | — | — | — | — | 0.06 | 0.06 |
| | Initial - 8 oz | 99.4 | | 96.1 | 99.9 | 101.2 | — | — | — | — | — | 0.06 | 0.06 |
| | 4 oz 90 days | 99.3 | 1.1928 | 100.1 | 99.9 | 97.6 | 0.05 | ND | 0.02 | 0.02 | 0.04 | 0.06 | 0.24 |
| | 8 oz 90 days | 99.3 | | 100.1 | 99.9 | 98.0 | 0.04 | ND | 0.02 | 0.02 | 0.03 | 0.06 | 0.21 |

Example K: Additional Formulations

Additional hydrocortisone oral liquid compositions using various concentration of hydrocortisone, preservatives, flavoring agents, sweeteners, or non-aqueous liquid carriers, or combinations thereof, can be prepared according to Tables K-1 to K-3.

TABLE K-1

Hydrocortisone Compositions with Varied Preservatives, Sweeteners, and Flavoring Agents.

Quantity % w/v (batch size: 100 mL)

| Ingredient | F-1 | F-2 | F-3 | F-4 | F-5 | F-6 | F-7 | F-8 |
|---|---|---|---|---|---|---|---|---|
| Hydrocortisone | 0.01 | 0.02 | 0.05 | 0.1 | 0.2 | 0.5 | 1 | 2 |
| Propylene glycol | 1 | 2 | 2.5 | 5 | 5 | 7.5 | 10 | 10 |
| PEG 400 | 30 | 35 | 40 | 45 | 50 | 55 | 60 | 70 |
| BHA | 0.005 | 0.01 | 0.01 | 0.01 | 0.01 | 0.02 | 0.02 | 0.02 |
| BHT | | | | 0-0.05 | | | | |
| Benzoic acid or sodium benzoate | | | | 0-2 | | | | |
| Methyl-paraben | 0.18 | 0.18 | 0.18 | 0.18 | 0.18 | 0.18 | 0.18 | 0.18 |
| Propyl-paraben | 0.02 | 0.02 | 0.02 | 0.02 | 0.02 | 0.02 | 0.02 | 0.02 |
| Sweetener(s) | Glucose, fructose, sucrose, lactose, maltose, xylitol, tagatose, sucralose, maltitol, isomaltulose, hydrogenated isomaltulose, lactitol, sorbitol, erythritol, trehalose, maltodextrin, polydextrose, or a combination thereof: 0.05-5 | | | | | | | |
| Flavoring agent(s) | Vanillin, grape flavor, caramel flavor, maltol, raspberry flavor, fruity flavor, berry flavor, 4-hydroxy-3-methoxybenzaldehyde, methyl anthranilate, 3,5-dimethyl-1,2-cyclopentadione, 4-(4-hydroxyphenyl)butan-2-one, ethyl maltol, ethyl propionate, or a combination thereof: 0.05-1 | | | | | | | |
| Glycerin | Qs to 100 mL | Qs 100 mL | Qs 100 mL | Qs 100 mL | Qs 100 mL | Qs 100 mL | Qs 100 mL | Qs 100 mL |

TABLE K-2

Hydrocortisone Compositions with Varied Preservatives.

Quantity % w/v (batch size: 100 mL)

| Ingredient | F-9 | F-10 | F-11 | F-12 | F-13 | F-14 | F-15 | F-16 |
|---|---|---|---|---|---|---|---|---|
| Hydrocortisone | 0.01 | 0.02 | 0.05 | 0.1 | 0.2 | 0.5 | 1 | 2 |
| Propylene glycol | 1 | 2 | 2.5 | 5 | 5 | 7.5 | 10 | 10 |
| Antioxidant | Vitamin A, monothioglycerol, ascorbic acid, sodium bisulfite, sodium sulfite, α-Tocopherol acetate (vitamin E), butylated hydroxyanisole (BHA), butylated hydroxytoluene (BHT), or a combination thereof: 0-0.5 | | | | | | | |
| Antimicrobial agent(s) | Methyl paraben, ethyl paraben, propyl paraben, benzoic acid or a pharmaceutically acceptable salt thereof (e.g., sodium benzoate), sorbic acid or a pharmaceutically acceptable salt thereof, phenoxyethanol, benzyl alcohol, propionic acid, or a combination thereof: 0-2 | | | | | | | |
| Chelating agent(s) | Disodium ethylenediaminetetraacetic acid, polyphosphates, citric acid, calcium disodium edetate, ethylenediaminetetraacetic acid (EDTA), or a combination thereof: 0-2 | | | | | | | |
| Berry Flavor | 0.2 | 0.2 | 0.2 | 0.2 | 0.2 | 0.2 | 0.2 | 0.2 |
| Ethyl maltol | 0.2 | 0.2 | 0.2 | 0.2 | 0.2 | 0.2 | 0.2 | 0.2 |
| Glycerin | Qs 100 mL | Qs 100 mL | Qs 100 mL | Qs 100 mL | Qs 100 mL | Qs 100 mL | Qs 100 mL | Qs 100 mL |
| Sucralose | 1 | 1 | 1 | 1 | 1 | 1 | 1 | 1 |

TABLE K-3

Hydrocortisone Compositions with Varied Non-Aqueous Liquid Carriers.

Quantity % w/v (batch size: 100 mL)

| Ingredient | F-17 | F-18 | F-19 | F-20 | F-21 | F-22 | F-23 | F-24 | F-25 |
|---|---|---|---|---|---|---|---|---|---|
| Hydrocortisone | 0.05 | 0.05 | 0.05 | 0.1 | 0.1 | 0.1 | 0.2 | 0.2 | 0.2 |
| Ethanol | | | | | 0-5 | | | | |
| Labrasol | | | | | 0-5 | | | | |
| Propylene glycol | 0 | 5 | 10 | 0 | 5 | 10 | 0 | 5 | 10 |
| PEG 400 | 40-70 | 35-75 | 30-70 | 40-70 | 35-75 | 30-70 | 40-70 | 35-75 | 30-70 |
| BHA | 0.01 | 0.01 | 0.01 | 0.01 | 0.01 | 0.01 | 0.01 | 0.01 | 0.01 |
| Methyl-paraben | 0.18 | 0.18 | 0.18 | 0.18 | 0.18 | 0.18 | 0.18 | 0.18 | 0.18 |

TABLE K-3-continued

Hydrocortisone Compositions with Varied Non-Aqueous Liquid Carriers.

| | Quantity % w/v (batch size: 100 mL) | | | | | | | | |
|---|---|---|---|---|---|---|---|---|---|
| Ingredient | F-17 | F-18 | F-19 | F-20 | F-21 | F-22 | F-23 | F-24 | F-25 |
| Propyl-paraben | 0.02 | 0.02 | 0.02 | 0.02 | 0.02 | 0.02 | 0.02 | 0.02 | 0.02 |
| Sucralose | 1 | 1 | 1 | 1 | 1 | 1 | 1 | 1 | 1 |
| Berry Flavor | 0.2 | 0.2 | 0.2 | 0.2 | 0.2 | 0.2 | 0.2 | 0.2 | 0.2 |
| Ethyl maltol | 0.2 | 0.2 | 0.2 | 0.2 | 0.2 | 0.2 | 0.2 | 0.2 | 0.2 |
| Glycerin | Qs 100 mL | Qs 100 mL | Qs 100 mL | Qs 100 mL | Qs 100 mL | Qs 100 mL | Qs 100 mL | Qs 100 mL | Qs 100 mL |

The formulation stability such as assay and impurities of the hydrocortisone formulations described herein can be tested, for example, using the HPLC method described in Table B-3, at different time points under various conditions, for example, after 1 month, 3 months, 6 months, 12 months, 24 months, and/or 36 months of storage at refrigerated conditions, ambient conditions, and/or accelerated conditions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Paragraphs of the Embodiments

Embodiment 1. A liquid pharmaceutical composition comprising:
hydrocortisone or a pharmaceutically acceptable salt thereof; and
a nonaqueous liquid carrier;
wherein the liquid pharmaceutical composition is an oral solution, and wherein the liquid pharmaceutical composition contains less than 5% wt of water.

Embodiment 2. The liquid pharmaceutical composition of embodiment 1, wherein the hydrocortisone or a pharmaceutically acceptable salt thereof is present in the liquid pharmaceutical composition in an amount of 0.8 mg/mL to 1.2 mg/mL.

Embodiment 3. The liquid pharmaceutical composition of embodiment 1, wherein the hydrocortisone or a pharmaceutically acceptable salt thereof is present in the liquid pharmaceutical composition in an amount of about 1 mg/mL.

Embodiment 4. The liquid pharmaceutical composition of embodiment 1, wherein the hydrocortisone or a pharmaceutically acceptable salt thereof is present in the liquid pharmaceutical composition in an amount of about 0.01% to about 10% weight by volume (w/v).

Embodiment 5. The liquid pharmaceutical composition of any one of embodiments 1 to 4, wherein the liquid pharmaceutical composition contains less than 3% wt of water.

Embodiment 6. The liquid pharmaceutical composition of any one of embodiments 1 to 5, wherein the liquid pharmaceutical composition contains less than 1% wt of water.

Embodiment 7. The liquid pharmaceutical composition of any one of embodiments 1 to 6, wherein the liquid pharmaceutical composition is nonaqueous.

Embodiment 8. The liquid pharmaceutical composition of any one of embodiments 1 to 7, wherein the nonaqueous liquid carrier is present in the liquid pharmaceutical composition in an amount of from about 70% wt to about 99.9% wt, from about 80% wt to about 99.9% wt, from about 90% wt to about 99.9% wt, or from about 95% wt to about 99.9% wt.

Embodiment 9. The liquid pharmaceutical composition of any one of embodiments 1 to 7, wherein the liquid pharmaceutical composition contains no more than 2% wt of total impurity after stored at about 2° C. to about 8° C. for 3, 6, 9, 12, 18, 24, 30, or 36 months.

Embodiment 10. The liquid pharmaceutical composition of any one of embodiments 1 to 9, wherein the liquid pharmaceutical composition contains no more than 2% wt of total impurity after stored at refrigerated conditions for 3, 6, 9, 12, 18, 24, 30, or 36 months.

Embodiment 11. The liquid pharmaceutical composition of any one of embodiments 1 to 9, wherein the liquid pharmaceutical composition contains no more than 2% wt of total impurity after stored at about 15° C. to about 25° C. for 3 months.

Embodiment 12. The liquid pharmaceutical composition of any one of embodiments 1 to 9, wherein the liquid pharmaceutical composition contains no more than 2% wt of total impurity after stored at about 15° C. to about 25° C. for 6, 9, 12, 18, or 24 months.

Embodiment 13. The liquid pharmaceutical composition of any one of embodiments 1 to 9, wherein the liquid pharmaceutical composition contains no more than 2% wt of total impurity after stored at about 15° C. to about 25° C., with temperature excursions permitted up to 30° C., for 3 months.

Embodiment 14. The liquid pharmaceutical composition of any one of embodiments 1 to 9, wherein the liquid pharmaceutical composition contains no more than 2% wt of total impurity after stored at about 15° C. to about 25° C., with temperature excursions permitted up to 30° C., for 6, 9, 12, 18, or 24 months.

Embodiment 15. The liquid pharmaceutical composition of any one of embodiments 1 to 9, wherein the liquid pharmaceutical composition contains no more than 2% wt of total impurity after stored at about 15° C. to about 30° C. for 3 months.

Embodiment 16. The liquid pharmaceutical composition of any one of embodiments 1 to 9, wherein the liquid pharmaceutical composition contains no more than 2% wt of total impurity after stored at about 15° C. to about 30° C. for 6, 9, 12, 18, or 24 months.

Embodiment 17. The liquid pharmaceutical composition of any one of embodiments 1 to 9, wherein the liquid pharmaceutical composition contains no more than 2% wt of total impurity after stored at room temperature for 3 months.

Embodiment 18. The liquid pharmaceutical composition of any one of embodiments 1 to 9, wherein the liquid pharmaceutical composition contains no more than 2% wt of total impurity after stored at room temperature for 6, 9, 12, 18, or 24 months.

Embodiment 19. The liquid pharmaceutical composition of any one of embodiments 1 to 9, wherein the liquid pharmaceutical composition contains no more than 2% wt of total impurity after stored at ambient conditions for 3 months.

Embodiment 20. The liquid pharmaceutical composition of any one of embodiments 1 to 9, wherein the liquid pharmaceutical composition contains no more than 2% wt of total impurity after stored at ambient conditions for 6, 9, 12, 18, or 24 months.

Embodiment 21. The liquid pharmaceutical composition of any one of embodiments 1 to 9, wherein the liquid pharmaceutical composition contains no more than 2% wt of total impurity after stored at about 40° C.±2° C. for 1 months.

Embodiment 22. The liquid pharmaceutical composition of any one of embodiments 1 to 9, wherein the liquid pharmaceutical composition contains no more than 2% wt of total impurity after stored at about 40° C.±2° C. for 2, 3, or 6 months.

Embodiment 23. The liquid pharmaceutical composition of any one of embodiments 1 to 9, wherein the liquid pharmaceutical composition contains no more than 2% wt of total impurity after stored at accelerated conditions for 1 months.

Embodiment 24. The liquid pharmaceutical composition of any one of embodiments 1 to 9, wherein the liquid pharmaceutical composition contains no more than 2% wt of total impurity after stored at accelerated conditions for 2, 3, or 6 months.

Embodiment 25. The liquid pharmaceutical composition of any one of embodiments 1 to 9, wherein the liquid pharmaceutical composition contains no more than 1% wt of total impurity after stored at about 2° C. to about 8° C. for 3, 6, 9, 12, 18, 24, 30, or 36 months.

Embodiment 26. The liquid pharmaceutical composition of any one of embodiments 1 to 9, wherein the liquid pharmaceutical composition contains no more than 1% wt of total impurity after stored at refrigerated conditions for 3, 6, 9, 12, 18, 24, 30, or 36 months.

Embodiment 27. The liquid pharmaceutical composition of any one of embodiments 1 to 9, wherein the liquid pharmaceutical composition contains no more than 1% wt of total impurity after stored at about 15° C. to about 25° C. for 3, 6, 9, 12, 18, or 24 months.

Embodiment 28. The liquid pharmaceutical composition of any one of embodiments 1 to 9, wherein the liquid pharmaceutical composition contains no more than 1% wt of total impurity after stored at about 15° C. to about 25° C., with temperature excursions permitted up to 30° C., for 3, 6, 9, 12, 18, or 24 months.

Embodiment 29. The liquid pharmaceutical composition of any one of embodiments 1 to 9, wherein the liquid pharmaceutical composition contains no more than 1% wt of total impurity after stored at about 15° C. to about 30° C. for 3, 6, 9, 12, 18, or 24 months.

Embodiment 30. The liquid pharmaceutical composition of any one of embodiments 1 to 9, wherein the liquid pharmaceutical composition contains no more than 1% wt of total impurity after stored at room temperature for 3, 6, 9, 12, 18, or 24 months.

Embodiment 31. The liquid pharmaceutical composition of any one of embodiments 1 to 9, wherein the liquid pharmaceutical composition contains no more than 1% wt of total impurity after stored at ambient conditions for 3, 6, 9, 12, 18, or 24 months.

Embodiment 32. The liquid pharmaceutical composition of any one of embodiments 1 to 9, wherein the liquid pharmaceutical composition contains no more than 1% wt of total impurity after stored at about 40° C.±2° C. for 1, 2, 3, or 6 months.

Embodiment 33. The liquid pharmaceutical composition of any one of embodiments 1 to 9, wherein the liquid pharmaceutical composition contains no more than 1% wt of total impurity after stored at accelerated conditions for 1, 2, 3, or 6 months.

Embodiment 34. The liquid pharmaceutical composition of any one of embodiments 9 to 33, wherein the total impurity is determined according to High-performance liquid chromatography (HPLC) method (e.g., described in Example B).

Embodiment 35. The liquid pharmaceutical composition of any one of embodiments 1 to 34 wherein the liquid pharmaceutical composition retains at least 95% wt of the initial hydrocortisone amount after stored at about 2° C. to about 8° C. for 3, 6, 9, 12, 18, 24, 30, or 36 months.

Embodiment 36. The liquid pharmaceutical composition of any one of embodiments 1 to 34, wherein the liquid pharmaceutical composition retains at least 95% wt of the initial hydrocortisone amount after stored at refrigerated conditions for 3, 6, 9, 12, 18, 24, 30, or 36 months.

Embodiment 37. The liquid pharmaceutical composition of any one of embodiments 1 to 34, wherein the liquid pharmaceutical composition retains at least 95% wt of the initial hydrocortisone amount after stored at about 15° C. to about 25° C. for 3 months.

Embodiment 38. The liquid pharmaceutical composition of any one of embodiments 1 to 34, wherein the liquid pharmaceutical composition retains at least 95% wt of the initial hydrocortisone amount after stored at about 15° C. to about 25° C. for 6, 9, 12, 18, or 24 months.

Embodiment 39. The liquid pharmaceutical composition of any one of embodiments 1 to 34, wherein the liquid pharmaceutical composition retains at least 95% wt of the initial hydrocortisone amount after stored at about 15° C. to about 25° C., with temperature excursions permitted up to 30° C., for 3 months.

Embodiment 40. The liquid pharmaceutical composition of any one of embodiments 1 to 34, wherein the liquid pharmaceutical composition retains at least 95% wt of the initial hydrocortisone amount after stored at about 15° C. to about 25° C., with temperature excursions permitted up to 30° C., for 6, 9, 12, 18, or 24 months.

Embodiment 41. The liquid pharmaceutical composition of any one of embodiments 1 to 34, wherein the liquid pharmaceutical composition retains at least 95% wt of the initial hydrocortisone amount after stored at about 15° C. to about 30° C. for 3 months.

Embodiment 42. The liquid pharmaceutical composition of any one of embodiments 1 to 34, wherein the liquid pharmaceutical composition retains at least 95% wt of the initial hydrocortisone amount after stored at about 15° C. to about 30° C. for 6, 9, 12, 18, or 24 months.

Embodiment 43. The liquid pharmaceutical composition of any one of embodiments 1 to 34, wherein the liquid pharmaceutical composition retains at least 95% wt of the initial hydrocortisone amount after stored at room temperature for 3 months.

Embodiment 44. The liquid pharmaceutical composition of any one of embodiments 1 to 34, wherein the liquid pharmaceutical composition retains at least 95% wt of the initial hydrocortisone amount after stored at room temperature for 6, 9, 12, 18, or 24 months.

Embodiment 45. The liquid pharmaceutical composition of any one of embodiments 1 to 34, wherein the liquid pharmaceutical composition retains at least 95% wt of the initial hydrocortisone amount after stored at ambient conditions for 3 months.

Embodiment 46. The liquid pharmaceutical composition of any one of embodiments 1 to 34, wherein the liquid pharmaceutical composition retains at least 95% wt of the initial hydrocortisone amount after stored at ambient conditions for 6, 9, 12, 18, or 24 months.

Embodiment 47. The liquid pharmaceutical composition of any one of embodiments 1 to 34, wherein the liquid pharmaceutical composition retains at least 95% wt of the initial hydrocortisone amount after stored at about 40° C.±2° C. for 1 month.

Embodiment 48. The liquid pharmaceutical composition of any one of embodiments 1 to 34, wherein the liquid pharmaceutical composition retains at least 95% wt of the initial hydrocortisone amount after stored at about 40° C.±2° C. for 2, 3, or 6 months.

Embodiment 49. The liquid pharmaceutical composition of any one of embodiments 1 to 34, wherein the liquid pharmaceutical composition retains at least 95% wt of the initial hydrocortisone amount after stored at accelerated conditions for 1 month.

Embodiment 50. The liquid pharmaceutical composition of any one of embodiments 1 to 34, wherein the liquid pharmaceutical composition retains at least 95% wt of the initial hydrocortisone amount after stored at accelerated conditions for 2, 3, or 6 months.

Embodiment 51. The liquid pharmaceutical composition of any one of embodiments 1 to 34, wherein the liquid pharmaceutical composition retains at least 98% wt of the initial hydrocortisone amount after stored at about 2° C. to about 8° C. for 3, 6, 9, 12, 18, 24, 30, or 36 months.

Embodiment 52. The liquid pharmaceutical composition of any one of embodiments 1 to 34, wherein the liquid pharmaceutical composition retains at least 98% wt of the initial hydrocortisone amount after stored at refrigerated conditions for 3, 6, 9, 12, 18, 24, 30, or 36 months.

Embodiment 53. The liquid pharmaceutical composition of any one of embodiments 1 to 34, wherein the liquid pharmaceutical composition retains at least 98% wt of the initial hydrocortisone amount after stored at about 15° C. to about 25° C., for 3, 6, 9, 12, 18, or 24 months.

Embodiment 54. The liquid pharmaceutical composition of any one of embodiments 1 to 34, wherein the liquid pharmaceutical composition retains at least 98% wt of the initial hydrocortisone amount after stored at about 15° C. to about 25° C., with temperature excursions permitted up to 30° C., for 3, 6, 9, 12, 18, or 24 months.

Embodiment 55. The liquid pharmaceutical composition of any one of embodiments 1 to 34, wherein the liquid pharmaceutical composition retains at least 98% wt of the initial hydrocortisone amount after stored at about 15° C. to about 30° C., for 3, 6, 9, 12, 18, or 24 months.

Embodiment 56. The liquid pharmaceutical composition of any one of embodiments 1 to 34, wherein the liquid pharmaceutical composition retains at least 98% wt of the initial hydrocortisone amount after stored at room temperature for 3, 6, 9, 12, 18, or 24 months.

Embodiment 57. The liquid pharmaceutical composition of any one of embodiments 1 to 34, wherein the liquid pharmaceutical composition retains at least 98% wt of the initial hydrocortisone amount after stored at ambient conditions for 3, 6, 9, 12, 18, or 24 months.

Embodiment 58. The liquid pharmaceutical composition of any one of embodiments 1 to 34, wherein the liquid pharmaceutical composition retains at least 98% wt of the initial hydrocortisone amount after stored at about 40° C.±2° C. for 1, 2, 3, or 6 months.

Embodiment 59. The liquid pharmaceutical composition of any one of embodiments 1 to 34, wherein the liquid pharmaceutical composition retains at least 98% wt of the initial hydrocortisone amount after stored at accelerated conditions for 1, 2, 3, or 6 months.

Embodiment 60. The liquid pharmaceutical composition of any one of embodiments 35 to 59, wherein the hydrocortisone amount is determined according to HPLC method (e.g., described in Example B).

Embodiment 61. The liquid pharmaceutical composition of any one of embodiments 1 to 60, wherein the liquid pharmaceutical composition remains stable after stored at about 2° C. to about 8° C. for at least 3, 6, 9, 12, 18, or 24 months.

Embodiment 62. The liquid pharmaceutical composition of any one of embodiments 1 to 61, wherein the liquid pharmaceutical composition remains stable after stored at refrigerated conditions for at least 3, 6, 9, 12, 18, or 24 months.

Embodiment 63. The liquid pharmaceutical composition of any one of embodiments 1 to 62, wherein the liquid pharmaceutical composition remains stable after stored at about 15° C. to about 25° C. for at least 3, 6, 9, 12, 18, or 24 months.

Embodiment 64. The liquid pharmaceutical composition of any one of embodiments 1 to 63, wherein the liquid pharmaceutical composition remains stable after stored at about 15° C. to about 25° C., with temperature excursions permitted up to 30° C., for at least 3, 6, 9, 12, 18, or 24 months.

Embodiment 65. The liquid pharmaceutical composition of any one of embodiments 1 to 59, wherein the liquid pharmaceutical composition remains stable after stored at about 15° C. to about 30° C. for at least 3, 6, 9, 12, 18, or 24 months.

Embodiment 66. The liquid pharmaceutical composition of any one of embodiments 1 to 65, wherein the liquid pharmaceutical composition remains stable after stored at room temperature for at least 3, 6, 9, 12, 18, or 24 months.

Embodiment 67. The liquid pharmaceutical composition of any one of embodiments 1 to 66, wherein the liquid pharmaceutical composition remains stable after stored at ambient conditions for at least 3, 6, 9, 12, 18, or 24 months.

Embodiment 68. The liquid pharmaceutical composition of any one of embodiments 1 to 67, wherein the liquid pharmaceutical composition remains stable after stored at about 40° C.±2° C. for at least 1, 2, 3, or 6 months.

Embodiment 69. The liquid pharmaceutical composition of any one of embodiments 1 to 68, wherein the liquid pharmaceutical composition remains stable after stored at accelerated conditions for at least 1, 2, 3, or 6 months.

Embodiment 70. The liquid pharmaceutical composition of any one of embodiments 1 to 69, wherein the nonaqueous liquid carrier comprises propylene glycol, glycerin, polyethylene glycol (PEG), alcohol, or a combination thereof.

Embodiment 71. The liquid pharmaceutical composition of embodiment 70, wherein the nonaqueous liquid carrier comprises propylene glycol, glycerin, and PEG.

Embodiment 72. The liquid pharmaceutical composition of embodiment 70 or 71, wherein the PEG is PEG400.

Embodiment 73. The liquid pharmaceutical composition of any one of embodiments 70 to 72, wherein the PEG has a number average molecular weight of about 350 to about 450 g/mol.

Embodiment 74. The liquid pharmaceutical composition of any one of embodiments 1 to 73, wherein the PEG is present in the liquid pharmaceutical composition in an amount of about 30% to about 70% w/v.

Embodiment 75. The liquid pharmaceutical composition of any one of embodiments 1 to 73, wherein the PEG is present in the liquid pharmaceutical composition in an amount of about 40% to about 60% w/v.

Embodiment 76. The liquid pharmaceutical composition of any one of embodiments 1 to 73, wherein the PEG is present in the liquid pharmaceutical composition in an amount of about 45% to about 55% w/v.

Embodiment 77. The liquid pharmaceutical composition of any one of embodiments 1 to 76, wherein the propylene glycol is present in the liquid pharmaceutical composition in an amount of about 0.5% to about 10% w/V.

Embodiment 78. The liquid pharmaceutical composition of any one of embodiments 1 to 76, wherein the propylene glycol is present in the liquid pharmaceutical composition in an amount of about 4% to about 6% w/v.

Embodiment 79. The liquid pharmaceutical composition of any one of embodiments 1 to 78, wherein the glycerin is present in the liquid pharmaceutical composition in an amount of about 40% to about 80% w/v.

Embodiment 80. The liquid pharmaceutical composition of any one of embodiments 1 to 78, wherein the glycerin is present in the liquid pharmaceutical composition in an amount of about 50% to about 70% w/v.

Embodiment 81. The liquid pharmaceutical composition of any one of embodiments 1 to 80, wherein the liquid pharmaceutical composition comprises a preservative.

Embodiment 82. The liquid pharmaceutical composition of embodiment 81, wherein the preservative comprises an antimicrobial agent, a chelating agent, an antioxidant, or a combination thereof.

Embodiment 83. The liquid pharmaceutical composition of embodiment 82, wherein the antimicrobial agent comprises a paraben or a mixture of parabens, benzoic acid or a pharmaceutically acceptable salt thereof, sorbic acid or a pharmaceutically acceptable salt thereof, phenoxyethanol, benzyl alcohol, propionic acid, or a combination thereof.

Embodiment 84. The liquid pharmaceutical composition of embodiment 83, wherein the mixture of parabens comprises methyl paraben, ethyl paraben, propyl paraben, or a combination thereof.

Embodiment 85. The liquid pharmaceutical composition of any one of embodiments 82 to 84, wherein the chelating agent comprises disodium ethylenediaminetetraacetic acid, polyphosphates, citric acid, calcium disodium edetate, ethylenediaminetetraacetic acid (EDTA), or a combination thereof.

Embodiment 86. The liquid pharmaceutical composition of any one of embodiments 82 to 85, wherein the antioxidant comprises vitamin A, monothioglycerol, ascorbic acid, sodium bisulfite, sodium sulfite, α-Tocopherol acetate (vitamin E), butylated hydroxyanisole (BHA), butylated hydroxytoluene (BHT), or a combination thereof.

Embodiment 87. The liquid pharmaceutical composition of any one of embodiments 1 to 86, wherein the liquid pharmaceutical composition comprises a flavoring agent.

Embodiment 88. The liquid pharmaceutical composition of embodiment 87, wherein the flavoring agent comprises a natural flavoring agent, an artificial flavoring agent, or a combination thereof.

Embodiment 89. The liquid pharmaceutical composition of embodiment 87 or 88, wherein the flavoring agent comprises vanillin, grape flavor, caramel flavor, maltol, raspberry flavor, fruity flavor, or berry flavor.

Embodiment 90. The liquid pharmaceutical composition of any one of embodiments 87 to 89, wherein the flavoring agent comprises 4-hydroxy-3-methoxybenzaldehyde, methyl anthranilate, 3,5-dimethyl-1,2-cyclopentadione, maltol, 4-(4-hydroxyphenyl)butan-2-one, ethyl maltol, or ethyl propionate.

Embodiment 91. The liquid pharmaceutical composition of any one of embodiments 1 to 90, wherein the pharmaceutical composition comprises a sweetener.

Embodiment 92. The liquid pharmaceutical composition of embodiment 91, wherein the sweetener is a sugar (e.g., glucose, fructose, sucrose, lactose, maltose) or sugar alcohol (e.g., xylitol, mannitol, lactitol, maltitol, or sorbitol).

Embodiment 93. The liquid pharmaceutical composition of embodiment 91, wherein the sweetener is glucose, fructose, sucrose, xylitol, tagatose, sucralose, maltitol, isomaltulose, hydrogenated isomaltulose, lactitol, sorbitol, erythritol, trehalose, maltodextrin, or polydextrose.

Embodiment 94. The liquid pharmaceutical composition of any one of embodiments 1 to 93, wherein the pharmaceutical composition comprises
- hydrocortisone or a pharmaceutically acceptable salt thereof in an amount of about 0.01% to about 2% weight by volume (w/v);
- a nonaqueous liquid carrier comprising propylene glycol, glycerin, PEG, or a combination thereof;
- a preservative comprising an antioxidant, an antimicrobial agent, or a combination thereof; optionally, a sweetener; and
- optionally, a flavoring agent.

Embodiment 95. The liquid pharmaceutical composition of embodiment 94, wherein the pharmaceutical composition comprises:
- hydrocortisone or a pharmaceutically acceptable salt thereof in an amount of about 0.05% to about 0.5% w/v;
- a nonaqueous liquid carrier comprising propylene glycol, glycerin, and polyethylene glycol 400 (PEG 400), wherein the propylene glycol is present in an amount of about 2% to about 10% w/v, wherein the PEG 400 is present in an amount of about 20% to about 70% w/v, wherein the glycerin is present in an amount of about 40% to about 80% w/v;
- a preservative comprising an antioxidant and an antimicrobial agent, wherein the antioxidant comprises BHA, BHT, or a combination thereof, wherein the antimicrobial agent comprises parabens;
- optionally, a sweetener (e.g., sucralose); and
- optionally, a flavoring agent (e.g., a flavoring agent comprising berry flavor, maltol, ethyl maltol, or a combination thereof).

Embodiment 96. The liquid pharmaceutical composition of embodiment 94 or 95, wherein the liquid pharmaceutical composition comprises
- hydrocortisone or a pharmaceutically acceptable salt thereof in an amount of about 0.05% to about 0.5% w/v;
- a nonaqueous liquid carrier comprising propylene glycol, glycerin, and polyethylene glycol 400 (PEG 400), wherein the propylene glycol is present in an amount of about 3% to about 7% w/v, wherein the PEG 400 is present in an amount of about 30% to about 60% w/v, wherein the glycerin is present in an amount of about 60% to about 70% w/v;
an antioxidant comprising BHA, BHT, or a combination thereof, wherein the antioxidant is present in an amount of about 0.005% to about 0.05% w/v;
an antimicrobial agent comprising methyl paraben, propyl paraben, or a combination thereof, wherein the antimicrobial agent is present in an amount of about 0.05% to about 0.5% w/v;
optionally, a sweetener in an amount of about 0.05% to about 5% w/v; and
optionally, a flavoring agent in an amount of about 0.05% to about 1% w/v.

Embodiment 97. The liquid pharmaceutical composition of embodiment 94 or 95, wherein the pharmaceutical composition comprises
hydrocortisone or a pharmaceutically acceptable salt thereof in an amount of about 0.1% w/v;
a nonaqueous liquid carrier comprising propylene glycol, glycerin, and polyethylene glycol 400 (PEG 400), wherein the propylene glycol is present in an amount of about 5% w/v, wherein the PEG 400 is present in an amount of about 50% w/v, wherein the glycerin is present in an amount of about 62.2% w/v;
an antioxidant comprising BHA in an amount of about 0.01% w/v;
an antimicrobial agent comprising methyl paraben and propyl paraben, wherein the methyl paraben is present in an amount of about 0.18% w/v, and wherein propyl paraben is present in an amount of about 0.02% w/v; and
sucralose in an amount of about 1% w/v, berry flavor in an amount of about 0.2% w/v, and ethyl maltol in an amount of about 0.1% to about 0.2% w/v.

Embodiment 98. A method of treating a disease or condition, comprising administering the liquid pharmaceutical composition of any one of embodiments 1 to 97, to a subject in need thereof.

Embodiment 99. The method of embodiment 98, wherein the liquid pharmaceutical composition is administered to the subject orally or through a nasogastric, jejunostomy, or gastrostomy tube.

Embodiment 100. The method of embodiment 98 or 99, wherein the disease or condition is selected from endocrine disorders, rheumatic disorders, collagen diseases, dermatologic diseases, allergic states, ophthalmic diseases, respiratory diseases, hematologic disorders, neoplastic diseases, edematous states, gastrointestinal diseases, acute exacerbation in multiple sclerosis, tuberculous meningitis with subarachnoid block or impending block when used concurrently with appropriate anti-tuberculous chemotherapy, and trichinosis with neurologic or myocardial involvement.

Embodiment 101. The method of embodiment 100, wherein the endocrine disorders comprise primary or secondary adrenocortical insufficiency, congenital adrenal hyperplasia, non-suppurative thyroiditis, or hypercalcemia associated with cancer.

Embodiment 102. The method of embodiment 100, wherein the rheumatic disorders comprise psoriatic arthritis, rheumatoid arthritis, including juvenile rheumatoid arthritis, ankylosing spondylitis, acute and subacute bursitis, acute nonspecific tenosynovitis, acute gouty arthritis, post-traumatic osteoarthritis, synovitis of osteoarthritis, or epicondylitis.

Embodiment 103. The method of embodiment 100 or 102, wherein the liquid pharmaceutical composition is used to treat rheumatic disorders as an adjunctive therapy for short-term administration to tide the subject over an acute episode or exacerbation.

Embodiment 104. The method of embodiment 100, wherein the collagen diseases comprise systemic lupus erythematosus, systemic dermatomyositis (polymyositis), or acute rheumatic carditis.

Embodiment 105. The method of embodiment 100 or 104, wherein the liquid pharmaceutical composition is used to treat collagen diseases during an exacerbation or as a maintenance therapy.

Embodiment 106. The method of embodiment 100, wherein the dermatologic diseases comprise pemphigus, bullous dermatitis herpetiformis, severe erythema multiforme (Stevens-Johnson syndrome), exfoliative dermatitis, mycosis fungoides, severe psoriasis, or severe seborrheic dermatitis.

Embodiment 107. The method of embodiment 100, wherein the allergic states comprise seasonal or perennial allergic rhinitis, serum sickness, bronchial asthma, contact dermatitis, atopic dermatitis, or drug hypersensitivity reactions.

Embodiment 108. The method of embodiment 100 or 107, wherein the liquid pharmaceutical composition is used to treat allergic states for control of severe or incapacitating allergic conditions intractable to adequate trials of conventional treatment.

Embodiment 109. The method of embodiment 100, wherein the ophthalmic diseases comprise allergic conjunctivitis, keratitis, allergic corneal marginal ulcers, herpes zoster ophthalmicus, iritis and iridocyclitis, chorioretinitis, anterior segment inflammation, diffuse posterior uveitis and choroiditis, optic neuritis, or sympathetic ophthalmia.

Embodiment 110. The method of embodiment 100, wherein the respiratory diseases comprise symptomatic sarcoidosis, Loeffler's syndrome, berylliosis, fulminating or disseminated pulmonary tuberculosis when used concurrently with appropriate anti-tuberculous chemotherapy, or aspiration pneumonitis.

Embodiment 111. The method of embodiment 100, wherein the hematologic disorders comprise idiopathic thrombocytopenic purpura in adults, secondary thrombocytopenia in adults, acquired (autoimmune) hemolytic anemia, erythroblastopenia (RBC anemia), or congenital (erythroid) hypoplastic anemia.

Embodiment 112. The method of embodiment 100, wherein the neoplastic diseases comprise leukemias and lymphomas in adults, or acute leukemia of childhood.

Embodiment 113. The method of embodiment 100 or 112, wherein the liquid pharmaceutical composition is used to treat neoplastic diseases for palliative management.

Embodiment 114. The method of embodiment 100, wherein the edematous states comprise proteinuria in nephrotic syndrome.

Embodiment 115. The method of embodiment 114, wherein the liquid pharmaceutical composition is used to induce a diuresis or remission of proteinuria in the nephrotic syndrome, without uremia, of the idiopathic type or that due to lupus erythematosus.

Embodiment 116. The method of embodiment 100, wherein the gastrointestinal diseases comprise ulcerative colitis or regional enteritis.

Embodiment 117. The method of embodiment 100 or 116, wherein the liquid pharmaceutical composition is used to tide the subject over a critical period of the gastrointestinal diseases.

Embodiment 118. The method of any one of embodiments 98 to 101, wherein the disease or condition is adrenal insufficiency in subjects who are not older than 17 years in age.

Embodiment 119. The method of any one of embodiments 98 to 118, wherein the liquid pharmaceutical composition is administered in a therapeutically effective amount.

Embodiment 120. A method of making the liquid pharmaceutical composition of any one of embodiments 1 to 97, wherein the method comprises
 a. mixing hydrocortisone or a pharmaceutically acceptable salt thereof with a nonaqueous liquid carrier, thereby forming a solution of hydrocortisone in the nonaqueous liquid carrier.

Embodiment 121. The method of embodiment 120, wherein the method comprises adding a preservative, optionally a sweeter, and optionally a flavoring agent into the solution of hydrocortisone.

Embodiment 122. The method of embodiment 121, wherein the preservative, optionally the sweeter, and optionally the flavoring agent is added to the nonaqueous liquid carrier before mixing hydrocortisone or a pharmaceutically acceptable salt thereof with the nonaqueous liquid carrier.

Embodiment 123. The method of any one of embodiments 120 to 122, wherein the method comprises optionally filtering the solution of hydrocortisone over a filter into a container.

Embodiment 124. The method of embodiment 123, wherein the filter is a 5 m disposable filter.

Embodiment 125. A kit comprising a package enclosing the liquid pharmaceutical composition of any one of embodiments 1 to 97.

Embodiment 126. The kit of embodiment 125, wherein the kit comprises instructions for use of the liquid pharmaceutical composition.

Embodiment 127. The kit of embodiments 125 or 126, wherein the package is a bottle.

Embodiment 128. The kit of embodiment 127, wherein the bottle has a light protection mechanism.

What is claimed is:

1. A liquid pharmaceutical composition comprising:
 hydrocortisone or a pharmaceutically acceptable salt thereof, wherein the hydrocortisone or the pharmaceutically acceptable salt thereof comprises hydrocortisone free base, hydrocortisone acetate, hydrocortisone sodium succinate, or hydrocortisone sodium phosphate; and
 a nonaqueous liquid carrier, wherein the nonaqueous liquid carrier is present in the liquid pharmaceutical composition in an amount of from about 70% weight by weight (% wt) to about 99.9% wt;
 wherein the hydrocortisone or the pharmaceutically acceptable salt thereof is present in the liquid pharmaceutical composition in an amount of about 1 mg/mL; and
 wherein the liquid pharmaceutical composition is a liquid for oral administration, and wherein the liquid pharmaceutical composition contains less than 5% wt of water.

2. The liquid pharmaceutical composition of claim 1, wherein the hydrocortisone or the pharmaceutically acceptable salt thereof is present in the liquid pharmaceutical composition in an amount of from about 0.01% weight by volume (w/v) to about 1% w/v.

3. The liquid pharmaceutical composition of claim 1, wherein the hydrocortisone or the pharmaceutically acceptable salt thereof is present in the liquid pharmaceutical composition in an amount of from about 0.01% w/v to about 10% w/v.

4. The liquid pharmaceutical composition of claim 1, wherein the liquid pharmaceutical composition is nonaqueous.

5. The liquid pharmaceutical composition of claim 1, wherein the liquid pharmaceutical composition contains no more than 2% wt of total impurity after stored at room temperature for 3 months, and wherein the total impurity is determined according to high-performance liquid chromatography (HPLC).

6. The liquid pharmaceutical composition of claim 1, wherein the liquid pharmaceutical composition retains at least 95% wt of an initial hydrocortisone amount after stored at room temperature for 3 months, and wherein a hydrocortisone amount is determined according to HPLC.

7. The liquid pharmaceutical composition of claim 1, wherein the liquid pharmaceutical composition remains stable after stored at ambient conditions for at least 3 months.

8. The liquid pharmaceutical composition of claim 1, wherein the nonaqueous liquid carrier comprises propylene glycol, glycerin, polyethylene glycol (PEG), alcohol, or a combination thereof.

9. The liquid pharmaceutical composition of claim 1, wherein the nonaqueous liquid carrier comprises ethanol.

10. The liquid pharmaceutical composition of claim 1, wherein the nonaqueous liquid carrier comprises PEG, and wherein PEG is present in the liquid pharmaceutical composition in an amount of from about 20% to w/v about 80% w/v.

11. The liquid pharmaceutical composition of claim 1, wherein the nonaqueous liquid carrier comprises glycerin, and wherein glycerin is present in the liquid pharmaceutical composition in an amount of from about 20% w/v to about 90% w/v.

12. The liquid pharmaceutical composition of claim 1, wherein the liquid pharmaceutical composition further comprises a preservative, and wherein the preservative comprises an antimicrobial agent, a chelating agent, or an antioxidant, or any combinations thereof.

13. The liquid pharmaceutical composition of claim 12, wherein the preservative comprises an antimicrobial agent, and wherein the antimicrobial agent comprises methyl paraben, ethyl paraben, propyl paraben, benzoic acid or a pharmaceutically acceptable salt thereof, sorbic acid or a pharmaceutically acceptable salt thereof, phenoxyethanol, benzyl alcohol, propionic acid, or a combination thereof.

14. The liquid pharmaceutical composition of claim 12, wherein the preservative comprises a chelating agent, and wherein the chelating agent comprises disodium ethylenediaminetetraacetic acid, polyphosphates, citric acid, calcium disodium edetate, ethylenediaminetetraacetic acid (EDTA), or a combination thereof.

15. The liquid pharmaceutical composition of claim 12, wherein the preservative comprises an antioxidant, and wherein the antioxidant comprises vitamin A, monothioglycerol, ascorbic acid, sodium bisulfite, sodium sulfite, α-Tocopherol acetate (vitamin E), butylated hydroxyanisole (BHA), butylated hydroxytoluene (BHT), or a combination thereof.

16. The liquid pharmaceutical composition of claim 1, wherein the liquid pharmaceutical composition further comprises a flavoring agent.

17. The liquid pharmaceutical composition of claim 1, wherein the liquid pharmaceutical composition further comprises a sweetener.

18. The liquid pharmaceutical composition of claim 1,
wherein the hydrocortisone or the pharmaceutically acceptable salt thereof comprises hydrocortisone free base;
wherein the nonaqueous liquid carrier comprises propylene glycol, glycerin, PEG, or a combination thereof;
wherein the liquid pharmaceutical composition further comprises:
a preservative comprising an antioxidant, an antimicrobial agent, or a combination thereof;
optionally, a sweetener; and
optionally, a flavoring agent.

19. The liquid pharmaceutical composition of claim 1, comprising hydrocortisone free base.

20. The liquid pharmaceutical composition of claim 1, wherein the liquid pharmaceutical composition is an oral solution.

21. A kit comprising a package enclosing the liquid pharmaceutical composition of claim 1.

22. The liquid pharmaceutical composition of claim 1, wherein the hydrocortisone or the pharmaceutically acceptable salt thereof is the only active ingredient of the liquid pharmaceutical composition.

23. The liquid pharmaceutical composition of claim 1, wherein the nonaqueous liquid carrier does not include an oil.

24. A liquid pharmaceutical composition comprising:
hydrocortisone or a pharmaceutically acceptable salt thereof, wherein the hydrocortisone or the pharmaceutically acceptable salt thereof comprises hydrocortisone free base, hydrocortisone acetate, hydrocortisone sodium succinate, or hydrocortisone sodium phosphate; and
a nonaqueous liquid carrier, wherein the nonaqueous liquid carrier is present in the liquid pharmaceutical composition in an amount of from about 70% weight by weight (% wt) to about 99.9% wt;
wherein the nonaqueous liquid carrier comprises propylene glycol, and wherein propylene glycol is present in the liquid pharmaceutical composition in an amount of from about 0.5% weight by volume (w/v) to about 10% w/v; and
wherein the liquid pharmaceutical composition is a liquid for oral administration, and wherein the liquid pharmaceutical composition contains less than 5% wt of water.

25. A kit comprising a package enclosing the liquid pharmaceutical composition of claim 24.

* * * * *